US006767915B2

(12) United States Patent
Bakshi et al.

(10) Patent No.: US 6,767,915 B2
(45) Date of Patent: Jul. 27, 2004

(54) SUBSTITUTED PIPERIDINES AS MELANOCORTIN RECEPTOR AGONISTS

(75) Inventors: Raman K. Bakshi, Edison, NJ (US); Khaled J. Barakat, Brooklyn, NY (US); Yingjie Lai, Edison, NJ (US); Ravi P. Nargund, East Brunswick, NJ (US); Brenda L. Palucki, Hillsborough, NJ (US); Min K. Park, Whippany, NJ (US); Iyassu K. Sebhat, New York, NY (US); Zhixiong Ye, Princeton, NJ (US); Arthur A. Patchett, Westfield, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/343,040

(22) PCT Filed: Aug. 17, 2001

(86) PCT No.: PCT/US01/25757
§ 371 (c)(1),
(2), (4) Date: Jan. 27, 2003

(87) PCT Pub. No.: WO02/15909
PCT Pub. Date: Feb. 28, 2002

(65) Prior Publication Data
US 2003/0236262 A1 Dec. 25, 2003

Related U.S. Application Data
(60) Provisional application No. 60/227,180, filed on Aug. 23, 2000.

(51) Int. Cl.$^7$ ..................... A61K 31/445; C07D 211/18
(52) U.S. Cl. ....................... 514/325; 546/203; 546/205; 546/202; 546/199; 546/198; 546/194; 514/330; 514/324; 514/322; 514/318; 514/326
(58) Field of Search ................................. 514/325, 330, 514/324, 323, 322, 318, 326; 546/203, 205, 202, 199, 198, 194

(56) References Cited

U.S. PATENT DOCUMENTS

| | | |
|---|---|---|
| 5,492,920 A | 2/1996 | Chen et al. |
| 5,536,716 A | 7/1996 | Chen et al. |
| 5,576,290 A | 11/1996 | Hadley |
| 5,714,497 A | 2/1998 | Christophe et al. |
| 5,721,251 A | 2/1998 | Chen et al. |
| 5,767,118 A | 6/1998 | Nargund et al. |
| 6,051,555 A | 4/2000 | Hadley |
| 6,410,548 B2 | 6/2002 | Nargund et al. |

FOREIGN PATENT DOCUMENTS

| | | |
|---|---|---|
| WO | WO 97/34604 | 9/1997 |
| WO | WO 98/10653 | 3/1998 |
| WO | WO 99/64002 | 12/1999 |
| WO | WO 00/74679 A1 | 12/2000 |

OTHER PUBLICATIONS

Corcos et al., Society for Neuroscience, vol. 23 (1997), Abstract 267.9, "HP 228 is a potent agonist of melanocortin receptor 4, and significantly attenuates obesity and diabetes in Zucker fatty rats".

Wessells et al., J. of Urology, vol. 160(2), (1998), pp. 389–393, "Synthetic melanotropic peptide initiates erections in men with pyschogenic erectile dysfunction . . . ".

Giraudo et al., Brain Research, vol. 809 (1998), pp. 302–306, "Feeding effects of hypothalamic injection of melanocortin 4 receptor ligands".

Carpino, Exp. Opin. Ther. Patents (2000), vol. 10(6), pp. 819–831, "Patent focus on new anti–obesity agents: Sep. 1999 –Feb. 2000".

Chaki et al., Exp. Opin. Ther. Patents (2001), vol. 11(11), pp. 1677–1692, "Recent advances in feeding suppressing agents: potential therapeutic strategy for the treatment of obesity".

Wessells et al., Urology (2000), vol. 56, pp. 641–646, "Effect of an alpha–melanocyte stimulating hormone analog on penile erection and sexual desire in men with organic erectile dysfunction".

Dorr et al., Life Sciences, vol. 58 (1996), pp. 1777–1784, "Evaluation of melanotan–II, a superpotent cyclic melanotropic peptide in a pilot phase–I clinical study".

Moreland et al., Life Sciences, vol. 62 (1998), pp. 309–318, "Sildenafil, a novel inhibitor of phosphodiesterase type 5 in human corpus cavernosum smooth muscle cells".

Gingell et al., Exp. Opin. Ther. Patents (1999), vol. 9(12), pp. 1689–1696, "Emerging pharamcological therapies for erectile dysfunction".

Dinsmore et al., BMJ, vol. 318 (1999), pp. 387–390, "ABC of sexual health: Erectile dysfunction".

Chen et al., Cell, vol. 91 (1997), pp. 789–798, "Exocrine gland dysfunction in MC5–R–deficient mice: . . . ".

Kask et al., Biochem. & Biophys. Res. Comm., vol. 245 (1998), pp. 90–93, "Selective antagonist for the melanocortin 4 receptor (HS014) increases food intake in free–feeding rats".

Huszar et al., Cell, vol. 88 (1997), pp. 131–141, "Targeted disruption of the melanocortin–4 receptor results in obesity in mice".

Yoram et al., Current Opinion in Urology, vol. 7 (1997), pp. 349–353, "Oral pharmacotherapy in erectile dysfunction".

Peptides: Frontiers of Peptide Science, Fifteenth American Peptide Symposium, Jun. 14–19, 1997 (Nashville, TN).

Heaton et al., Int'l J. of Impotence Research, vol. 9 (1997), pp. 115–121, "A therapeutic taxonomy of treatments for erectile dysfunction: An evolutionary imperative".

Graul, Drug News & Perspectives, vol. 9(9) (1996, pp. 572–575, "Latest findings on the diagnosis and treatment of erectile dysfunction".

*Primary Examiner*—Charanjit S. Aulakh
(74) *Attorney, Agent, or Firm*—Baerbel R. Brown; Catherine D. Fitch

(57) ABSTRACT

Certain novel 4-substituted piperidine compounds are agonists of the human melanocortin receptor(s) and, in particular, are selective agonists of the human melanocortin-4 receptor (MC-4R). They are therefore useful for the treatment, control, or prevention of diseases and disorders responsive to the activation of MC-4R, such as obesity, diabetes, sexual dysfunction, including erectile dysfunction and female sexual dysfunction.

29 Claims, No Drawings

SUBSTITUTED PIPERIDINES AS MELANOCORTIN RECEPTOR AGONISTS

CROSS-REFERENCE TO RELATED APPLICATIONS

This application is a U.S. National Phase application under 35 U.S.C. §371 of PCT Application No. PCT/US01/25757, filed Aug. 17, 2001, now WO 02/15909, which claims priority under 35 U.S.C. 119 from U.S. Provisional Application No. 60/227,180, filed Aug. 23, 2000.

SUMMARY OF THE INVENTION

The present invention relates to piperidine derivatives, their synthesis, and their use as melanocortin receptor (MC-R) agonists. More particularly, the compounds of the present invention are selective agonists of the melanocortin-4 receptor (MC-4R) and are thereby useful for the treatment of disorders responsive to the activation of MC-4R, such as obesity, diabetes, and male and/or female sexual dysfunction.

BACKGROUND OF THE INVENTION

Pro-opiomelanocortin (POMC) derived peptides are known to affect food intake. Several lines of evidence support the notion that the G-protein coupled receptors (GPCRs) of the melanocortin receptor (MC-R) family, several of which are expressed in the brain, are the targets of POMC derived peptides involved in the control of food intake and metabolism. A specific single MC-R that may be targeted for the control of obesity has not yet been identified, although evidence has been presented that MC-4R signalling is important in mediating feed behavior (S. Q. Giraudo et al., "Feeding effects of hypothalamic injection of melanocortin-4 receptor ligands," Brain Research, 80: 302–306 (1998)).

Evidence for the involvement of MC-R's in obesity includes: i) the agouti ($A^{vy}$) mouse which ectopically expresses an antagonist of the MC-1R, MC-3R and -4R is obese, indicating that blocking the action of these three MC-R's can lead to hyperphagia and metabolic disorders; ii) MC-4R Inockout mice (D. Huszar et al., Cell, 88: 131–141 (1997)) recapitulate the phenotype of the agouti mouse and these mice are obese; iii) the cyclic heptapeptide MT-II (a non-selective MC-1R, -3R, -4R, and -5R agonist) injected intracerebroventricularly (ICV) in rodents, reduces food intake in several animal feeding models (NPY, ob/ob, agouti, fasted) while ICV injected SHU-9119 (MC-3R and 4R antagonist; MC-1R and -5R agonist) reverses this effect and can induce hyperphagia; iv) chronic intraperitoneal treatment of Zucker fatty rats with an α-NDP-MSH derivative (HP228) has been reported to activate MC-1R, -3R, -4R, and -5R and to attenuate food intake and body weight gain over a 12-week period (I. Corcos et al., "HP228 is a potent agonist of melanocortin receptor-4 and significantly attenuates obesity and diabetes in Zucker fatty rats," Society for Neuroscience Abstracts, 23: 673 (1997)).

Five distinct MC-R's have thus far been identified, and these are expressed in different tissues. MC-1R was initially characterized by dominant gain of function mutations at the Extension locus, affecting coat color by controlling phaeomelanin to eumelanin conversion through control of tyrosinase. MC-1R is mainly expressed in melanocytes. MC-2R is expressed in the adrenal gland and represents the ACTH receptor. MC-3R is expressed in the brain, gut, and placenta and may be involved in the control of food intake and thermogenesis. MC-4R is uniquely expressed in the brain, and its inactivation was shown to cause obesity (A. Kask, et al., "Selective antagonist for the melanocortin-4 receptor (HS014) increases food intake in free-feeding rats," Biochem. Biophys. Res. Commun., 245: 90–93 (1998)). MC-5R is expressed in many tissues, including white fat, placenta and exocrine glands. A low level of expression is also observed in the brain. MC-5R knockout mice reveal reduced sebaceous gland lipid production (Chen et al., Cell, 91: 789–798 (1997)).

Erectile dysfunction denotes the medical condition of inability to achieve penile erection sufficient for successful sexual intercourse. The term "impotence" is oftentimes employed to describe this prevalent condition. Approximately 140 million men worldwide, and, according to a National Institutes of Health study, about 30 million American men suffer from impotency or erectile dysfunction. It has been estimated that the latter number could rise to 47 million men by the year 2000. Erectile dysfunction can arise from either organic or psychogenic causes, with about 20% of such cases being purely psychogenic in origin. Erectile dysfunction increases from 40% at age 40, to 67% at age 75, with over 75% occurring in men over the age of 50. In spite of the frequent occurrence of this condition, only a small number of patients have received treatment because existing treatment alternatives, such as injection therapies, penile prosthesis implantation, and vacuum pumps, have been uniformly disagreeable [for a discussion, see "ABC of sexual health—erectile dysfunction," Brit. Med. J. 318: 387–390 (1999)]. Only more recently have more viable treatment modalities become available, in particular orally active agents, such as sildenafil citrate, marketed by Pfizer under the brand name of Viagra®. (See "Emerging pharmacological therapies for erectile dysfunction," Exp. Opin. Ther. Patents 9: 1689–1696 (1999)). Sildenafil is a selective inhibitor of type V phosphodiesterase (PDE-V), a cyclic-GMP-specific phosphodiesterase isozyme [see R. B. Moreland et al, "Sildenafil: A Novel Inhibitor of Phosphodiesterase Type 5 in Human Corpus Cavemosum Smooth Muscle Cells," Life Sci., 62: 309–318 (1998)]. Prior to the introduction of Viagra on the market, less than 10% of patients suffering from erectile dysfunction received treatment. Sildenafil is also being evaluated in the clinic for the treatment of female sexual dysfunction.

The regulatory approval of Viagra® for the oral treatment of erectile dysfunction has invigorated efforts to discover even more effective methods to treat erectile dysfunction. Several additional selective PDE-V inhibitors are in clinical trials. UK-114542 is a sildenafil backup from Pfizer with supposedly improved properties. IC-351 (ICOS Corp.) is claimed to have greater selectivity for PDE-V over PDE-VI than sildenafil. Other PDE-V inhibitors include M-54033 and M-54018 from Mochida Pharmaceutical Co. and E4010 from Eisai Co., Ltd.

Other pharmacological approaches to the treatment of erectile dysfunction have been described [see, e.g., "Latest Findings on the Diagnosis and Treatment of Erectile Dysfunction," Drug News & Perspectives, 9: 572–575 (1996); "Oral Pharmacotherapy in Erectile Dysfunction," Current Opinion in Urology, 7: 349–353 (1997)]. A product under clinical development by Zonagen is an oral formulation of the alpha-adrenoceptor antagonist phentolamine mesylate under the brand name of Vasomax®. Vasomax® is also being evaluated for the treatment of female sexual dysfunction.

Drugs to treat erectile dysfunction act either peripherally or centrally. They are also classified according to whether they "initiate" a sexual response or "facilitate" a sexual response to prior stimulation [for a discussion, see "A Therapeutic Taxonomy of Treatments for Erectile Dysfunction: An Evolutionary Imperative," *Int. J. Impotence Res.,* 9: 115–121 (1997)]. While sildenafil and phentolamine act peripherally and are considered to be "enhancers" or "facilitators" of the sexual response to erotic stimulation, sildenafil appears to be efficacious in both mild organic and psychogenic erectile dysfunction. Sildenafil has an onset of action of 30–60 minutes after an oral dose with the effect lasting about 4 hours, whereas phentolamine requires 5–30 minutes for onset with a duration of 2 hours. Although sildenafil is effective in a majority of patients, it takes a relatively long time for the compound to show the desired effects. The faster-acting phentolarmine appears to be less effective and to have a shorter duration of action than sildenafil. Oral sildenafil is effective in about 70% of men who take it, whereas an adequate response with phentolamine is observed in only 35–40% of patients. Both compounds require erotic stimulation for efficacy. Since sildenafil indirectly increases blood flow in the systemic circulation by enhancing the smooth muscle relaxation effects of nitric oxide, it is contraindicated for patients with unstable heart conditions or cardiovascular disease, in particular patients taking nitrates, such as nitroglycerin, to treat angina. Other adverse effects associated with the clinical use of sildenafil include headache, flushing, dyspepsia, and "abnormal vision," the latter the result of inhibition of the type VI phosphodiesterase isozyme (PDE-VI), a cyclic-GMP-specific phosphodiesterase that is concentrated in the retina. "Abnormal vision" is defined as a mild and transient "bluish" tinge to vision, but also an increased sensitivity to light or blurred vision.

Synthetic melanocortin receptor agonists (melanotropic peptides) have been found to initiate erections in men with psychogenic erectile dysfunction [See H. Wessells et al., "Synthetic Melanotropic Peptide Initiates Erections in Men With Psychogenic Erectile Dysfunction: Double-Blind, Placebo Controlled Crossover Study," *J. Urol.,* 160: 389–393 (1998); *Fifteenth American Peptide Symposium,* Jun. 14–19, 1997 (Nashville Tenn.)]. Activation of melanocortin receptors of the brain appears to cause normal stimulation of sexual arousal. In the above study, the centrally acting α-melanocyte-stimulating hormone analog, melanotan-II (MT-II), exhibited a 75% response rate, similar to results obtained with apomorphine, when injected intramuscularly or subcutaneously to males with psychogenic erectile dysfunction. MT-II is a synthetic cyclic heptapeptide, Ac-Nle-c[Asp-His-DPhe-Arg-Trp-Lys]-NH$_2$, which contains the 4–10 melanocortin receptor binding region common to α-MSH and adrenocorticotropin, but with a lactam bridge. It is a non-selective MC-1R, -3R, -4R, and -5R agonist (Dorr et al., *Life Sciences,* Vol. 58, 1777–1784, 1996). MT-II (also referred to as PT-14) (Erectide®) is presently in clinical development by Palatin Technologies, Inc. and TheraTech, Inc. as a non-penile subcutaneous injection formulation. It is considered to be an "initiator" of the sexual response. The time to onset of erection with this drug is relatively short (10–20 minutes) with a duration of action approximately 2.5 hours. Adverse reactions observed with MT-II include nausea, flushing, loss of appetite, stretching, and yawning and may be the result of activation of MC-1R; MC-2R, MC-3R, and/or MC-5R. MT-II must be administered parenterally, such as by subcutaneous, intravenous, or intramuscular route, since it is not absorbed into the systemic circulation when given by the oral route. Compositions of melanotropic peptides and methods for the treatment of psychogenic erectile dysfunction are disclosed in U.S. Pat. No. 5,576,290, assigned to Competitive Technologies. Methods of stimulating sexual response in females using melanotropic peptides have been disclosed in U.S. Pat. No. 6,051,555.

A series of spiropiperidine derivatives has been disclosed in WO 99/64002 (published Dec. 16, 1999) as agonists of the melanocortin receptor(s) and thereby useful for the treatment of diseases and disorders, such as obesity, diabetes, and sexual dysfunction, including erectile dysfunction and female sexual dysfunction.

Because of the unresolved deficiencies of the various pharmacological agents discussed above, there is a continuing need in the medical arts for improved methods and compositions to treat individuals suffering from psychogenic and/or organic erectile dysfunction. Such methods should have wider applicability, enhanced convenience and ease of compliance, short onset of action, reasonably long duration of action, and minimal side effects with few contraindications, as compared to agents now available.

It is therefore an object of the present invention to provide compounds which are melanocortin receptor agonists and thereby useful to treat obesity, diabetes, and male and/or female sexual dysfunction.

It is another object of the present invention to provide compounds which are selective agonists of the melanocortin-4 (MC-4R) receptor.

It is another object of the present invention to provide pharmaceutical compositions comprising the compounds which are melanocortin receptor agonists.

It is another object of the present invention to provide methods for the treatment or prevention of disorders, diseases, or conditions responsive to the activation of the melanocortin receptor in a subject in need thereof by administering the compounds and pharmaceutical compositions of the present invention.

It is another object of the present invention to provide compounds and pharmaceutical compositions useful for the treatment or prevention of obesity, diabetes mellitus, and male and/or female sexual dysfunction.

It is another object of the present invention to provide compounds and pharmaceutical compositions for the treatment or prevention of erectile dysfunction.

It is another object of the present invention to provide methods for the treatment or prevention of obesity, diabetes mellitus, and male and/or female sexual dysfunction.

These and other objects will become readily apparent from the detailed description that follows.

SUMMARY OF THE INVENTION

The present invention relates to novel 4-substituted piperidines of structural formula I:

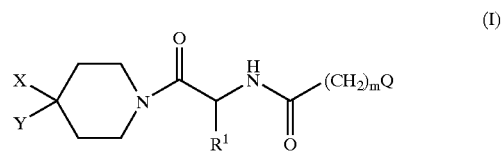

(I)

wherein
Q is

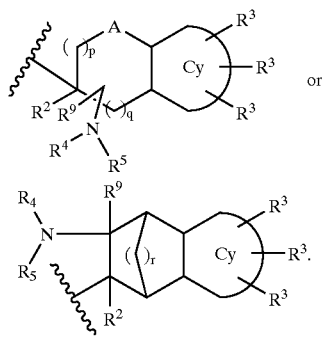

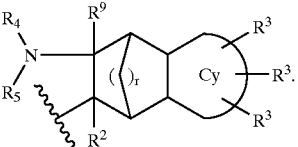

These piperidine derivatives are effective as melanocortin receptor agonists and are particularly effective as selective melanocortin-4 receptor (MC-4R) agonists. They are therefore useful for the treatment and/or prevention of disorders responsive to the activation of MC-4R, such as obesity, diabetes as well as male and/or female sexual dysfunction, in particular, male erectile dysfunction.

The present invention also relates to pharmaceutical compositions comprising the compounds of the present invention and a pharmaceutically acceptable carrier.

The present invention also relates to methods for the treatment or prevention of disorders, diseases, or conditions responsive to the activation of the melanocortin receptor in a subject in need thereof by administering the compounds and pharmaceutical compositions of the present invention.

The present invention also relates to methods for the treatment or prevention of obesity, diabetes mellitus, and male and/or female sexual dysfunction by administering the compounds and pharmaceutical compositions of the present invention.

The present invention also relates to methods for treating erectile dysfunction by administering the compounds and pharmaceutical compositions of the present invention.

The present invention also relates to methods for treating erectile dysfunction by administering the compounds of the present invention in combination with a therapeutically effective amount of another agent known to be useful to treat the condition.

The present invention also relates to methods for treating or preventing obesity by administering the compounds of the present invention in combination with a therapeutically effective amount of another agent known to be useful to treat the condition.

DETAILED DESCRIPTION OF THE INVENTION

The present invention relates to 4-substituted piperidines useful as melanocortin receptor agonists, in particular, as selective MC-4R agonists. Representative compounds of the present invention are described by structural formula (I):

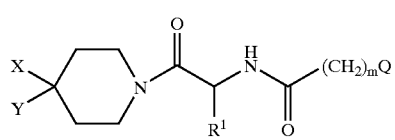

(I)

wherein
Q is

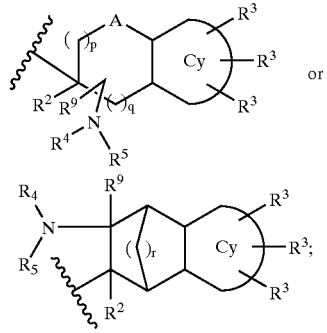

Cy is selected from the group consisting of
  aryl,
  5- or 6-membered heteroaryl,
  5- or 6-membered heterocyclyl, and
  5- to 7-membered carbocyclyl;
  wherein Cy is substituted with one to three groups independently selected from $R^3$;
A is O, $S(O)_m$, $NR^7$, or $CH_2$;
m is 0, 1, or 2;
n is 0, 1, 2, or 3;
p is 0, 1 or 2;
q is 0, 1 or 2;
r is 1, 2, or 3;
$R^1$ is selected from the group consisting of
  hydrogen,
  $C_{1-8}$ alkyl,
  $(CHR^7)_n$—$C_{3-7}$ cycloalkyl,
  $(CHR^7)_n$aryl, and
  $(CHR^7)_n$heteroaryl;
    in which aryl and heteroaryl are unsubstituted or substituted with one to three groups independently selected from $R^6$; and alkyl and cycloalkyl are unsubstituted or substituted with one to three groups independently selected from $R^6$ and oxo;
$R^2$ is selected from the group consisting of
  hydrogen,
  $C_{1-8}$ alkyl,
  $(CH_2)_nC_{3-7}$ cycloalkyl, and
  $(CH_2)_n$-aryl;
each $R^3$ is independently selected from
  hydrogen,
  $C_{1-8}$ alkyl,
  $(CH_2)_n$-aryl,
  $(CH_2)_nC_{3-7}$ cycloalkyl,
  $(CH_2)_n$-heteroaryl,
  halo,
  $OR^7$,
  $NHSO_2R^7$,
  $N(R^7)_2$,
  $C\equiv N$,
  $CO_2R^7$,
  $C(R^7)(R^7)N(R^7)_2$,
  $NO_2$,
  $SO_2N(R^7)_2$,
  $S(O)_mR^7$,
  $CF_3$, and
  $OCF_3$;
$R^4$ and $R^5$ are each independently selected from the group consisting of
  hydrogen,
  $C_{1-10}$ alkyl, and
  $C_{3-8}$ cycloalkyl;

or $R^4$ and $R^5$ together with the nitrogen to which they are attached form a 5- to 8-membered ring optionally containing an additional heteroatom selected from O, S, and $NR^7$;
  wherein alkyl and cycloalkyl are unsubstituted or substituted with one to three groups independently selected from $R^6$ and oxo;
    $R^6$ is selected from the group consisting of
      $C_{1-8}$ alkyl,
      $(CH_2)_n$-aryl,
      $(CH_2)_n C_{3-7}$ cycloalkyl,
      $(CH_2)_n$-heteroaryl,
      halo,
      $OR^7$,
      $NHSO_2R^7$,
      $N(R^7)_2$,
      $C\equiv N$,
      $CO_2R^7$,
      $C(R^7)(R^7)N(R^7)_2$,
      $NO_2$,
      $SO_2N(R^7)_2$,
      $S(O)_m R^7$,
      $CF_3$, and
      $OCF_3$;
    each $R^7$ is independently selected from the group consisting of
      hydrogen,
      $C_{1-8}$ alkyl,
      $(CH_2)_n$-aryl, and
      $(CH_2)_n C_{3-7}$ cycloalkyl;
    each $R^8$ is independently selected from the group consisting of
      hydrogen,
      $C_{1-8}$alkyl,
      $(CH_2)_n$-aryl,
      $(CH_2)_n$-heteroaryl, and
      $(CH_2)_n C_{3-7}$ cycloalkyl;
      wherein aryl and heteroaryl are unsubstituted or substituted with one to three groups independently selected from $R^6$; and alkyl, cycloalkyl, and $(CH_2)_n$ are unsubstituted or substituted with one to three groups independently selected from $R^6$ and oxo; or two $R^8$ groups together with the atoms to which they are attached form a 5- to 8-membered mono or bi-cyclic ring system optionally containing an additional heteroatom selected from O, S, and $NR^7$;
X is selected from the group consisting of
  $C_{1-8}$ alkyl,
  $(CH_2)_n C_{3-8}$ cycloalkyl,
  $(CH_2)_n$aryl,
  $(CH_2)_n$heteroaryl,
  $(CH_2)_n$heterocyclyl,
  $(CH_2)_n C\equiv N$,
  $(CH_2)_n CON(R^8 R^8)$,
  $(CH_2)_n CO_2 R^8$,
  $(CH_2)_n COR^8$
  $(CH_2)_n NR^8 C(O)R^8$,
  $(CH_2)_n NR^8 CO_2 R^8$,
  $(CH_2)_n NR^8 C(O)N(R^8)_2$,
  $(CH_2)_n NR^8 SO_2 R^8$,
  $(CH_2)_n S(O)_m R^8$,
  $(CH_2)_n SO_2 N(R^8)(R^8)$,
  $(CH_2)_n OR^8$,
  $(CH_2)_n OC(O)R^8$,
  $(CH_2)_n OC(O)OR^8$,
  $(CH_2)_n OC(O)N(R^8)_2$,
  $(CH_2)_n N(R^8)(R^8)$, and
  $(CH_2)_n NR^8 SO_2 N(R^8)(R^8)$;
    wherein aryl and heteroaryl are unsubstituted or substituted with one to three groups selected from $R^6$; and alkyl, $(CH_2)_n$, cycloalkyl, and heterocyclyl are unsubstituted or substituted with one to four groups independently selected from $R^6$ and oxo;
Y is selected from the group consisting of
  hydrogen,
  $C_{1-8}$ alkyl,
  $(CH_2)_n C_{3-8}$ cycloalkyl,
  $(CH_2)_n$aryl,
  $(CH_2)_n$heterocyclyl, and
  $(CH_2)_n$heteroaryl;
    wherein aryl and heteroaryl are unsubstituted or substituted with one to three groups selected from $R^6$, and alkyl, $(CH_2)_n$, cycloalkyl, and heterocyclyl are optionally substituted with one to three groups selected from $R^6$ and oxo;
or a pharmaceutically acceptable salt thereof.

In one embodiment of the compounds of formula I, Cy is selected from the group consisting of benzene, pyridine, pyrazine, piperidine, and cyclohexane. In a class of this embodiment, Cy is benzene or cyclohexane; in a subclass of this class, Cy is benzene.

In another embodiment of the compounds of formula I, $R^1$ is $CH(R^7)$-aryl or $CH(R^7)$-heteroaryl wherein aryl and heteroaryl are optionally substituted with one or two $R^6$ groups. In a class of this embodiment, $R^1$ is benzyl optionally substituted with one or two groups selected from halogen, $C_{1-4}$ alkyl, $C_{1-4}$ alkoxy, $CF_3$, and $OCF_3$. In a subclass of this class, $R^1$ is 4-chlorobenzyl, 4-fluorobenzyl, or 4-methoxybenzyl.

In a third embodiment of compounds of formula I, $R^2$ is H or $CH_3$.

In a fourth embodiment of compounds of formula I, X is $(CH_2)_n$-aryl, $(CH_2)_n$-heteroaryl, $(CH_2)_n$-heterocyclyl, $(CH_2)C(O)N(R^8)(R^8)$, $(CH_2)_n CO_2 R^8$, $(CH_2)_n OR^8$, $(CH_2)_n NR^8 C(O)R^8$, or $(CH2)nNR^8 SO_2 R^8$, wherein aryl and heteroaryl are optionally substituted with one to three groups selected from $R^6$; heterocyclyl is optionally substituted with one to three groups selected from $R^6$ and oxo; and the $(CH_2)_n$ group is optionally substituted with one to three groups selected from $R^7$, halo, $S(O)_m R^7$, $N(R^7)_2$, and $OR^7$. In a class of this embodiment, X is $CH_2$-heteroaryl, $CH_2$-heterocyclyl, NHC$(O)R^8$, $CO_2 R^8$, or $C(O)N(R^8)(R^8)$, wherein heteroaryl is optionally substituted with one to three groups selected from $R^6$; heterocyclyl is optionally substituted with one to three groups selected from $R^6$ and oxo; and wherein $R^8$ is each independently selected from H and $C_{1-6}$ alkyl optionally substituted with $OR^7$, $SR^7$, or $N(R^7)_2$, or 2 $R^7$ groups together with the nitrogen to which they are attached form a 5- or 6-membered ring optionally having an additional heteroatom selected from O, S and $NR^7$. In a subclass of this class, heteroaryl is selected from the group consisting of pyridyl, pyrazinyl, pynmidinyl, triazolyl, tetrazolyl, thiadiazolyl, oxadiazolyl, pyrazolyl, and imidazolyl.

In a fifth embodiment of compounds of formula I, Y is $C_{1-8}$ alklyl, $(CH_2)_n C_{5-7}$ cycloalkyl, $(CH_2)_n$-aryl, $(CH_2)_n$-heterocyclyl or $(CH_2)_n$-heteroaryl, wherein aryl and heteroaryl are optionally substituted with one to three groups selected from $R^6$; and $(CH_2)_n$, alkyl, cycloalkyl, and heterocyclyl are optionally substituted with one to three groups selected from $R^6$ and oxo. In a class of this embodiment, Y is cyclohexyl, cycloheptyl, cyclopentyl, phenyl, or $C_{1-6}$ alkyl, unsubstituted or substituted with one to three groups selected from $R^6$ and oxo. In a subclass of this class, Y is cyclohexyl or $C_{1-6}$ alkyl, wherein the cyclohexyl and alkyl groups are unsubstituted or substituted with one to three groups selected from $R^6$ and oxo.

In a sixth embodiment of compounds of formula I, q is 1 and p is 0, 1, or 2; in a class of this embodiment, p and q are both 1.

In a yet a further embodiment there are provided compounds of formula Ia:

(Ia)

wherein

Cy is phenyl or cyclohexyl,
wherein Cy is substituted with one to three groups independently selected from $R^3$;
n is 0 or 1;
p is 0, 1, or 2;
$R^2$ is selected from the group consisting of
  hydrogen,
  $C_{1-6}$ alkyl, and
  $C_{5-6}$ cycloalkyl;
each $R^3$ is independently selected from
  hydrogen,
  $C_{1-8}$ alkyl,
  $(CH_2)_n$-aryl,
  $(CH_2)_nC_{3-7}$ cycloalkyl,
  $(CH_2)_n$-heteroaryl,
  halo,
  $OR^7$,
  $NHSO_2R^7$,
  $N(R^7)_2$,
  $C\equiv N$,
  $CO_2R^7$,
  $C(R^7)(R^7)N(R^7)_2$,
  $NO_2$,
  $SO_2N(R^7)_2$,
  $S(O)_mR^7$,
  $CF_3$, and
  $OCF_3$;
$R^4$ and $R^5$ are each independently selected from the group consisting of
  hydrogen,
  $C_{1-6}$ alkyl, and
  $C_{5-6}$ cycloalkyl;
or $R^4$ and $R^5$ together with the nitrogen to which they are attached form a 5- to 8-membered ring, optionally containing an additional heteroatom selected from O, S, and $NR^7$;
  wherein alkyl and cycloalkyl are unsubstituted or substituted with one to three groups independently selected from $R^6$ and oxo;

$R^6$ is selected from the group consisting of
  $C_{1-8}$ alkyl,
  $(CH_2)_n$-aryl,
  $(CH_2)_nC_{3-7}$cycloalkyl,
  $(CH_2)_n$-heteroaryl,
  halo,
  $OR^7$,
  $NHSO_2R^7$,
  $N(R^7)_2$,
  $C\equiv N$,
  $CO_2R^7$,
  $C(R^7)(R^7)N(R^7)_2$,
  $NO_2$,
  $SO_2N(R^7)_2$,
  $S(O)_mR^7$,
  $CF_3$, and
  $OCF_3$;
    each $R^7$ is independently selected from the group consisting of
      hydrogen,
      $C_{1-8}$ alky, and
      $C_{3-6}$ cycloalkyl;
    each $R^8$ is independently selected from the group consisting of
      hydrogen,
      $C_{1-5}$ alkyl,
      aryl,
      heteroaryl, and
      $C_{5-6}$cycloalkyl;
    wherein aryl and heteroaryl are unsubstituted or substituted with one to three groups independently selected from $R^6$; and alkyl and cycloalkyl are unsubstituted or substituted with one to three groups independently selected from $R^6$ and oxo; or two $R^8$ groups together with the atoms to which they are attached form a 5- to 8-membered mono- or bi-cyclic ring optionally containing an additional heteroatom selected from O, S, and $NR^7$;

X is selected from the group consisting of
  $C_{1-8}$ alkyl,
  $(CH_2)_nC_{3-8}$cycloalkyl,
  $(CH_2)_n$aryl,
  $(CH_2)_n$heteroaryl,
  $(CH_2)_n$heterocyclyl,
  $(CH_2)_nC\equiv N$,
  $(CH_2)_nCON(R^8R^8)$,
  $(CH_2)_nCO_2R^8$,
  $(CH_2)_nCOR^8$,
  $(CH_2)_nNR^8C(O)R^8$,
  $(CH_2)_nNR^8CO_2R^8$,
  $(CH_2)_nNR^8C(O)N(R^8)_2$,
  $(CH_2)_nNR^8SO_2R^8$,
  $(CH_2)_nS(O)mR^8$,
  $(CH_2)_nSO_2N(R^8)(R^8)$,
  $(CH_2)_nOR^8$,
  $(CH_2)_nOC(O)R^8$,
  $(CH_2)_nOC(O)OR^8$,
  $(CH_2)_nOC(O)N(R^8)_2$,
  $(CH_2)_nN(R^8)(R^8)$, and
  $(CH_2)_nNR^8SO_2N(R^8)(R^8)$;
    wherein aryl and heteroaryl are unsubstituted or substituted with one to three groups selected from $R^6$; and alkyl, $(CH_2)_n$, cycloalkyl, and heterocyclyl are unsubstituted or substituted with one to four groups independently selected from $R^6$ and oxo;

Y is selected from the group consisting of
hydrogen,
$C_{1-8}$ alkyl,
$(CH_2)_n C_{3-6}$ cycloalkyl,
$(CH_2)_n$ aryl, and
$(CH_2)_n$ heteroaryl;
wherein aryl and heteroaryl are unsubstituted or substituted with one to three groups selected from $R^6$; and alkyl, $(CH_2)_n$, and cycloalkyl are unsubstituted or substituted with one to three groups selected from $R^6$ and oxo; or a pharmaceutically acceptable salt thereof.

In an embodiment of the compounds of formula Ia, the carbon atom marked with * has the R configuration.

In a second embodiment of compounds of formula Ia, X is selected from the group consisting of:

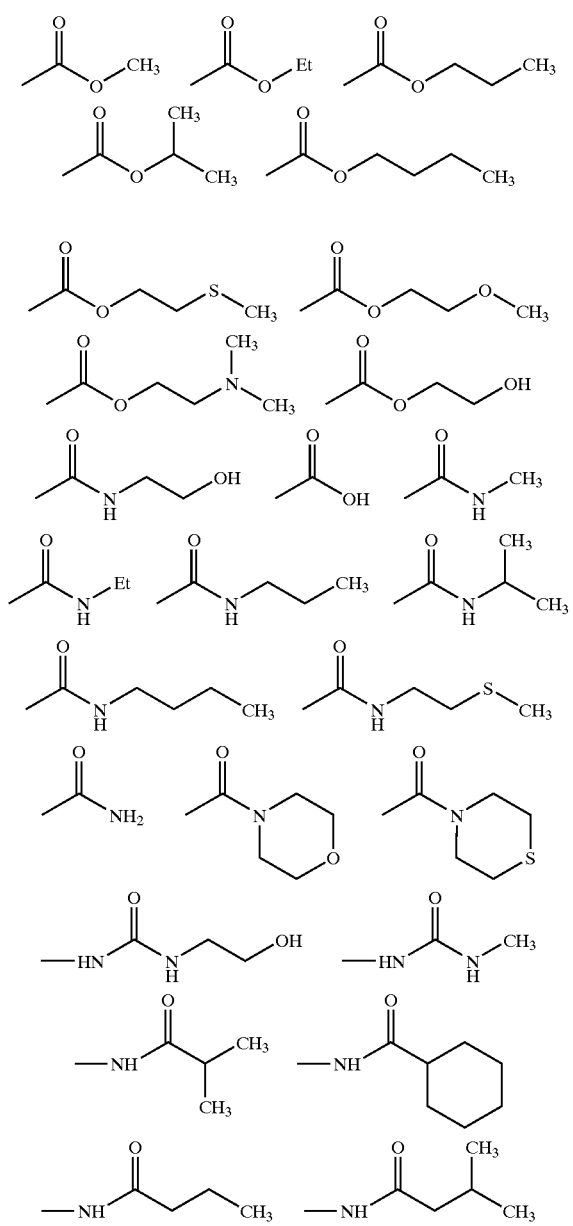

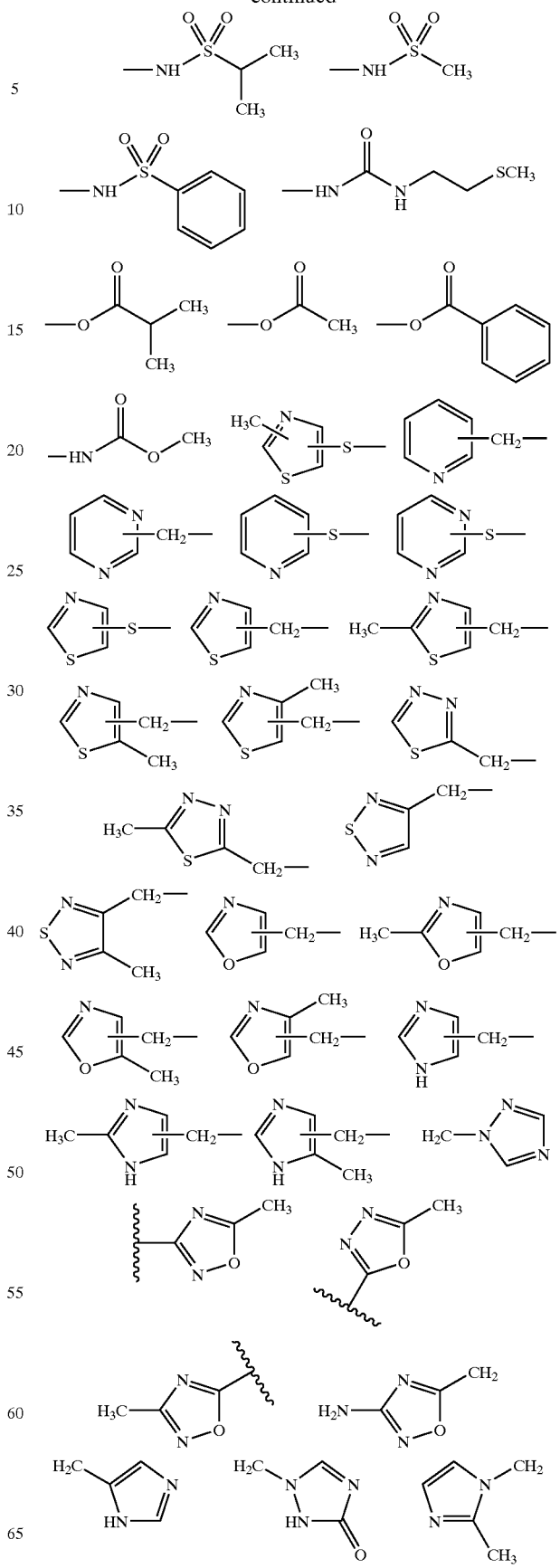

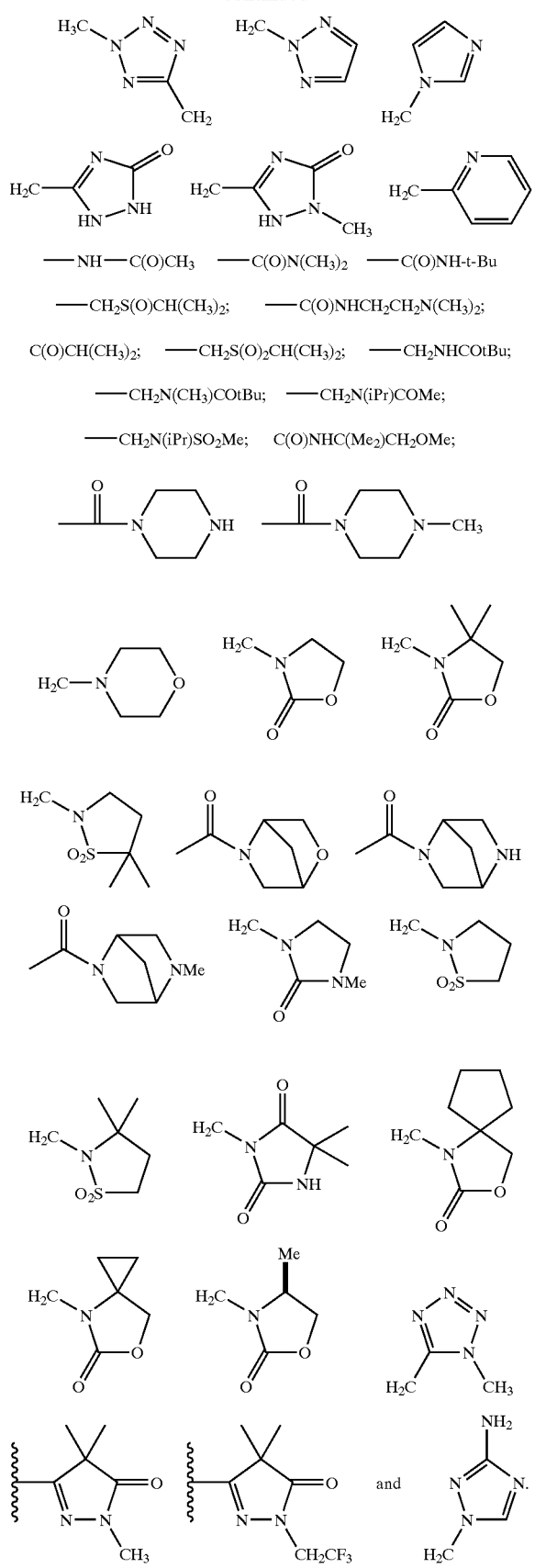
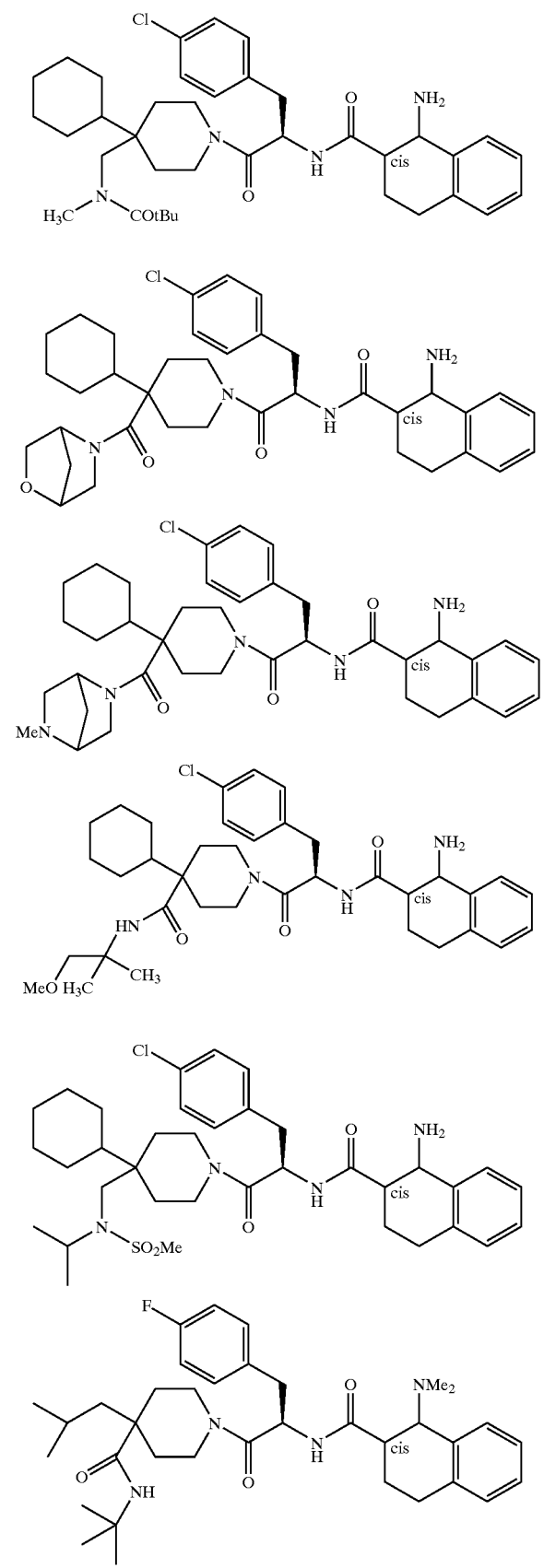
Representative compounds of formula Ia are as follows:

-continued
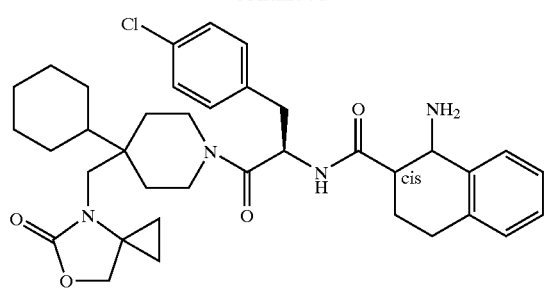
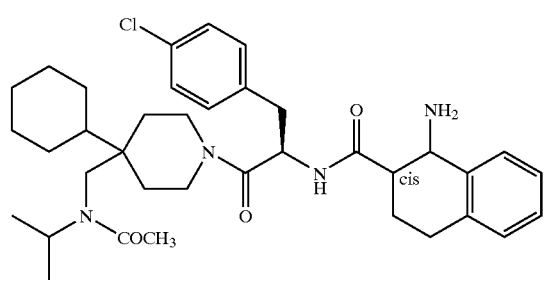
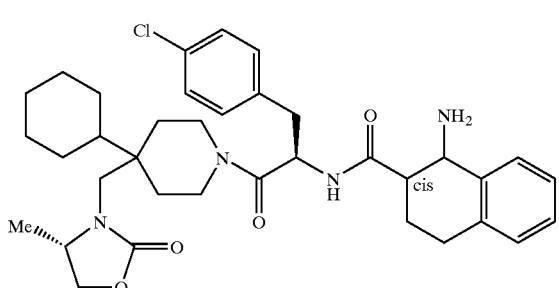
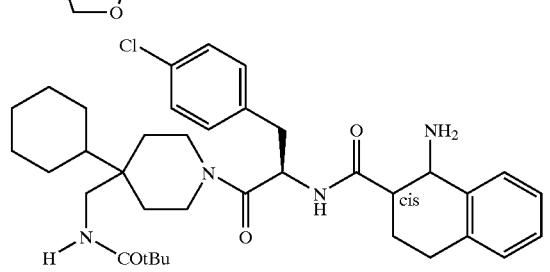
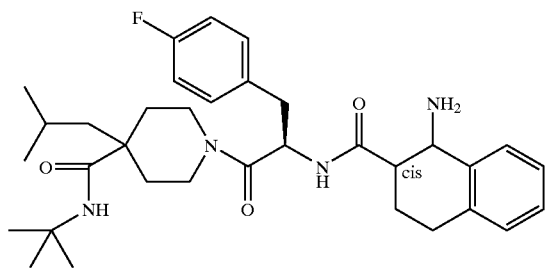
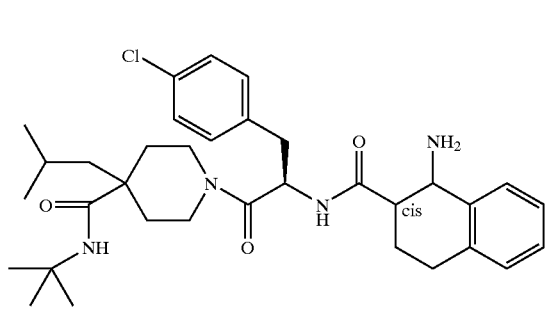
-continued
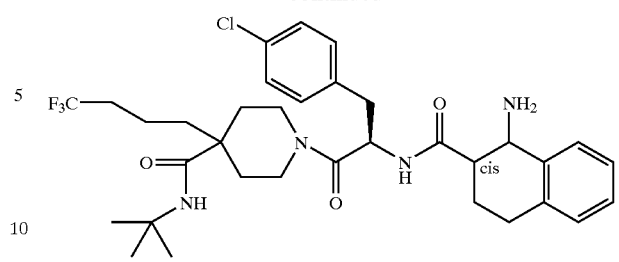
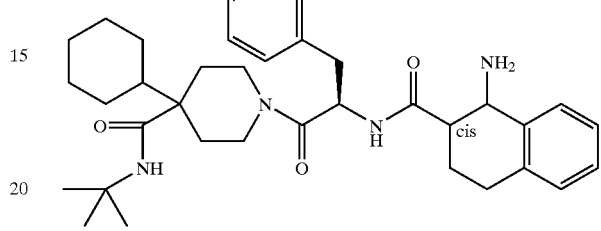
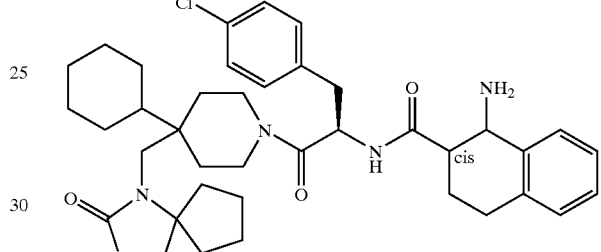
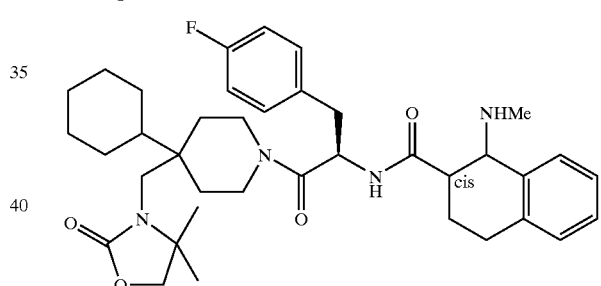
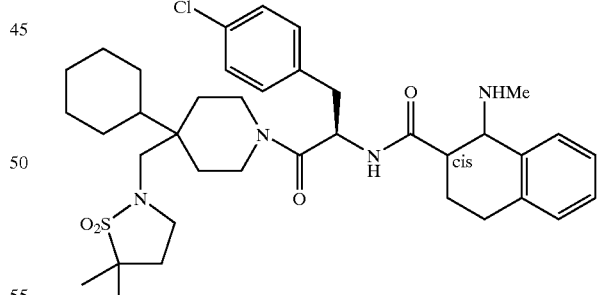
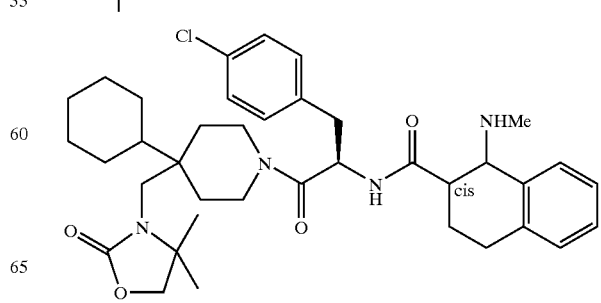

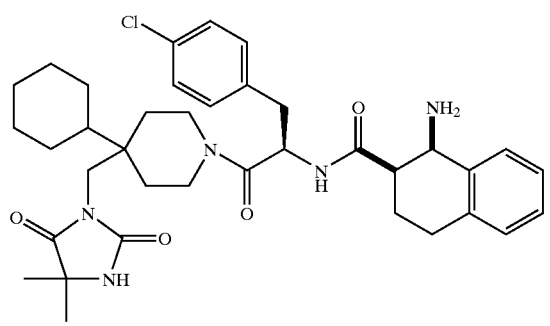
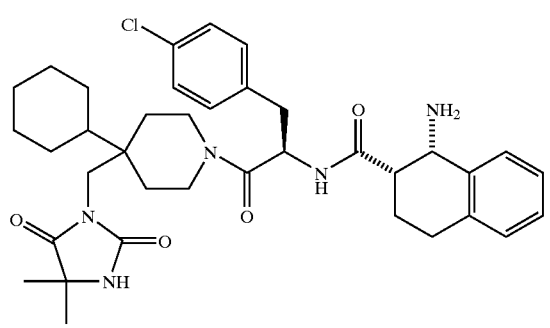
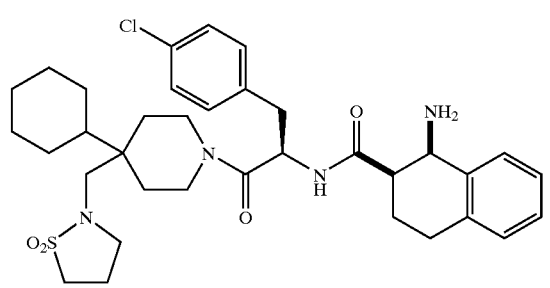
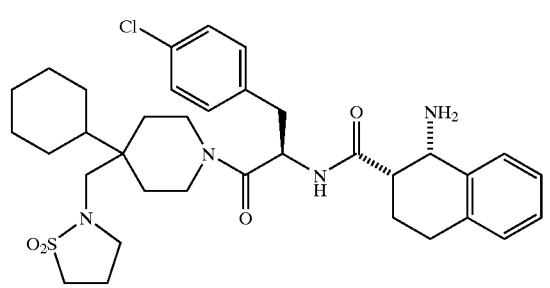
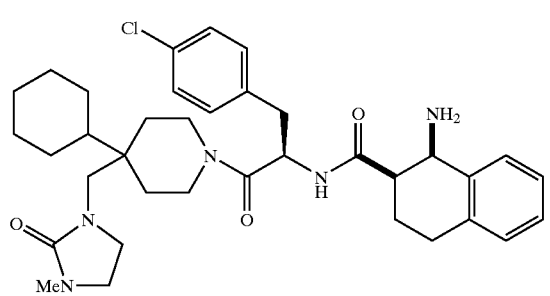
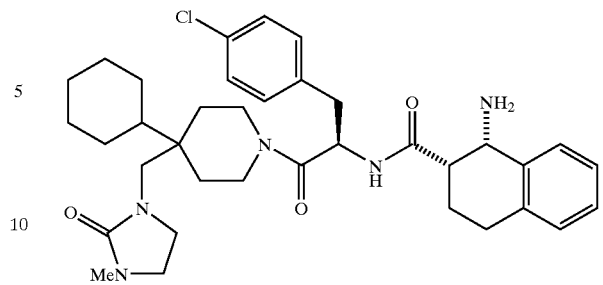
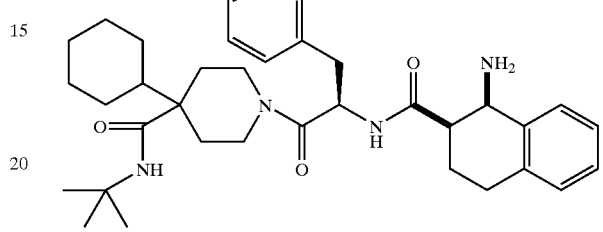
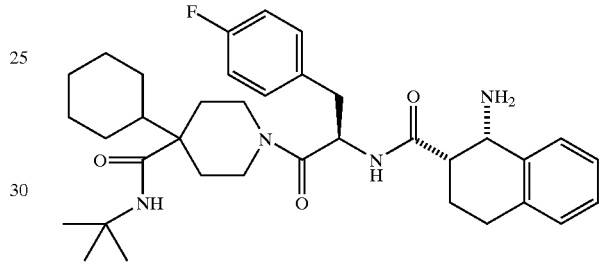
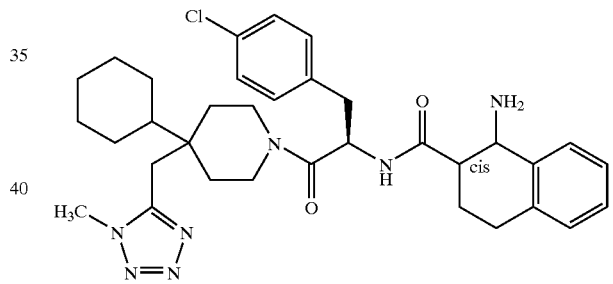
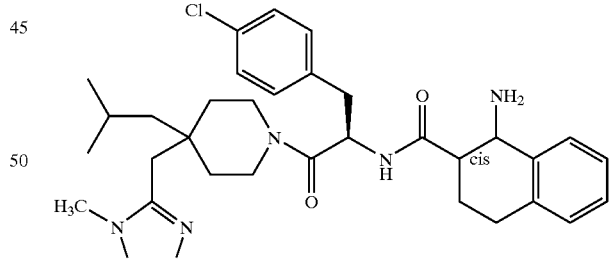
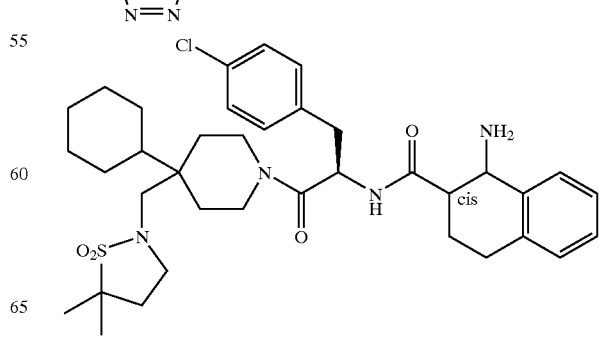

-continued
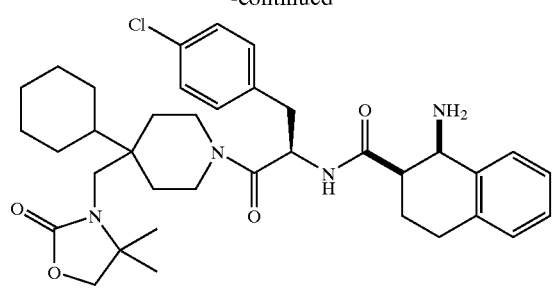
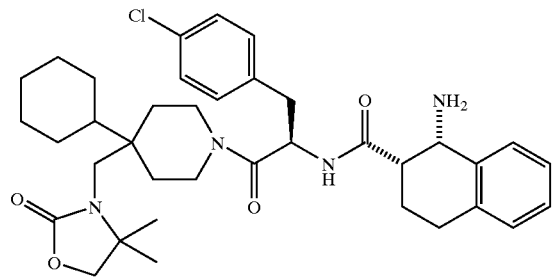
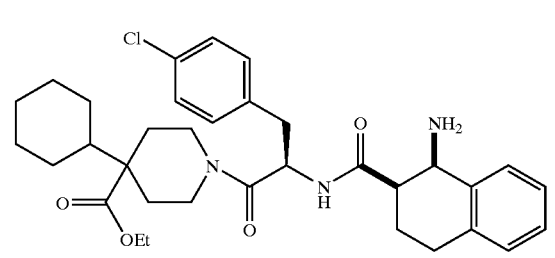
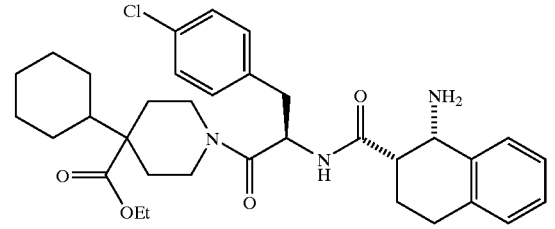
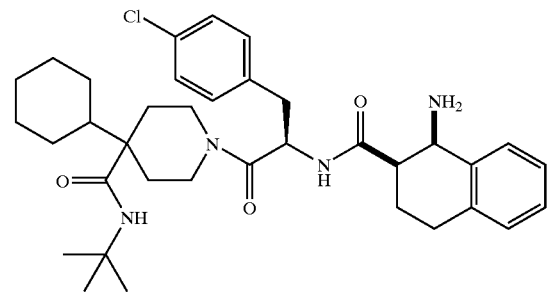
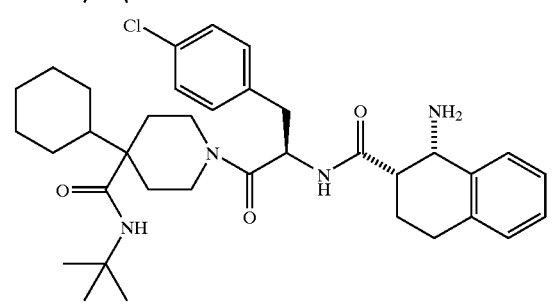
-continued
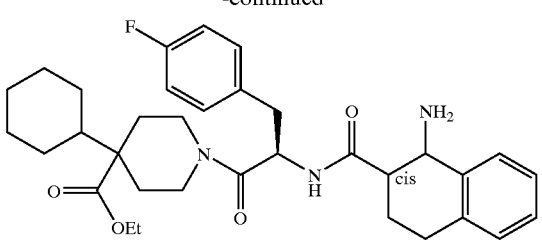
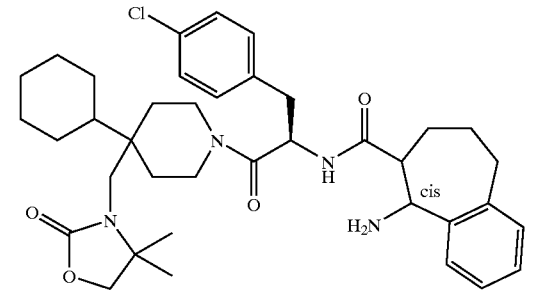
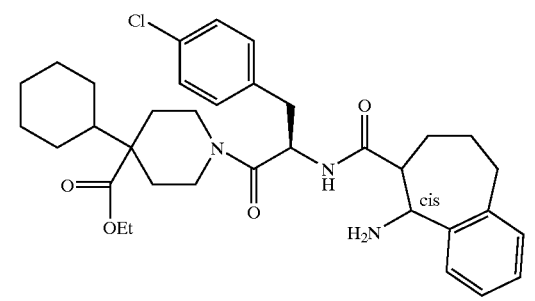
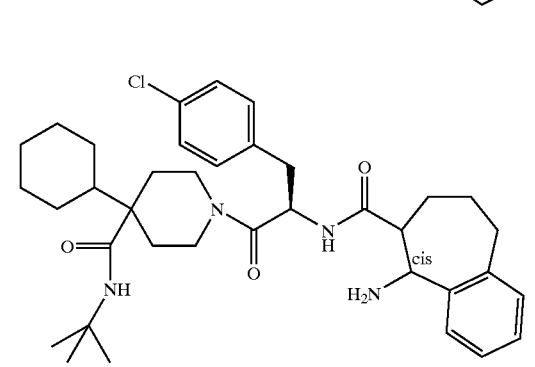
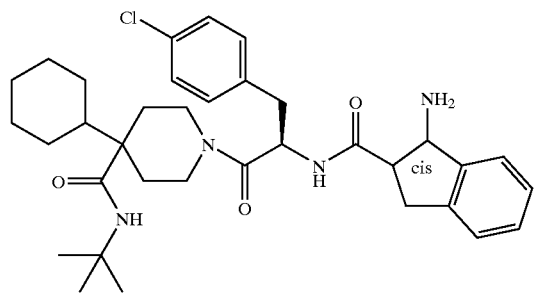
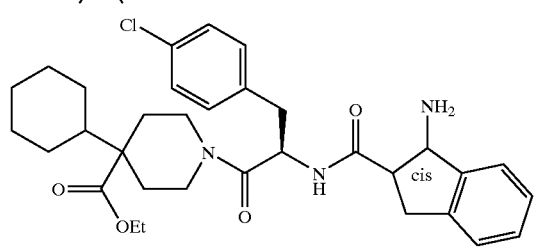

-continued

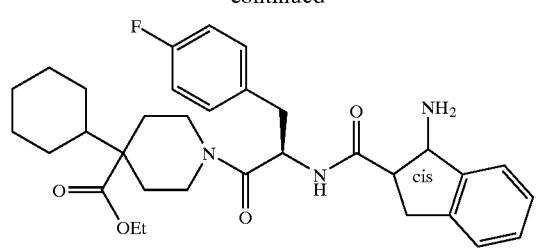
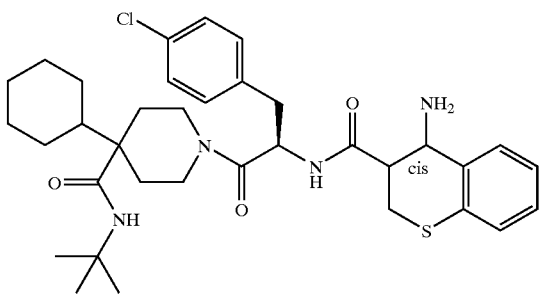
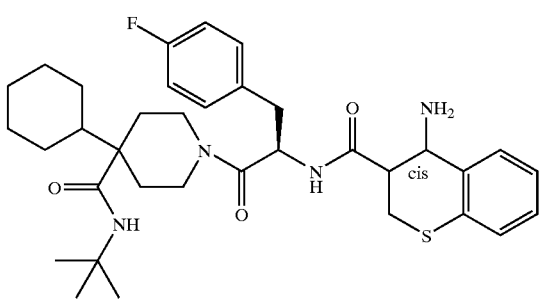
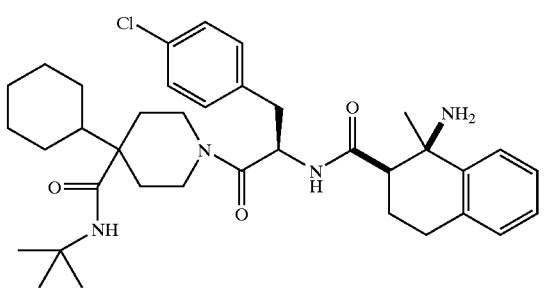
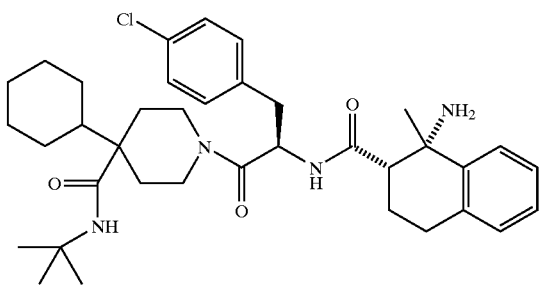
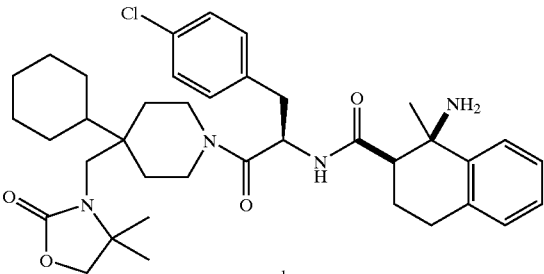

and

-continued

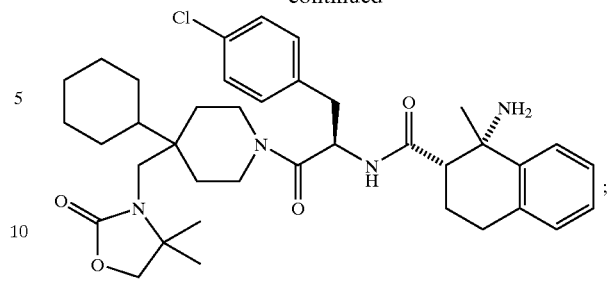

or a pharmaceutically acceptable salt thereof.

In a yet a further embodiment of the compounds of the present invention, there are provided compounds of formula Ib:

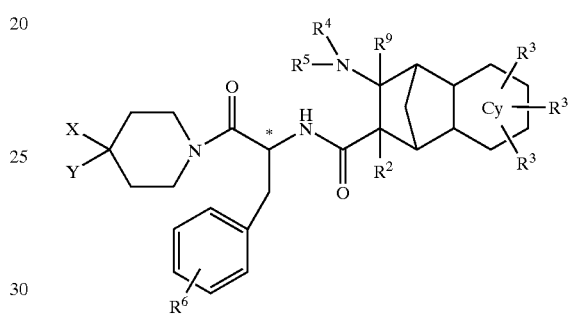

(Ib)

wherein
Cy is phenyl or cyclohexyl,
  wherein Cy is substituted with one to three groups independently selected from $R^3$;
n is 1 or 2;
$R^2$ is selected from the group consisting of
  hydrogen,
  $C_{1-6}$ alkyl, and
  $C_{5-6}$ cycloalkyl;
each $R^3$ is independently selected from
  hydrogen,
  $C_{1-8}$ alkyl,
  $(CH_2)_n$-aryl,
  $(CH_2)_nC_{3-7}$ cycloalkyl,
  $(CH_2)_n$-heteroaryl,
  halo,
  $OR^7$,
  $NHSO_2R^7$,
  $N(R^7)_2$,
  $C\equiv N$,
  $CO_2R^7$,
  $C(R^7)(R^7)N(R^7)_2$,
  $NO_2$,
  $SO_2N(R^7)_2$,
  $S(O)_mR^7$,
  $CF_3$, and
  $OCF_3$;
$R^4$ and $R^5$ are each independently selected from the group consisting of
  hydrogen,
  $C_{1-6}$ alkyl, and
  $C_{5-6}$ cycloalkyl;
or $R^4$ and $R^5$ together with the nitrogen to which they are attached form a 5- to 8-membered ring optionally containing an additional heteroatom selected from O, S, and $NR^7$;

wherein alkyl and cycloalkyl are unsubstituted or substituted with one to three groups independently selected from $R^6$ and oxo;

$R^6$ is selected from the group consisting of
$C_{1-8}$ alkyl,
$(CH_2)_n$-aryl,
$(CH_2)_nC_{3-7}$cycloalkyl,
$(CH_2)_n$-heteroaryl,
halo,
$OR^7$,
$NHSO_2R^7$,
$N(R^7)_2$,
$C\equiv N$,
$CO_2R^7$,
$C(R^7)(R^7)N(R^7)_2$,
$NO_2$,
$SO_2N(R^7)_2$,
$S(O)_mR^7$,
$CF_3$, and
$OCF_3$;
  each $R^7$ is independently selected from the group consisting of
    hydrogen,
    $C_{1-8}$ alky, and
    $C_{3-6}$ cycloalkyl;
  each $R^8$ is independently selected from the group consisting of
    hydrogen,
    $C_{1-5}$ alkyl,
    aryl,
    heteroaryl, and
    $C_{5-6}$ cycloalkyl;
  wherein aryl and heteroaryl are unsubstituted or substituted with one to three groups independently selected from $R^6$; and alkyl and cycloalkyl are unsubstituted or substituted with one to three groups independently selected from $R^6$ and oxo; or two
    $R^8$ groups together with the atoms to which they are attached form a 5- to 8-membered mono- or bi-cyclic ring optionally containing an additional heteroatom selected from O, S, and $NR^7$;

$R^9$ is hydrogen or $C_{1-4}$ alkyl;

X is selected from the group consisting of
$C_{1-8}$ alkyl,
$(CH_2)_nC_{3-8}$cycloalkyl,
$(CH_2)_n$aryl,
$(CH_2)_n$heteroaryl,
$(CH_2)_n$heterocyclyl,
$(CH_2)_nC\equiv N$,
$(CH_2)_nCON(R^8R^8)$,
$(CH_2)_nCO_2R^8$,
$(CH_2)_nCOR^8$,
$(CH_2)_nNR^8C(O)R^8$,
$(CH_2)_nNR^8CO_2R^8$,
$(CH_2)_nNR^8C(O)NR^8)_2$,
$(CH_2)_nNR^8SO_2R^8$,
$(CH_2)_nS(O)mR^8$,
$(CH_2)_nSO_2N(R^8)(R^8)$,
$(CH_2)_nOR^8$,
$(CH_2)_nOC(O)R^8$,
$(CH_2)_nOC(O)OR^8$,
$(CH_2)_nOC(O)N(R^8)_2$,
$(CH_2)_nN(R^8)(R^8)$, and
$(CH_2)_nNR^8SO_2N(R^8)(R^8)$;

wherein aryl and heteroaryl are unsubstituted or substituted with one to three groups selected from $R^6$; and alkyl, $(CH_2)_n$, cycloalkyl, and heterocyclyl are unsubstituted or substituted with one to four groups independently selected from $R^6$ and oxo;

Y is selected from the group consisting of
hydrogen,
$C_{1-8}$ alkyl,
$(CH_2)_nC_{3-6}$ cycloalkyl,
$(CH_2)_n$aryl, and
$(CH_2)_n$heteroaryl;
  wherein aryl and heteroaryl are unsubstituted or substituted with one to three groups selected from $R^6$; and alkyl, $(CH_2)_n$, and cycloalkyl are unsubstituted or substituted with one to three groups selected from $R^6$ and oxo; or a pharmaceutically acceptable salt thereof.

In an embodiment of the compounds of formula Ib, the carbon atom marked with * has the R configuration.

In a second embodiment of the compounds of formula Ib, X is selected from the group consisting of:

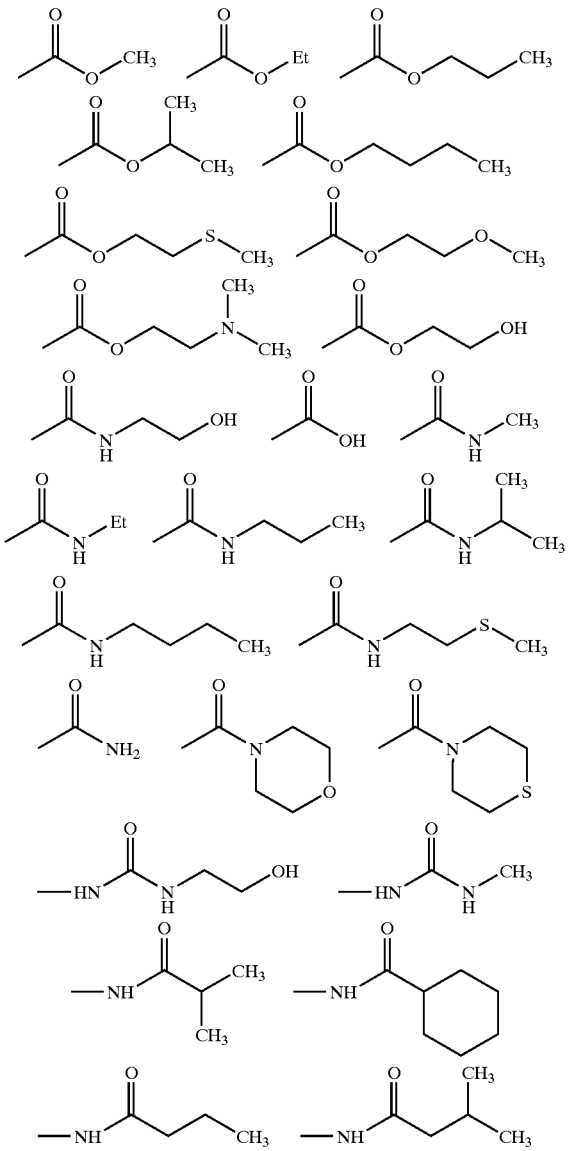

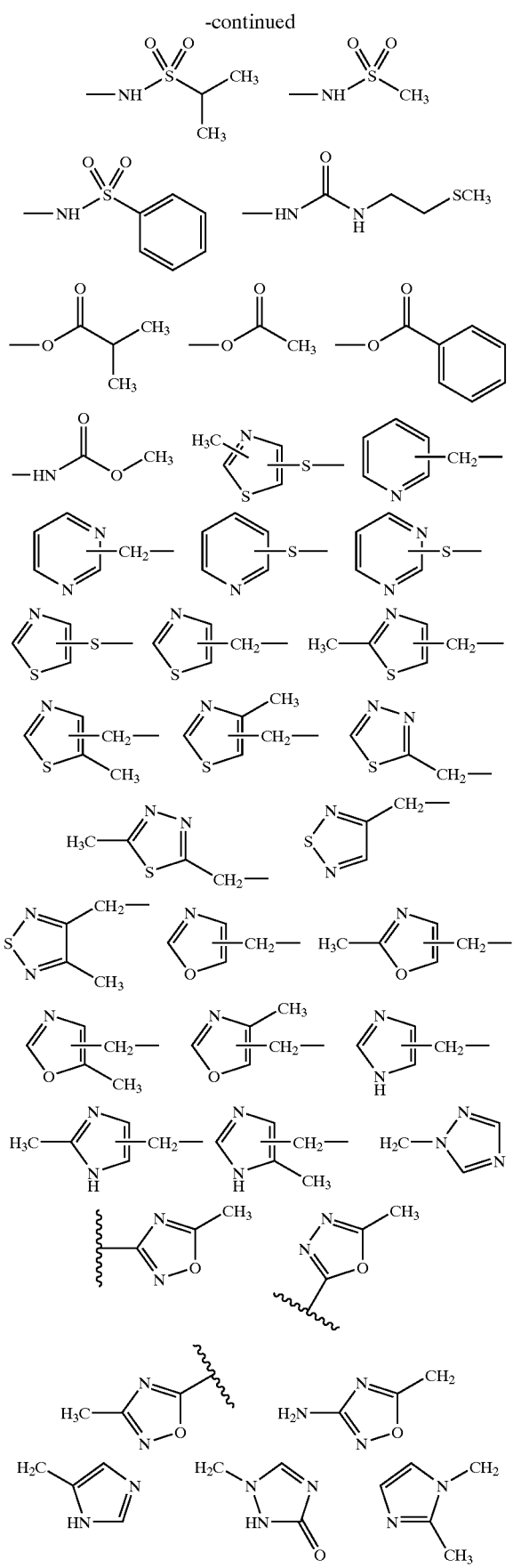
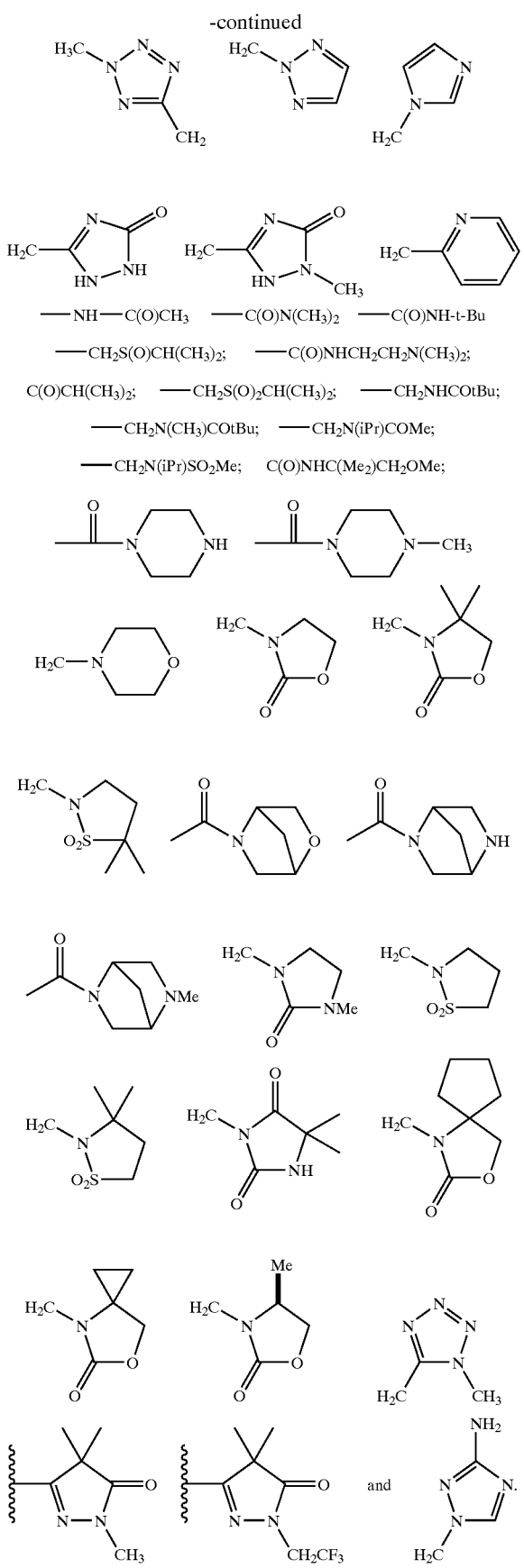

Representative compounds of formula Ib are the following:

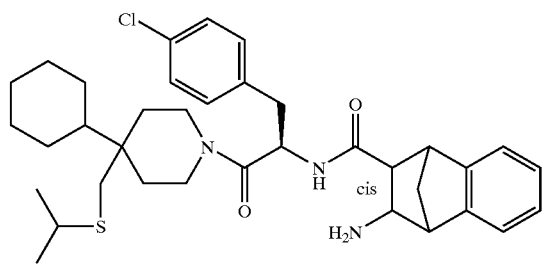
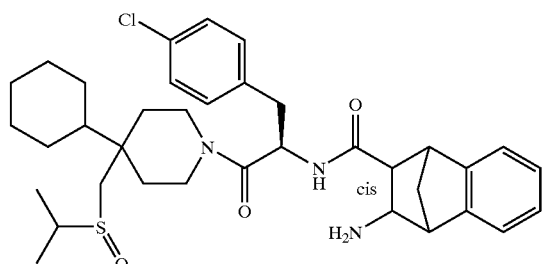
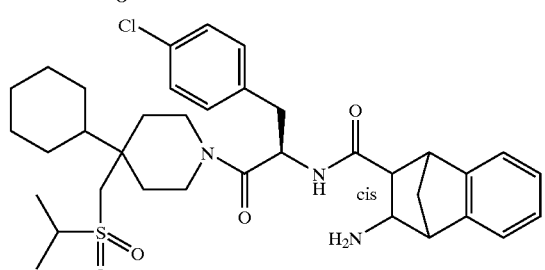
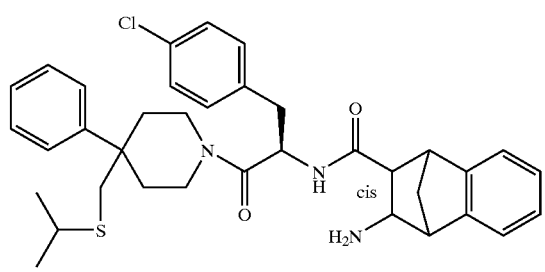
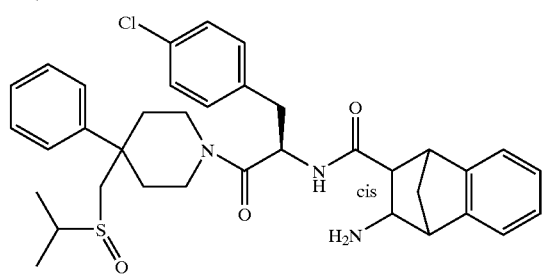
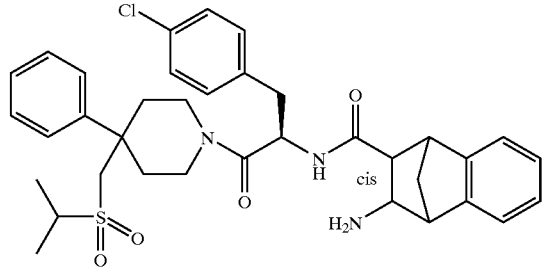
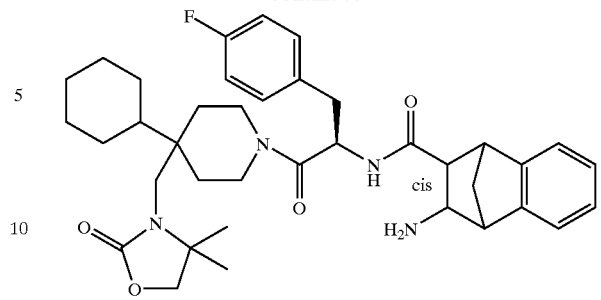
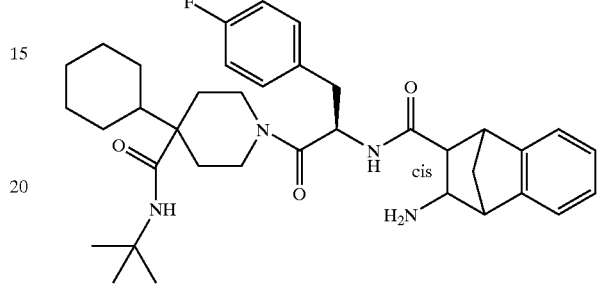
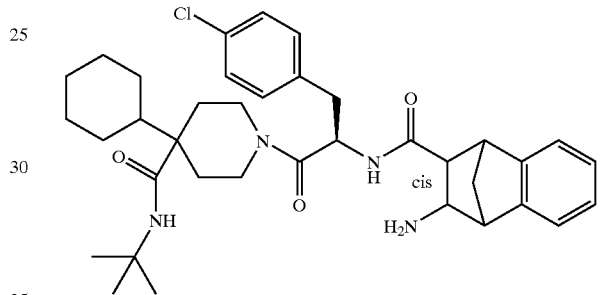
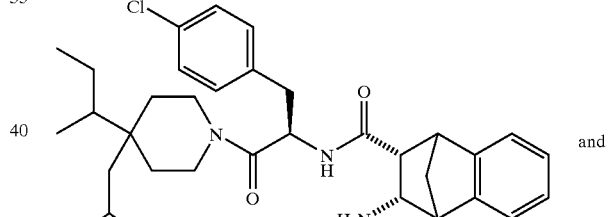
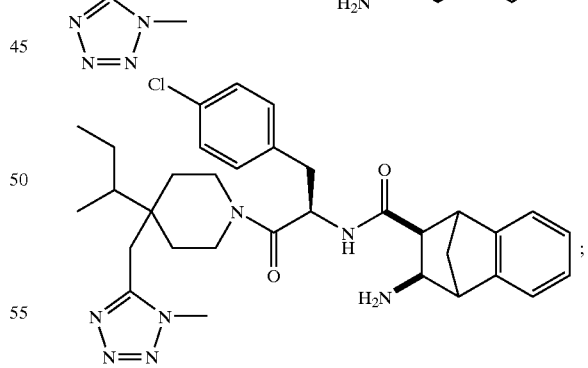

and

;

or a pharmaceutically acceptable salt thereof.

The compounds of structural Formula I are effective as melanocortin receptor agonists and are particularly effective as selective agonists of MC-4R. They are therefore useful for the treatment and/or prevention of disorders responsive to the activation of MC-4R, such as obesity, diabetes as well as male and/or female sexual dysfunction, in particular, erectile dysfunction, and further in particular, male erectile dysfunction.

Another aspect of the present invention provides a method for the treatment or prevention of obesity or diabetes in a subject in need thereof which comprises administering to said subject a therapeutically or prophylactically effective amount of a compound of formula I.

Another aspect of the present invention provides a method for the treatment or prevention of male or female sexual dysfunction including erectile dysfunction which comprises administering to a subject in need of such treatment or prevention a therapeutically or prophylactically effective amount of a compound of formula I.

Another aspect of the present invention provides a pharmaceutical composition comprising a compound of formula I and a pharmaceutically acceptable carrier.

Yet another aspect of the present invention provides a method for the treatment or prevention of male or female sexual dysfunction including erectile dysfunction which comprises administering to a subject in need of such treatment or prevention a therapeutically or prophylactically effective amount of a compound of formula I in combination with a therapeutically effective amount of another agent known to be useful for the treatment of these conditions.

Throughout the instant application, the following terms have the indicated meanings:

The alkyl groups specified above are intended to include those alkyl groups of the designated length in either a straight or branched configuration. Exemplary of such allyl groups are methyl, ethyl, propyl, isopropyl, butyl, sec-butyl, tertiary butyl, pentyl, isopentyl, hexyl, isohexyl, and the like.

The term "halogen" is intended to include the halogen atoms fluorine, chlorine, bromine and iodine.

The term "aryl" includes phenyl and naphthyl.

The term "heteroaryl" includes mono- and bicyclic aromatic rings containing from 1 to 4 heteroatoms selected from nitrogen, oxygen and sulfur. "5- or 6-membered heteroaryl" are monocyclic heteroaromatic rings, examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

The term "5- or 6-membered carbocyclyl" is intended to include non-aromatic rings containing only carbon atoms such as cyclopentyl and cyclohexyl.

The term "5 and 6-membered heterocyclyl" is intended to include non-aromatic heterocycles containing one to four heteroatoms selected from nitrogen, oxygen and sulfur. Examples of a 5 or 6-membered heterocyclyl include piperidine, morpholine, thiamorpholine, pyrrolidine, imidazolidine, tetrahydrofuran, piperazine, and the like.

Certain of the above defined terms may occur more than once in the above formula and upon such occurrence each term shall be defined independently of the other; thus for example, $NR^7R^7$ may represent $NH_2$, $NHCH_3$, $N(CH_3)CH_2CH_3$, and the like.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

"Erectile dysfunction" is a disorder involving the failure of a male mammal to achieve erection, ejaculation, or both. Symptoms of erectile dysfunction include an inability to achieve or maintain an erection, ejaculatory failure, premature ejaculation, or inability to achieve an orgasm. An increase in erectile dysfunction is often associated with age and is generally caused by a physical disease or as a side-effect of drug treatment.

By a melanocortin receptor "agonist" is meant an endogenous or drug substance or compound that can interact with a melanocortin receptor and initiate a pharmacological response characteristic of the melanocortin receptor. By a melanocortin receptor "antagonist" is meant a drug or a compound that opposes the melanocortin receptor-associated responses normally induced by another bioactive agent. The "agonistic" properties of the compounds of the present invention were measured in the functional assay described below. The functional assay discriminates a melanocortin receptor agonist from a melanocortin receptor antagonist.

By "binding affinity" is meant the ability of a compound/drug to bind to its biological target, in the the present instance, the ability of a compound of formula I to bind to a melanocortin receptor. Binding affinities for the compounds of the present invention were measured in the binding assay described below and are expressed as $IC_{50}$'s.

"Efficacy" describes the relative intensity with which agonists vary in the response they produce even when they occupy the same number of receptors and with the same affinity. Efficacy is the property that enables drugs to produce responses. Properties of compounds/drugs can be categorized into two groups, those which cause them to associate with the receptors (binding affinity) and those that produce a stimulus (efficacy). The term "efficacy" is used to characterize the level of maximal responses induced by agonists. Not all agonists of a receptor are capable of inducing identical levels of maximal responses. Maximal response depends on the efficiency of receptor coupling, that is, from the cascade of events, which, from the binding of the drug to the receptor, leads to the desired biological effect.

The functional activities expressed as $EC_{50}$'s and the "agonist efficacy" for the compounds of the present invention at a particular concentration were measured in the functional assay described below.

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist as tautomers such as keto-enol tautomers. The individual tautomers as well as mixtures thereof are encompassed with compounds of Formula I.

Compounds of the Formula I may be separated into their individual diastereoisomers by, for example, fractional crystallization from a suitable solvent, for example methanol or ethyl acetate or a mixture thereof, or via chiral chromatography using an optically active stationary phase.

Alternatively, any diastereomer of a compound of the general Formula I or Ia may be obtained by stereospecific synthesis using optically pure starting materials or reagents of known configuration.

Salts

For use in medicine, the salts of the compounds of this invention refer to non-toxic "pharmaceutically acceptable salts." Salts of basic compounds encompassed within the term "pharmaceutically acceptable salts" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calciumn, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobrornine, triethylamine, trimethylarine, tripropylamine, tromethamine, and the like.

It will be understood that, as used herein, references to the compounds of Formula I are meant to also include the pharmaceutically acceptable salts.

Utility

Compounds of formula I are melanocortin receptor agonists and as such are useful in the treatment, control or prevention of diseases, disorders or conditions responsive to the activation of one or more of the melanocortin receptors including, but are not limited to, MC-1, MC-2, MC-3, MC-4, or MC-5. Such diseases, disorders or conditions include, but are not limited to, obesity (by reducing appetite, increasing metabolic rate, reducing fat intake or reducing carbohydrate craving), diabetes mellitus (by enhancing glucose tolerance, decreasing insulin resistance), hypertension, hyperlipidemia, osteoarthritis, cancer, gall bladder disease, sleep apnea, depression, anxiety, compulsion, neuroses, insomnia/sleep disorder, substance abuse, pain, male and female sexual dysfunction (including impotence, loss of libido and erectile dysfunction), fever, inflammation, immunemodulation, rheumatoid arthritis, skin tanning, acne and other skin disorders, neuroprotective and cognitive and memory enhancement including the treatment of Alzheimer's disease. Some compounds encompassed by formula I show highly selective affinity for the melanocortin-4 receptor relative to MC-1R, MC-2R, MC-3R, and MC-5R, which makes them especially useful in the prevention and treatment of obesity, as well as male and/or female sexual dysfunction, including erectile dysfunction.

Administration and Dose Ranges

The term "therapeutically effective amount" is intended to mean that amount of a drug or pharmaceutical agent that will elicit the biological or medical response of a tissue, a system, animal, or human that is being sought by a researcher, veterinarian, medical doctor, or other clinician. The term "prophylactically effective amount" is intended to mean that amount of a pharmaceutical drug that will prevent or reduce the risk of occurrence of the biological or medical event that is sought to be prevented in a tissue, a system, animal, or human that is being sought by a researcher, veterinarian, medical doctor, or other clinician.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. The dosage regimen will also be selected in accordance with the type, species, age, weight, and sex of the subject to be treated. Such dosage may be ascertained readily by a person skilled in the art.

The term "subject" includes mammals, especially humans, who take a melanocortin receptor agonist of the present invention. Administering of the drug to the subject includes both self-administration and administration to the subject by another person.

When treating obesity, in conjunction with diabetes and/or hyperglycemia, or alone, generally satisfactory results are obtained when the compounds of the present invention are administered at a daily dosage of from 0.01 milligram to about 100 milligrams per kilogram of animal body weight, preferably given in a single dose or in divided doses two to six times a day, or in sustained release form. In the case of a 70 kg adult human, the total daily dose will generally be from about 0.7 milligrams to about 3500 milligrams. This dosage regimen may be adjusted to provide the optimal therapeutic response.

When treating diabetes mellitus and/or hyperglycemia, as well as other diseases or disorders for which compounds of formula I are useful, generally satisfactory results are obtained when the compounds of the present invention are administered at a daily dosage of from about 0.001 milligram to about 100 milligram per kilogram of animal body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response.

For the treatment of sexual dysfunction compounds of the present invention are given in a dose range of 0.001 milligram to about 100 milligram per kilogram of body weight, preferably as a single dose orally or as a nasal spray.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to:

(a) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;

(b) insulin or insulin mimetics;

(c) sulfonylureas, such as tolbutamide and glipizide;

(d) α-glucosidase inhibitors (such as acarbose), (e) cholesterol lowering agents such as (i) HMG-CoA reductase inhibitors (Oovastatin, simvastatin, pravastatin, fluvastatin, atorvastatin, and other statins), (ii) sequestrants (cholestyramine, colestipol and a dialkylaminoalkyl derivatives of a cross-linked dextran), (ii) nicotinyl alcohol nicotinic acid or a salt thereof, (iii) proliferator-activater receptor a agonists such as fenofibric acid derivatives (gemfibrozil, clofibrate, fenofibrate and benzafibrate), (iv) inhibitors of cholesterol absorption for example beta-sitosterol and (acyl CoA:cholesterol acyltransferase) inhibitors for example melinamide, (v) probucol, (vi) vitamin E, and (vii) thyromimetics;

(f) PPARδ agonists, such as those disclosed in WO97/28149;

(g) antiobesity compounds, such as fenfluramine, dexfenfluramine, phentermine, sibutramine, orlistat, or $β_3$ adrenergic receptor agonists;

(h) feeding behavior modifying agents, such as neuropeptide Y antagonists (e.g. neuropeptide Y5) such as those disclosed in WO 97/19682, WO 97/20820, WO 97/20821, WO 97/20822 and WO 97/20823;

(i) PPARα agonists such as described in WO 97/36579 by Glaxo;

(j) PPARγ antagonists as described in WO97/10813;

(k) serotonin reuptake inhibitors such as fluoxetine and sertraline;

(l) growth hormone secretagogues such as MK-0677; and (m) agents useful in the treatment of male and/or female sexual dysfunction, such as type V cyclic-GMP-specific phosphodiesterase (PDE-V) inhibitors, such as sildenafil and IC-351, and $α_2$-adrenergic receptor antagonists, such as phentolamine mesylate, and a dopaminergic compound, such as apomorphine.

Pharmaceutical Compositions

Another aspect of the present invention provides pharmaceutical compositions which comprises a compound of Formula I and a pharmaceutically acceptable carrier. The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

PREPARATION OF COMPOUNDS OF THE INVENTION

The compounds of Formula I of the present invention can be prepared according to the procedures of the following Schemes and Examples, using appropriate materials and are further exemplified by the following specific examples. Moreover, by utilizing the procedures described in detail in PCT International Application Publication No. WO 99/64002, published Dec. 16, 1999, which is incorporated by reference herein in its entirety, in conjunction with the disclosure contained herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogencarbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted.

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. CBZ and BOC are commonly used protecting groups in organic synthesis, and their removal conditions are known to those skilled in the art. For example, CBZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of TFA and dimethylsulfide. Removal of BOC protecting groups is carried out with a strong acid, such as trifluoroacetic acid, hydrochloric acid, or hydrogen chloride gas, in a solvent such as methylene chloride, methanol, or ethyl acetate.

Abbreviations Used in the Description of the Preparation of the Compounds of the Present Invention

| | |
|---|---|
| BOC (boc) | t-butyloxycarbonyl |
| BOP | benzotriazol-1-yloxytris(dimethylamino)phosphonium hexafluorophosphate |
| Bu | butyl |
| calc. | calculated |
| CBZ (Cbz) | benzyloxycarbonyl |
| c-hex | cyclohexyl |
| c-pen | cyclopentyl |
| c-pro | cyclopropyl |
| DEAD | diethyl azodicarboxylate |
| DIEA | diisopropylethylamine |
| DMAP | 4-dimethylaminopyridine |
| DMF | N,N-dimethylformamide |
| EDC | 1-(3-dimethylaminopropyl)3-ethylcarbodiimide HCl |
| eq. | equivalent(s) |
| ESI-MS | electron spray ion-mass spectroscopy |
| Et | ethyl |
| EtOAc | ethyl acetate |
| HATU | N-[(diethylamino)-1H-1,2,3-triazolo[4,5-b] pyridin-1-ylmethylene]-N-methylmethanaminium hexafluorophosphate N-oxide |
| HOAt | 1-hydroxy-7-azabenzotriazole |
| HOBt | 1-hydroxybenzotriazole hydrate |
| HPLC | high performance liquid chromatography |
| LDA | lithium diisopropylamide |
| MC-xR | melanocortin receptor (x being a number) |
| Me | methyl |
| MF | molecular formula |
| Ms | methanesulfonyl |
| NMM | N-methylmorpholine |
| Ph | phenyl |
| Phe | phenylalanine |
| Pr | propyl |
| prep. | prepared |
| PyBrop | bromo-tris-pyrrolidino-phosphonium hexafluorophosphate |
| r.t. | room temperature |
| TFA | trifluoroacetic acid |
| THF | tetrahydrofuran |
| TLC | thin-layer chromatography |

Compounds of formula I wherein $R^4$ and $R^5$ are hydrogen may be prepared as shown in Scheme 1 by coupling intermediates of formula 1 with protected amino acids of formula 2 or 3 (PG represents a protecting group such as Boc, CBZ, FMOC, Alloc, etc.) employing standard peptide coupling reaction conditions followed by cleavage of the protecting group PG. The intermediates of formulae 1–3 are synthesized from commercially available materials by methods well-known to one skilled in the art or by methods outlined below. The preparation of intermediates of formula 1 has also been disclosed in WO 00/00000, which is incorporated by reference herein in its entirety. The following section provides illustrative procedures for preparing intermediates of formulae 1–3 useful in the preparation of compounds of the present invention. It is to be appreciated that the choice of reagents, solvents, and reaction conditions, and the like may be varied, and the selection of variables is within the skills of one of ordinary skill in the art.

Scheme 1

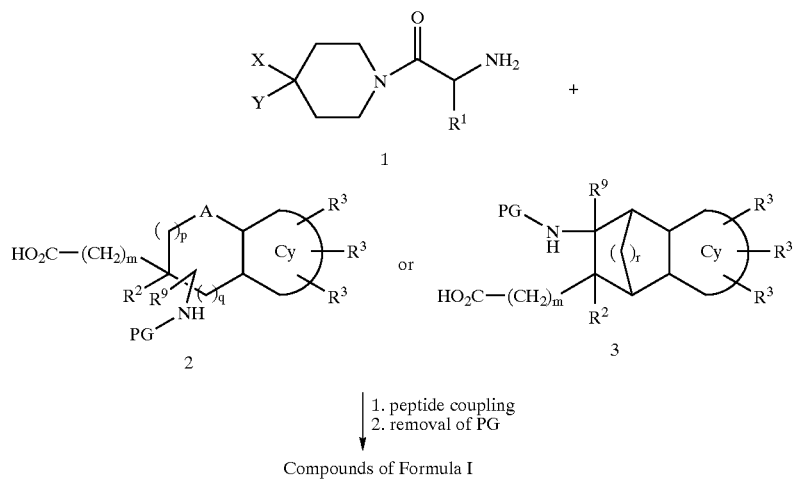

Compounds of Formula I

Compounds of formula I wherein $R^4$ and/or $R^5$ are other than hydrogen can be prepared from a compound of formula I wherein $R^4$ and $R^5$ are hydrogen by reductive amination to introduce an alkyl or substituted alkyl group, or by acylation, sulfonylation, or coupling with protected amino acids. If a protected amino acid is used, deprotection is carried out to liberate the amine functionality.

Preparation of Intermediates

Intermediate 1

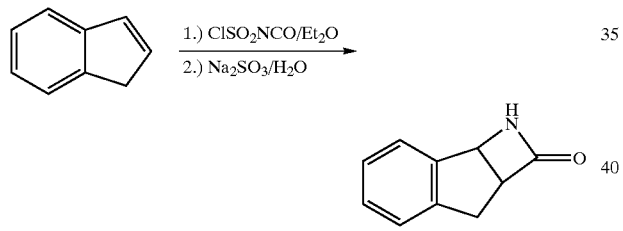

To a solution of indene (4.0 g, 34.4 mmol) in ether (40 ml) was added a solution of chlorosulfonyl isocyanate (3.0 ml, 34.4 mmol) in ether (40 ml). After stirring at 0° C. for 0.5 hour, the reaction mixture was allowed to warm up to room temperature and allowed to stir for another 4 hours. The reaction mixture was poured into 20% aqueous sodium sulfite (80 ml) and stirred vigorously for one hour. After addition of ethyl acetate, the organic layer was separated and the aqueous phase was extracted with ethyl acetate. The combined organic extracts were washed with water and brine, dried over $Na_2SO_4$ and concentrated to give the title compound as a white solid (3.4 g).

ESI-MS: calc. for $C_{10}H_9NO$: 159.1; Found: 160 (M+H), 182 (M+Na).

Intermediate 2

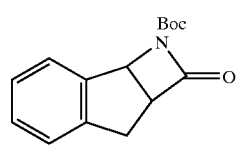

To a solution of Intermediate 1 (3.4 g, 21.4 mmol) in dichloromethane (150 ml) were added triethylamine (8.9 ml, 64.2 mmol), 4-dimethylaminopyridine (0.26 g, 2.14 mmol) and di-tert-butyl dicarbonate (5.1 g, 23.5 mmol) at 0° C. under nitrogen. The reaction mixture was allowed to warm up to room temperature and stirred overnight. The reaction mixture was then concentrated. To the residue was added dichloromethane (80 ml), and the mixture was washed with HCl (0.1N, 30 ml), water, brine, dried over $MgSO_4$, and concentrated to give a brown solid (5.7 g).

ESI-MS: calc. for $C_{15}H_{17}NO_3$: 259; Found: 282 (M+Na).

Intermediate 3

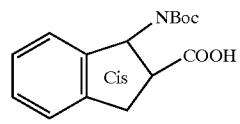

To a solution of Intermediate 2 (0.52 g, 2.0 mmol) in THF (10 ml) was added a solution of lithium hydroxide monohydrate (0.84 g, 20.0 mmol) in water (10 ml). The reaction mixture was stirred at 80° C. overnight. The solvent was removed in vacuo and the aqueous residue was acidified by addition of saturated sodium hydrogen sulfate solution and extracted with ethyl acetate. The combined organic extracts were washed with brine, dried over $MgSO_4$, and concentrated to provide a brown solid (0.38 g).

ESI-MS: calc. for $C_{15}H_{19}NO_4$: 277; Found: 300 (M+Na).

Intermediate 4

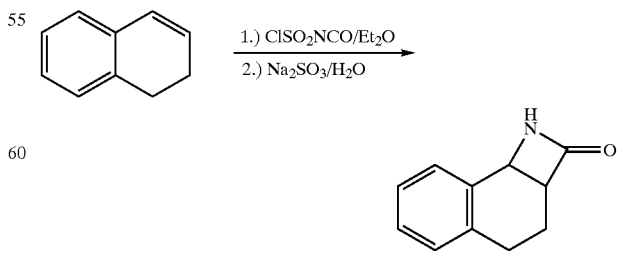

To a solution of 1,2-dihydronaphthalene (4.0 g, 30.7 mmol) in ether (40 ml) was added a solution of chlorosulfonyl isocyanate (2.7 ml, 31.0 mmol) in ether (40 ml). After stirring at 0° C. for 0.5 hour, the reaction mixture was allowed to warm up to room temperature and allowed to stir for another 4 hours. The reaction mixture was poured into 20% aqueous sodium sulfite (80 ml) and stirred vigorously for one hour. After addition of ethyl acetate, the organic layer was separated and the aqueous phase was extracted with ethyl acetate. The combined organic extracts were washed with water and brine, dried over $Na_2SO_4$ and concentrated to give a colorless oil (4.3 g) which was crystallized from a small amount of hexane (3 ml) to give the title compound as a white solid (3.0 g).

ESI-MS: calc. for $C_{11}H_{11}NO$: 173.1; Found: 174 (M+H), 196 (M+Na), 347 (2M+1), 369 (2M+Na).

Intermediate 5

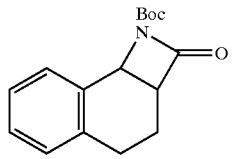

Intermediate 5 was prepared from Intermediate 4 in an analogous manner to the one described for the preparation of Intermediate 2.

ESI-MS: calc. for $C_{16}H_{19}NO_3$: 273.1; Found: 296 (M+Na).

Intermediate 6

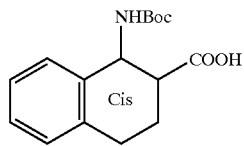

Intermediate 6 was prepared from Intermediate 5 in an analogous manner to the one described for the preparation of Intermediate 3.

ESI-MS: calc. for $C_{16}H_{21}NO_4$: 291.2; Found: 314 (M+Na).

Intermediate 7

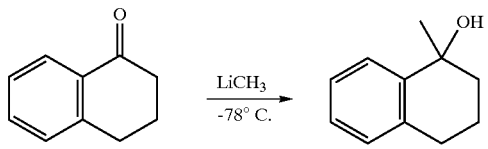

To a solution of tetralone (5.0 g, 34.2 mmol) in THF (75.0 ml) at −78° C. under nitrogen was added methyllithium (45.6 ml, 68.4 mmol). The reaction mixture was stirred at −78° C. for four hours, and warmed up to room temperature and allowed to stir overnight. The reaction mixture was poured onto saturated aqueous ammonium chloride. The organic layer was separated, and the aqueous phase was extracted with ethyl acetate. The combined organic extracts were washed with brine, dried over $MgSO_4$ and evaporated to give a brown solid (5.4 g) which was used without further purification for the preparation of Intermediate 8.

Intermediate 8

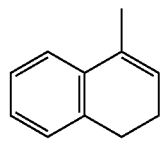

To Intermediate 7 (4.5 g, 27.8 mmol) in toluene (150 ml) was added pyridinium p-toluenesulfonate (0.35 mg, 1.39 mmol). The reaction mixture was refluxed by using a Dean-Stark trap for one hour and concentrated to give a brown oil (4.5 g) which was purified by column chromatography on silica gel (25:1 hexane/ethyl acetate) to give a yellow oil (3.7 g).

Intermediate 9

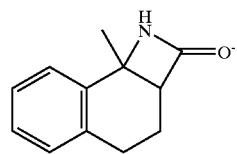

To a solution of intermediate 8 (0.20 g, 1.388 mmol) in ether (5 ml) was added a solution of chlorosulfonyl isocyanate (0.36 ml, 4.16 mmol) in ether (5 ml). After stirring at 0° C. for 24 hours, the reaction mixture was quenched with water. The organic layer was separated and poured into 20% aqueous sodium sulfite (3 ml). The pH was adjusted to 7–8 by addition of 15% aqueous KOH. The resulting mixture was stirred at 0° C. for one hour and then at r.t. for four hours. The organic layer was separated and the aqueous phase was extracted with ether. The combined organic extracts were washed with water and brine, dried over $Na_2SO_4$, and concentrated to give the title compound as a yellow solid (80 mg).

ESI-MS: calc. for $C_{12}H_{13}NO$: 187.1; Found: 188 (M+H), 375 (2M+1), 397 (2M+Na).

Intermediate 10

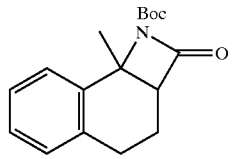

To a solution of Intermediate 9 (180 mg, 0.963 mmol) in THF (10 ml) at 0° C. was added sodium hydride (77 mg, 1.924 mmol, 60% in mineral oil) and di-tert-butyl dicarbonate (314.9 mg, 1.44 mmol) under nitrogen. After stirring 10 min at 0° C., the ice water bath was removed and the reaction mixture was allowed to stir at r.t. for 5 hrs. The reaction mixture was quenched with 0.1 N HCl. The organic layer was separated and extracted with ethyl acetate. The combined organic layers were washed with brine, dried over $MgSO_4$ and concentrated to give the title compound as a yellow oil (400 mg).

ESI-MS: calc. for $C_{17}H_{21}NO_3$: 287; Found: 310 (M+Na).

Intermediate 11

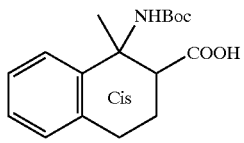

To a solution of Intermediate 10 (0.33 g, 1.15 mmol) in THF (4 ml) was added a solution of sodium hydroxide (0.46 g, 11.5 mmol) in water (4 ml). The reaction mixture was stirred at r.t. overnight. The solvent was removed in vacuo and the aqueous residue was acidified by addition of saturated aqueous sodium hydrogen sulfate and extracted with ethyl acetate. The combined organic extracts were washed with brine, dried over $MgSO_4$, and concentrated to provide a brown solid (0.33 g).

ESI-MS calc. for $C_{17}H_{23}NO_4$: 305; Found: 328 (M+Na).

Intermediate 12

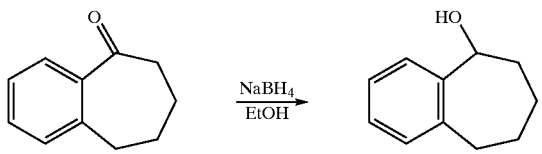

To a solution of 1-benzosuberone (6.0 g, 37.5 mmol) in ethanol (100 ml) was added sodium borohydride (2.1 g, 56.2 mmol), and the reaction mixture was stirred at r.t. under nitrogen overnight. The reaction mixture was concentrated and diluted with ethyl acetate. The organic layer was washed with water and brine, dried over $MgSO_4$ and evaporated to give the title compound as a white solid (6.2 g).

Intermediate 13

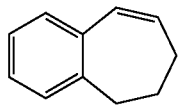

To a solution of Intermediate 12 (6.2 g, 38.2 mmol) in toluene (150 ml) was added p-toluenesulfonic acid monohydrate (145 mg, 0.764 mmol). The reaction mixture was refluxed by using a Dean-stark apparatus for 3 hrs, and solvent was removed to give the title compound as a brown oil (6.0 g).

Intermediate 14

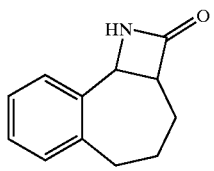

To a solution of Intermediate 13 (0.52 g, 3.57 mmol) in ether (10 ml) was added a solution of chlorosulfonyl isocyanate (0.93 ml, 10.7 mmol) in ether (10 ml). After stirring at 0° C. for 7 days, the reaction mixture was quenched with water. The organic layer was separated and poured into 20% aqueous sodium sulfite (8 ml). The pH was adjusted to 7–8 by addition of 15% aqueous KOH. The resulting mixture was stirred at 0° C. for one hour and then at r.t. for four hours. The organic layer was separated and the aqueous phase was extracted with ether. The combined organic extracts were washed with water and brine, dried over $Na_2SO_4$, and concentrated to give a white solid, which was recrystallized from hexane and ether to give the title compound as a white solid (0.15 g).

ESI-MS: calc. for $C_{12}H_{13}NO$: 187.1; Found: 188 (M+H), 375 (2M+1), 397 (2M+Na).

Intermediate 15

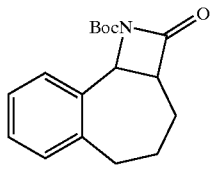

Intermediate 15 was prepared from Intermediate 14 in an analogous manner to the one described for the preparation of Intermediate 2.

ESI-MS: calc. for $C_{17}H_{21}NO_3$: 287; Found: 310 (M+Na).

Intermediate 16

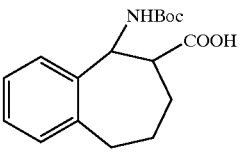

Intermediate 16 was prepared from Intermediate 15 in an analogous manner to the one described for the preparation of Intermediate 3.

ESI-MS: calc. for $C_{17}H_{23}NO_4$: 305.2; Found: 328 (M+Na).

Intermediate 17

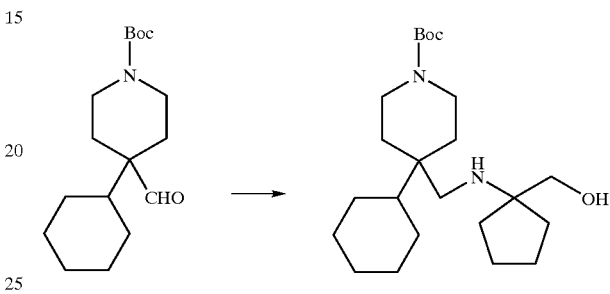

To a solution of 4-cyclohexyl 4-formyl-N-(tertbutyloxycarbonyl)-piperidine (2.56 g, 8.68 mmol) in toluene (100 ml) was added acetic acid (2 ml) and 1-amino-1-cyclopentanemethanol (1.0 g, 8.68 mmol). After refluxing by using a Dean-Stark apparatus for 11 hours, the reaction mixture was concentrated. The residue was dissolved in acetic acid (70 ml) and hydrogenated overnight in the presence of platinum oxide (500 mg) under a balloon atmosphere of hydrogen gas. The catalyst was filtered off and solvent was removed to give a colorless oil, which was dissolved in methanol and made basic by addition of NaOH (5N, 4 ml) and concentrated. The residue was partitioned between water and $CH_2Cl_2$, the two layers separated, and the aqueous layer extracted with $CH_2Cl_2$. The combined organic extracts were washed with brine, dried over $MgSO_4$ and concentrated to give the title compound as a colorless oil (2.1 g).

ESI-MS: calc. for $C_{23}H_{42}N_2O_3$: 394.3; Found: 395 (M+1), 417 (M+Na).

Intermediate 18

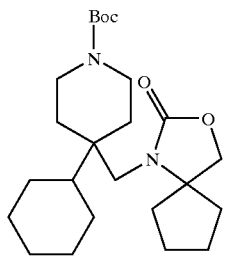

To a solution of Intermediate 17 (2.1 g, 5.33 mmol) in $CH_2Cl_2$ (70 ml) at 0° was added DMAP (0.65 g, 5.33 mmol), DIEA (3.76 ml, 21.3 mmol) followed by slow addition of phosgene (4.1 ml, 8.0 mmol). After stirring the reaction mixture for one hour at 0° C., the ice-water bath was removed and the reaction mixture was continued to stir at r.t. overnight. The mixture was diluted with $CH_2Cl_2$, washed with water and brine, dried over $MgSO_4$ and concentrated to give crude product, which was purified by column chromatography on silica gel (2% $EtOAc/CH_2Cl_2$ to 5% $EtOAc/CH_2Cl_2$) to give the title compound as a white solid (1.2 g).

ESI-MS: calc. for $C_{24}H_{40}N_2O_4$: 420.3; Found: (M+1), (M+Na).

Intermediate 19

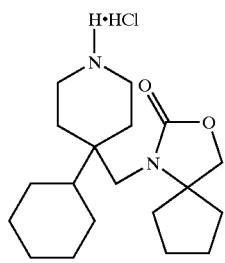

To the Intermediate 18 (1.2 g) was added hydrogen chloride (4.0 M in dioxane). The reaction mixture was stirred at room temperature for 30 minutes and the solvent was removed in vacuo to afford the title compound (1.2 g).
ESI-MS: calc. for $C_{19}H_{32}N_2O_2$: 320.3; Found: 321.1 (M+H).

Intermediate 20

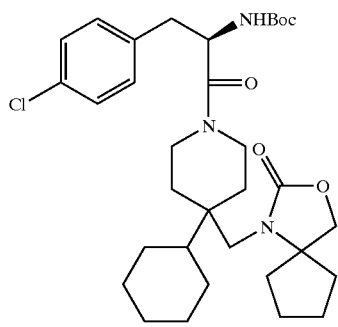

To a solution of Intermediate 19 (1.2 g, 3.37 mmol) in dichloromethane (10 ml) was added 4-methylmorpholine (0.56 ml, 5.055 mmol), HOBt (0.5008 mg, 3.71 mmol), EDC (0.97 g, 5.06 mmol), and Boc-D-4-chlorophenylalanine (1.1 g, 3.71 mmol). The reaction mixture was stirred at room temperature for 18 hrs. Water (3 ml) was added and solvent was removed in vacuo. The aqueous phase was extracted with ethyl acetate. The combined organic extracts were washed with water, dried over $MgSO_4$, and concentrated to provide a white solid (2.2 g), which was purified by column chromatography on silica gel (7:1 $CH_2Cl_2$/EtOAc) to give a white solid (1.45 g).
ESI-MS: calc. for $C_{34}H_{49}ClN_2O_5$: 601; Found: 602 (M+H).

Intermediate 21

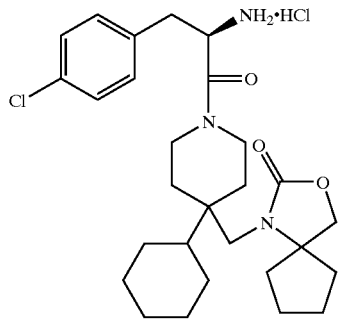

Intermediate 21 was prepared from Intermediate 20 in an analogous manner to the one described for the preparation of Intermediate 19.
ESI-MS calc. for $C_{28}H_{40}ClN_3O_3$: 501; Found: 502 (M+H).

Intermediate 22

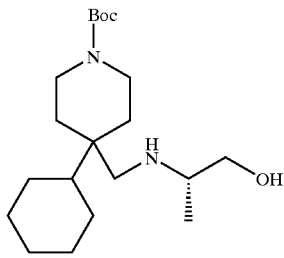

Intermediate 22 was prepared from (S)-(+)-2-amino-1-propanol in an analogous manner to the one described for the preparation of Intermediate 17.
ESI-MS: calc. for $C_{20}H_{38}N_2O_3$: 354; Found: 355 (M+H).

Intermediate 23

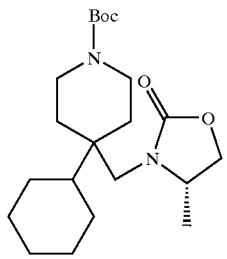

Intermediate 23 was prepared from Intermediate 22 in an analogous manner to the one described for the preparation of Intermediate 18.
ESI-MS: calc. for $C_{21}H_{36}N_2O_4$: 380.3; Found: 381 (M+H).

Intermediate 24

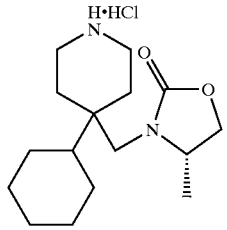

Intermediate 24 was prepared from Intermediate 23 in an analogous manner to the one described for the preparation of Intermediate 19.
ESI-MS: calc. for $C_{16}H_{28}N_2O_2$: 280.3; Found: 281 (M+H).

Intermediate 25

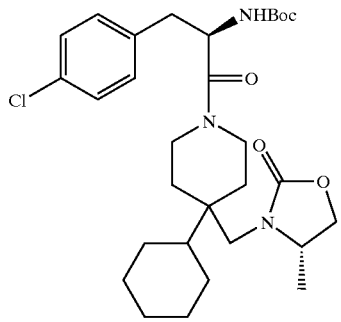

Intermediate 25 was prepared from Intermediate 24 in an analogous manner to the one described for the preparation of Intermediate 20.
ESI-MS: calc. for $C_{30}H_{44}ClN_3O_5$: 561.3; Found: 562 (M+H).

Intermediate 26

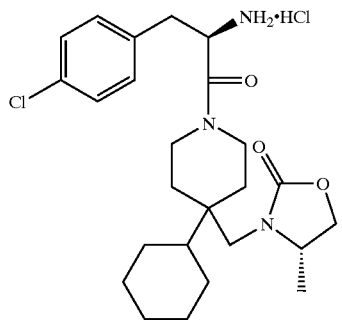

Intermediate 26 was prepared from Intermediate 25 in an analogous manner to the one described for the preparation of Intermediate 19.

ESI-MS: calc. for $C_{25}H_{36}ClN_3O_3$: 461.3; Found: 462 (M+H).

Intermediate 27

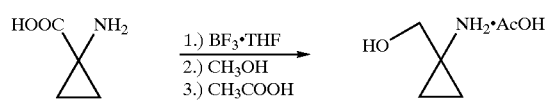

To a suspension of 1-aminocyclopropane-1-carboxylic acid (2.8 g, 27.7 mmol) in THF (20 ml) was added borane-tetrahydrofuran complex (100 ml, 100 mmol) slowly under nitrogen at r.t. The reaction mixture was stirred at 70° C. overnight, then cooled to 0° C. After addition of methanol (12.2 ml, 300 mmol), the mixture was allowed to stir for 30 minutes. Then acetic acid (1.6 ml, 27.7 mmol) was added.

Intermediate 28

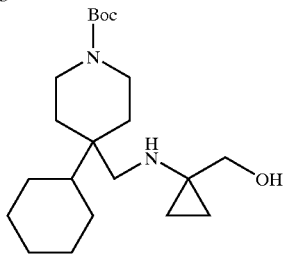

Intermediate 28 was prepared from Intermediate 27 in an analogous manner to the one described for the preparation of Intermediate 17.

ESI-MS: calc. for $C_{21}H_{38}N_2O_3$: 366.3; Found: 367 (M+H).

Intermediate 29

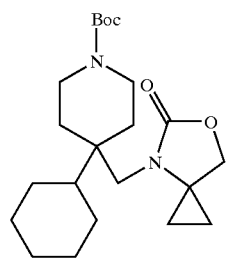

To a solution of Intermediate 28 (0.8 g, 2.18 mmol) in $CH_2Cl_2$ (40 ml) at 0° was added DMAP (0.266 g, 2.18 mmol), DIEA (1.52 ml, 8.74 mmol) and triphosgene (0.648 g, 2.18 mmol). After stirring the reaction mixture for one hour at 0° C., the ice-water bath was removed and the reaction mixture was allowed to stir at r.t. overnight. The mixture was diluted with $CH_2Cl_2$, washed with water and brine, dried over $MgSO_4$ and concentrated to give crude product, which was purified by column chromatography on silica gel (10% $CH_2Cl_2$/EtOAc) to give the title compound as a colorless oil (0.13 g).

ESI-MS: calc. for $C_{22}H_{36}N_2O_4$: 392; Found: 393 (M+1).

Intermediate 30

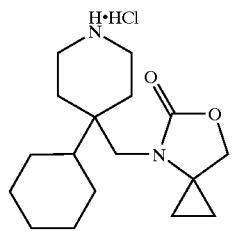

Intermediate 30 was prepared from Intermediate 29 in an analogous manner to the one described for the preparation of Intermediate 19.

ESI-MS: calc. for $C_{17}H_{28}N_2O_2$: 292.2; Found: 293 (M+H).

Intermediate 31

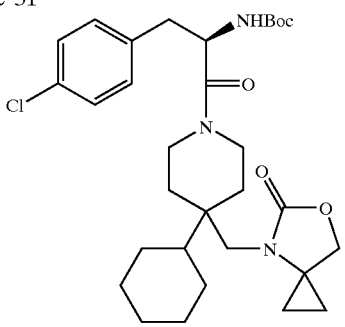

Intermediate 31 was prepared from Intermediate 30 in an analogous manner to the one described for the preparation of Intermediate 20.

ESI-MS: calc. for $C_{31}H_{44}ClN_3O_5$: 573.3; Found: 574 (M+H).

Intermediate 32

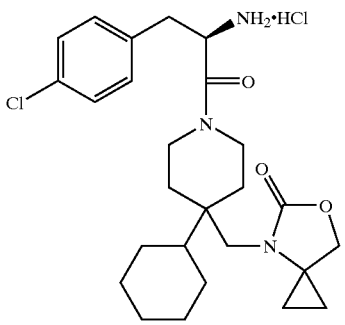

Intermediate 32 was prepared from Intermediate 31 in an analogous manner to the one described for the preparation of Intermediate 19.

ESI-MS: calc. for $C_{26}H_{36}ClN_3O_3$: 473; Found: 474 (M+H).

Intermediate 33

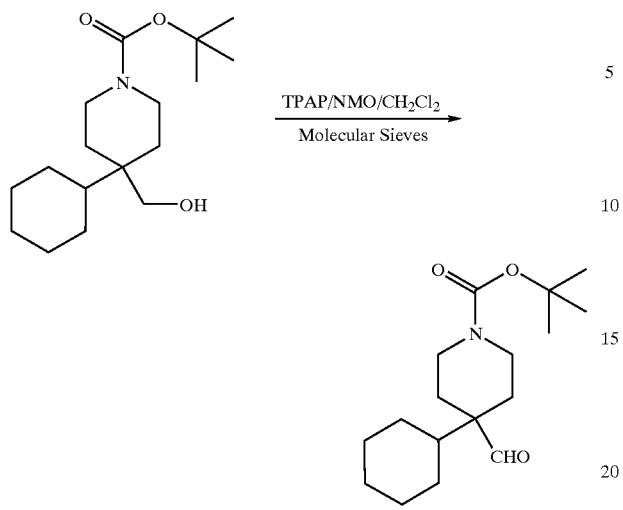

To a solution of the alcohol (9.41 g, 31.6 mmol) in CH$_2$Cl$_2$ (100 ml) at 0° C. containing molecular sieves (2 g) and 4-methylmorpholine N-oxide (4.449 g, 37.98 mmol) was added TPAP (1.12 g, 3.16 mmol). After stirring the reaction mixture at 0° C. for 0.5 h, the reaction mixture was warmed to room temperature and stirred further for 5 hrs. The reaction mixture was concentrated to half the volume, diluted with hexane (250 ml), filtered through a silica gel pad and concentrated to give pure title compound (9.4 g).

Intermediate 34

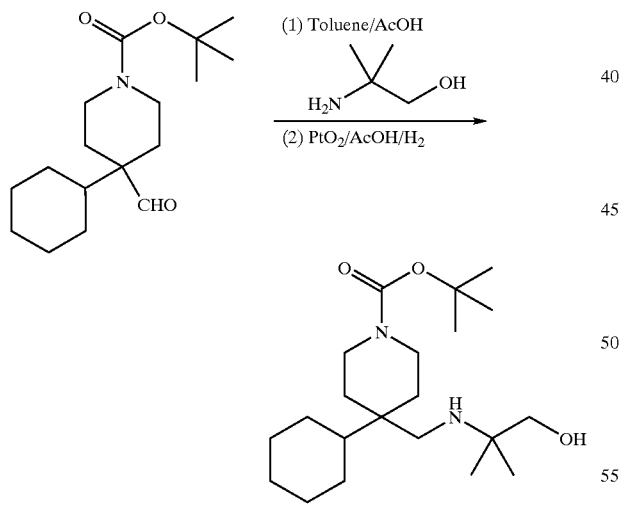

To a solution of the aldehyde (2 g, 6.7 mmol) in toluene (50 ml) was added acetic acid (500 μl). After stirring the reaction mixture at reflux temperature using Dean Stark apparatus for 8 hrs, the mixture was concentrated and dissolved in acetic acid (30 ml). To the mixture was added PtO$_2$ (500 mg) which was stirred under an atmosphere of H$_2$ overnight. The rection mixture was flushed with nitrogen, filtered and concentrated to give the title compound (2 g).

Intermediate 35

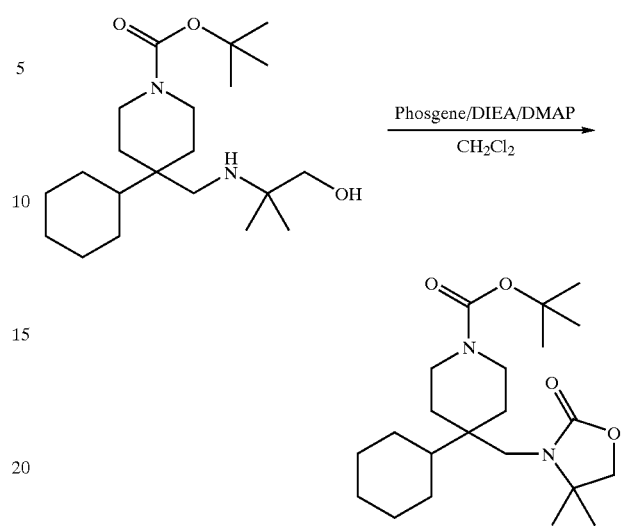

To a solution of the amino alcohol (4.96 g, 13.47 mmol) in CH$_2$Cl$_2$ at 0° C. containing DIEA (6.98 g, 53.9 mmol), DMAP (1.64 g, 13.47 mmol) was added slowly a toluene solution of phosgene (1.93M, 10.47 ml, 20.21 mmol). After stirring the reaction mixture for 1 hr at 0° C., the temperature was raised to room temperature and stirred further for 2 hrs. The reaction mixture was diluted with CH$_2$Cl$_2$, washed with water, brine, dried and concentrated. The residue was purified by column chromatography over silica gel (5% EtOAc/CH$_2$Cl$_2$) to give pure product (3.95 g).

Intermediate 36

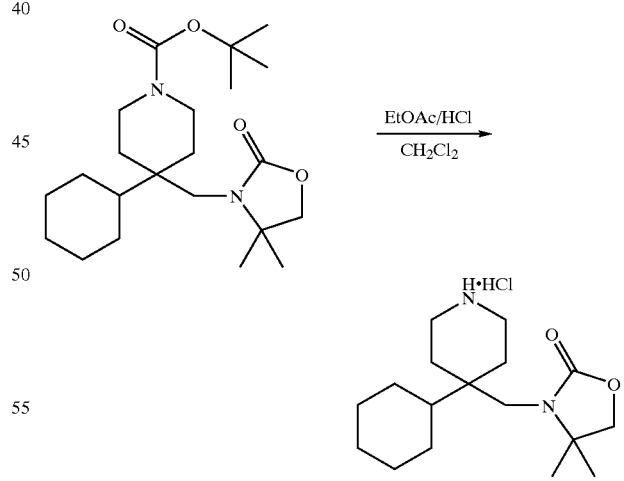

To a solution of Intermediate 35 (3.95 g) in CH$_2$Cl$_2$ was added 5 ml of a saturated HCl solution of EtOAc. After stirring the reaction mixture for 30 minutes at room temperature, the solvent was removed and the residue lyophilized from a benzene/methanol solution to afford the title compound (3.85 g).

Intermediate 37

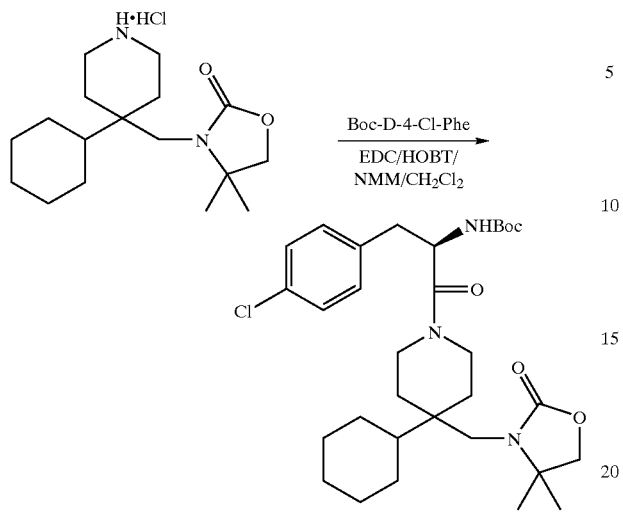

To a solution of Boc-D-4-Cl-Phe (1.6 g, 5.5 mmol) in CH$_2$Cl$_2$ (30 ml) was added EDC (1.84 g, 9.6 mmol), HOBT (1.298 g, 9.6 mmol), NMM (1.67 g, 16.5 mmol) and followed by the oxazolidinone intermediate (1.65 g, 5 mmol). After stirring the reaction mixture overnight at room temperature, the mixture was diluted with CH$_2$Cl$_2$, washed with water, dilute HCl, aqueous NaHCO$_3$ and brine. The organic layer was dried, concentrated and purified by chromatography on silica gel (10% acetone/CH$_2$Cl$_2$) to give 2.55 g of pure product.

ESI-MS: calc. for C$_{31}$H$_{46}$ClN$_3$O$_5$: 575; Found: 576 (M+H).

Intermediate 38

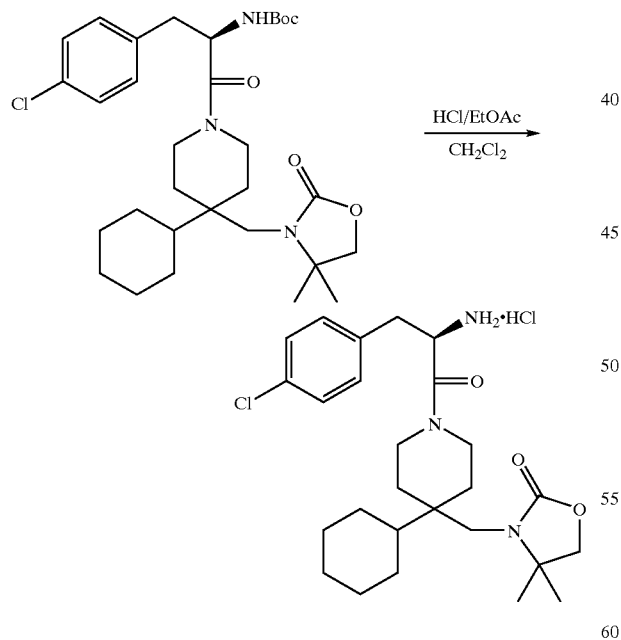

To a solution of Intermediate 37 (2.55 g) in CH$_2$Cl$_2$ (8 ml) was added a saturated HCl solution of EtOAc (8 ml). After stirring the solution for 0.5 hr at 23° C., the mixture was concentrated and lyophilized from benzene/methanol to furnish the desired product (2.4 g).

ESI-MS: calc. for C$_{26}$H$_{38}$ClN$_3$O$_3$: 475; Found: 476 (M+H).

Intermediate 39

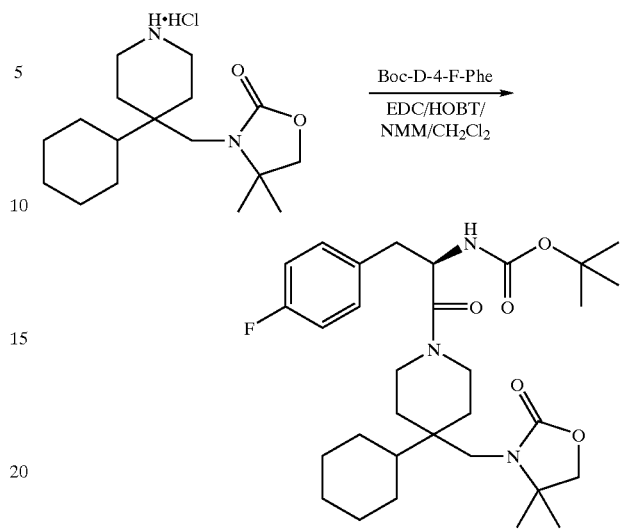

To a solution of Boc-D-4-F-Phe (1.55 g, 5.5 mmol) in CH$_2$Cl$_2$ (30 ml) was added EDC (1.84 g, 9.6 mmol), HOBT (1.29 g, 9.6 mmol), NMM (1.67 g, 16.5 mmol) and the oxazolidinone intermediate (1.65 g, 5 mmol). After stirring the reaction mixture overnight at 23° C., the mixture was diluted with CH$_2$Cl$_2$, washed with water, dilute HCl and aqueous NaHCO$_3$. The organic layer was dried, concentrated and purified by chromatography on silica gel (8% acetone/CH$_2$Cl$_2$) to give pure product (2.34 g).

ESI-MS: calc. for C$_{31}$H$_{46}$FN$_3$O$_5$: 559; Found: 560 (M+H).

Intermediate 40

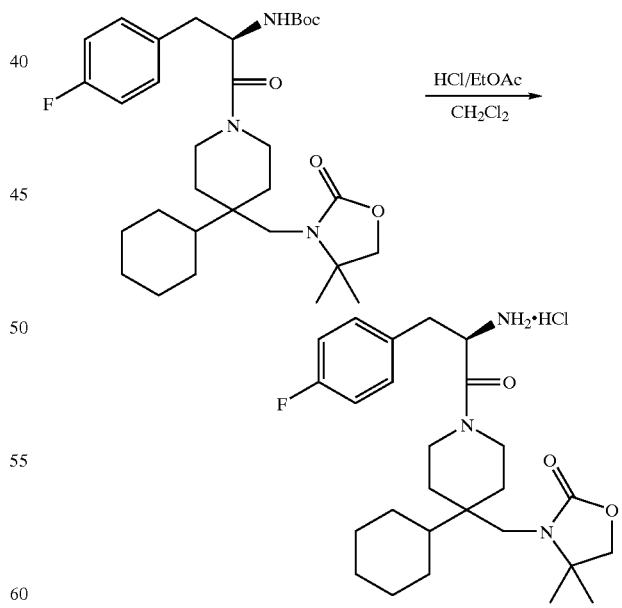

The title compound was prepared in an analogous fashion as Intermediate 38.

The following Examples are provided to illustrate the invention and are not to be construed as limiting the scope of the invention in any manner.

EXAMPLE 1

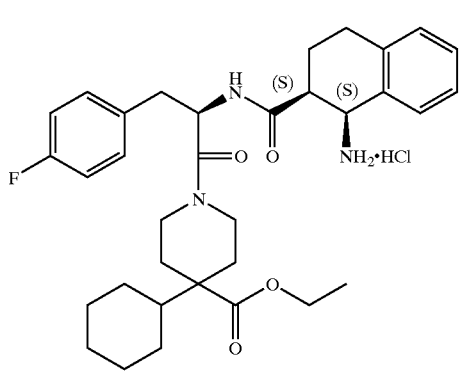

D1

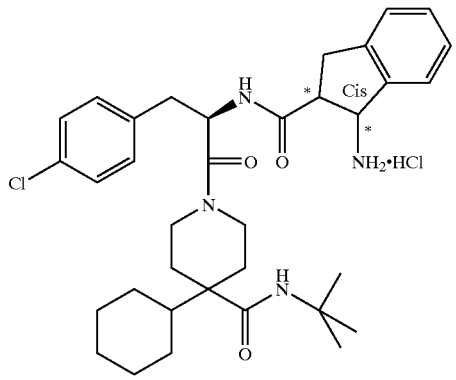

D2

Step A

To a stirred solution of 4-F-D-Phe-4-cyclohexyl-piperidine-4-carboxylic acid ethyl ester HCl salt (187 mg, 0.34 mmol), Intermediate 6 (100 mg, 0.34 mmol), PyBrop (176 mg, 0.38 mmol) and DMAP (25 mg, 0.2 mmol) in dichloromethane (2 mL) was added DIEA (133 mg, 1.0 mmol). The solution was stirred 16 hr, concentrated and chromatographed directly (SiO$_2$,19:1 EtOAc/methanol) to provide 144 mg of the Boc-protected product.

ESI-MS: calc. for $C_{41}H_{57}FN_4O_5$: 704; Found 705 (M+H), 605 (M+H-Boc).

Step B

To a stirred solution of the Boc-protected intermediate from Step A (130 mg, 0.18 mmol) was added HCl-EtOAc (5 mL). The reaction was stirred for 5 minutes at 50° C. and the mixture concentrated. The residue was purified by preparative HPLC (C18 column, 45% to 60% acetonitrile gradient over 10 min. Two product fractions were collected, and the solvent was removed in vacuo to afford 118 mg of the diastereomer D1 as a white solid and 91 mg of the diastereomer D2 as a white solid.

ESI-MS: calc. for D1: $C_{34}H_{44}FN_3O_4$: 577; Found 578 (M+H), 601 (M+Na);

$^1$HNMR (CD$_3$OD; 500 MH): 5.098 (m, 1H); 4.576 (d, J=3 Hz, 1H); 4.513 (d, J=3 Hz, 1H); 0.285 (dt, J=4.4, 13.2 Hz, 1H).

ESI-MS: calc. for D2: $C_{34}H_{44}FN_3O_4$: 577; Found 578 (M+H), 601 (M+Na);

$^1$HNMR (CD$_3$OD; 500 MHz): 5.082 (m, 1H); 4.667 (d, J=3.6 Hz, 1H); 4.633 (d, J=3.4 Hz, 1H); 0.394 (dt, J=4.4, 13.2 Hz, 1H).

EXAMPLE 2

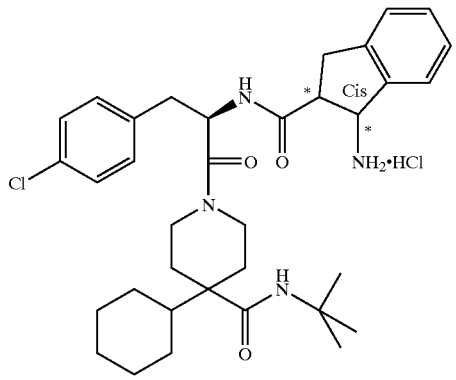

Step A

To a solution of Intermediate 3 (86.5 mg, 0.312 mmol) in dichloromethane (10 ml) were added 4-methylmorpholine (0.047 ml, 0.425 mmol), HOBt (42.2 mg, 0.312 mmol), EDC (81.6 mg, 0.425 mmol), and the t-butyl amide intermediate (159.3 mg, 0.284 mmol). The reaction mixture was stirred at room temperature for 18 hrs. Water (3 ml) was added and solvent was removed in vacuo. The aqueous phase was extracted with ethyl acetate. The combined organic extracts were washed with water and brine, dried over MgSO$_4$ and concentrated to provide a yellow solid (210 mg), which was purified by preparative TLC to give a yellow solid (120 mg).

ESI-MS: calc. for $C_{40}H_{55}ClN4O_5$: 706.4; Found: 707 (M+H).

Step B

To the Boc-protected intermediate from Step A (120 mg) was added 4.0M HCl in dioxane (1 mL). The reaction mixture was stirred at room temperature for 30 minutes and the solvent was removed in vacuo to afford the title compound (120 mg).

ESI-MS: calc. for $C_{35}H_{47}ClN_4O_3$: 606.4; Found: 607.4 (M+H).

EXAMPLES 3–14

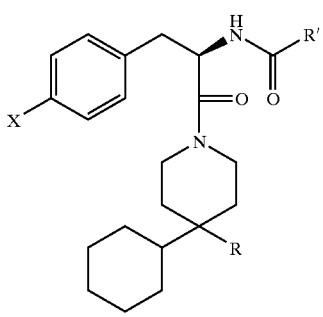

Examples 3–14 were prepared from the appropriate Boc-protected Intermediate and 4-substituted-piperidinyl-phenylalanine intermediate in an analogous two-step sequence described for Examples 1 and 2.

The Boc-protected intermediates with their mass spectral data corresponding to these Examples are listed in the Table below.

| EX. | X | R | R' | Calc. MW | Found ESI-MS |
|---|---|---|---|---|---|
| 3 | F | —CH(—)—COOC₂H₅ | 2-(1-BocHN)indanyl, Cis | C₃₈H₅₀FN₃O₆ 663 | 664 (M + 1) |
| 4 | Cl | —CH(—)—COOC₂H₅ | " | C₃₈H₅₀ClN₃O₆ 679 | 680 (M + 1) |
| 5 | Cl | —CH(—)—COOC₂H₅ | 2-(1-NHBoc)tetrahydronaphthyl, Cis | C₃₉H₅₂ClN₃O₆ 693 | 694 (M + 1) |
| 6 | F | —CH(—)—COOC₂H₅ | " | C₃₉H₅₂FN₃O₆ 677 | 678 (M + 1) |
| 7 | Cl | —CH(—)—CONH—C(CH₃)₃ | " | C₄₁H₅₇ClN₄O₅ 720 | 721 (M + 1) |
| 8 | Cl | spiro-cyclopentyl oxazolidinone-CH₂— | " | C₄₄H₅₉ClN₄O₆ 774 | 775 (M + 1) |
| 9 | Cl | (4S)-methyl oxazolidinone-CH₂— | " | C₄₁H₅₅ClN₄O₆ 734 | 735 (M + 1) |
| 10 | Cl | spiro-cyclopropyl oxazolidinone-CH₂— | " | C₄₂H₅₅ClN₄O₆ 746 | 747 (M + 1) |
| 11 | Cl | 4,4-dimethyl oxazolidinone-CH₂— | 2-(1-NHBoc)benzosuberyl, Cis | C₄₃H₅₉ClN₄O₆ 762 | 763 (M + 1) |
| 12 | Cl | —CH(—)—COOC₂H₅ | " | C₄₀H₅₄ClN₃O₆ 707 | 708 (M + 1) |

-continued

| EX. | X | R | R' | Calc. MW | Found ESI-MS |
|---|---|---|---|---|---|
| 13 | Cl | 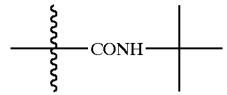—CONH— | " | C$_{42}$H$_{59}$ClN$_4$O$_5$ 734 | 735 (M + 1) |
| 14 | Cl | " | 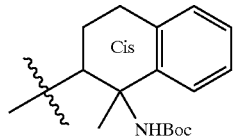 Cis, NHBoc | C$_{42}$H$_{59}$ClN$_4$O$_5$ 734 | 735 (M + 1) |

The final products after cleavage of the Boc-protecting group are listed in the Table below.

| EX. | X | R | R' | Calc. MW | Found ESI-MS |
|---|---|---|---|---|---|
| 3 | F | 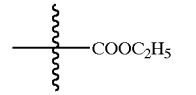—COOC$_2$H$_5$ | 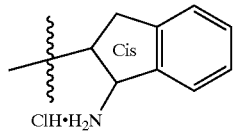 Cis, ClH·H$_2$N | C$_{33}$H$_{42}$FN$_3$O$_4$ 563 | 564 (M + 1) |
| 4 | Cl | 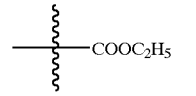—COOC$_2$H$_5$ | " | C$_{33}$H$_{42}$ClN$_3$O$_4$ 579 | 580 (M + 1) |
| 5 | Cl | 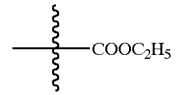—COOC$_2$H$_5$ | 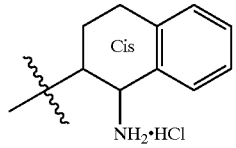 Cis, NH$_2$·HCl | C$_{34}$H$_{44}$ClN$_3$O$_4$ 593 | 594 (M + 1) |
| 6 | F | 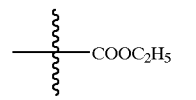—COOC$_2$H$_5$ | " | C$_{34}$H$_{44}$FN$_3$O$_4$ 577 | 578 (M + 1) |
| 7 | Cl | 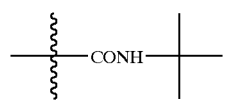—CONH— | " | C$_{36}$H$_{49}$ClN$_4$O$_3$ 620 | 621 (M + 1) |
| 8 | Cl | 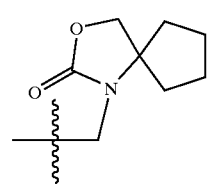 | " | C$_{39}$H$_{51}$ClN$_4$O$_4$ 674 | 675 (M + 1) |
| 9 | Cl | 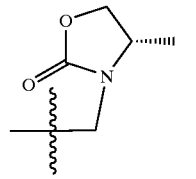 | " | C$_{36}$H$_{47}$ClN$_4$O$_4$ 634 | 635 (M + 1) |

-continued

| EX. | X | R | R' | Calc. MW | Found ESI-MS |
|---|---|---|---|---|---|
| 10 | Cl | (oxazolidinone-spirocyclopropane group) | " | $C_{37}H_{47}ClN_4O_4$ 646 | 647 (M + 1) |
| 11 | Cl | (4,4-dimethyl-oxazolidinone group) | (Cis benzocycloheptane with NH$_2$·HCl) | $C_{38}H_{51}ClN_4O_4$ 662 | 663 (M + 1) |
| 12 | Cl | —COOC$_2$H$_5$ | " | $C_{35}H_{46}ClN_3O_4$ 607 | 608 (M + 1) |
| 13 | Cl | —CONH—C(CH$_3$)$_3$ | " | $C_{37}H_{51}ClN_4O_3$ 634 | 635 (M + 1) |

EXAMPLE 14

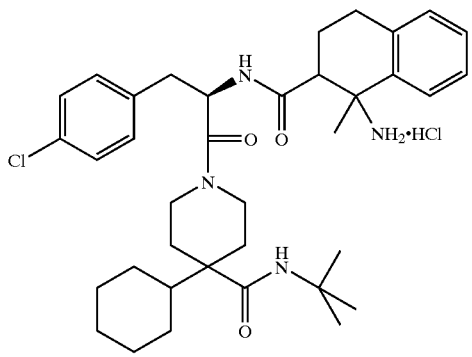

To the Boc-protected intermediate from the Table above (30 mg) was added 4.0M HCl in dioxane (1 mL) at 0° C., and the reaction mixture was stirred at room temperature for 20 minutes and the solvent was removed in vacuo to give a yellow oil, which was purified by preparative HPLC to afford the title compound (4 mg).

ESI-MS: calc. for $C_{37}H_{51}ClN_4O_3$: 634; Found: 635(M+H.

Scheme 2

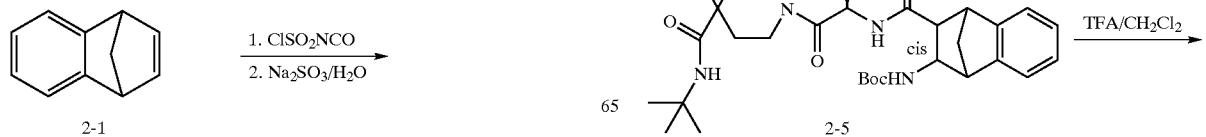

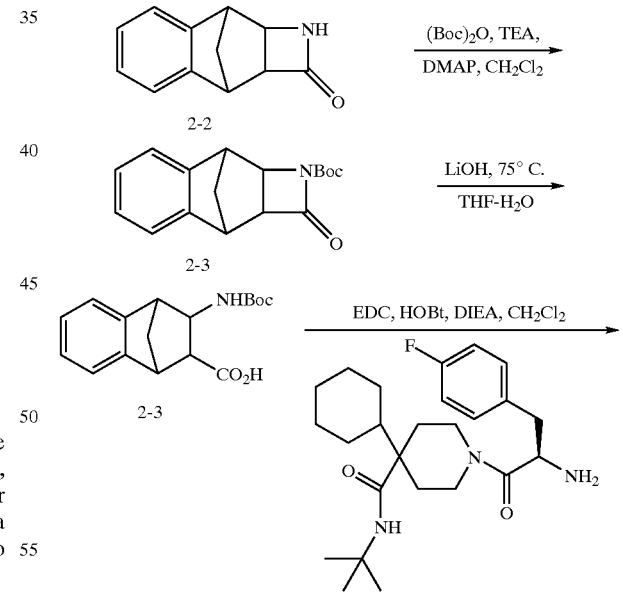

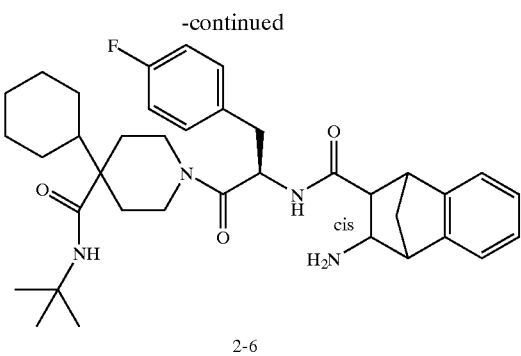

2-6

EXAMPLE 15

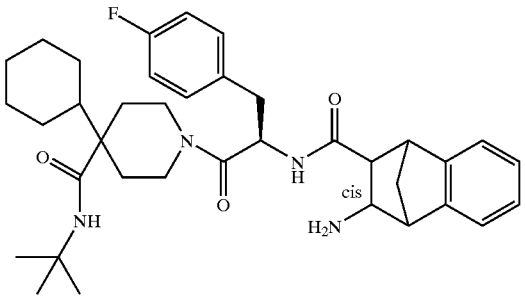

2-6

Step A

A 25-mL, 2-neck round-bottomed flask was purged under nitrogen and charged with 1,4-dihydro-1,4-methanonaphthalene (2-1) (0.8365 g, 5.88 mmol). Chlorosulfonyl isocyanate (1.02 mL, 11.76 mmol) was added dropwise and then stirred at r.t. under $N_2$ for 3 days. The mixture was poured into 60 mL of 20% aq. $Na_2SO_3$ solution and stirred vigorously for 1 h. Ethyl acetate was added, the layers separated and the aqueous layer extracted by ethyl acetate. The combined organic extracts were washed with brine, dried over $Na_2SO_4$, filtered and concentrated to give a red oil. Purification by chromatography on silica gel (9:1 methylene chloride-acetone) gave 2-2 as a white solid (0.452 g).

ESI-MS: Calcd for $C_{12}H_{11}NO$: 185.08; Found: 186 (MW+1).

Step B

To a solution of compound 2-2 (0.449 g, 2.425 mmol) in 12 mL of methylene chloride at 0° C. under nitrogen, TEA (1.01 mL, 7.275 mmol), $(Boc)_2O$ (0.582 g, 2.667 mmol), and DMAP (0.03 g, 0.243 mmol) were added. The reaction mixture was warmed to r.t. and stirred overnight. The reaction mixture was diluted with methylene chloride and washed with 1N HCl and brine, dried over $MgSO_4$, filtered and concentrated. Purification by chromatography on silica gel (30:1 methylene chloride-acetone) gave compound 2-3 as an off-white solid (0.6694 g).

ESI-MS: Calcd. for $C_{17}H_{19}NO_3$: 285.14; Found: 308 ($M^++Na$).

Step C

To a solution of compound 2-3 (0.6658 g, 2.33 mmol) in 50 mL of THF, lithium hydroxide (4.47 g) in 50 mL of $H_2O$ was added. The reaction mixture was refluxed at 75° C. overnight. The reaction mixture was concentrated and $H_2O$ was added and then acidified by adding aqueous $NaHSO_4$ solution until pH=2 was achieved. The solution was extracted with EtOAc and the combined organic extracts were washed with brine, dried over $MgSO_4$, filtered, and concentrated to give compound 24 as an off-white solid (0.6396 g).

ESI-MS: Calcd. for $C_{17}H_{21}NO_4$: 303.15; Found: 304 ($M^++1$).

Step D

Acid 2-4 (0.043 g, 0.143 mmol) was dissolved in 0.65 mL of methylene chloride, and then the 4-F-D-Phe-4-cyclohexyl-piperidine-4-carboxylic acid tert-butyl amide intermediate in Scheme 2 (0.056 g, 0.13 mmol), DIEA (0.09 mL, 0.52 mmol), EDC (0.027 g, 0.143 mmol), and HOBt (0.019 g, 0.143 mmol) were added. The resulting mixture was stirred at r.t. overnight, and then diluted with methylene chloride, and washed with 1N HCl solution, saturated $NaHCO_3$ solution, and brine. The organic layer was dried over $MgSO_4$, filtered, and concentrated. The crude product was purified by column chromatography on silica gel (30:1 to 9:1 methylene chloride-acetone) to give 2-5 as a white foamy solid (0.0643 g).

ESI-MS: Calcd. for $C_{42}H_{57}N_4O_5F$: 716.43; Found: 717 ($M^++1$).

Step E

Compound 2-5 (0.0615 g, 0.086 mmol) was dissolved in 0.21 mL of methylene chloride and 0.21 mL of trifluoroacetic acid. This solution was stirred at r.t. for 30 min, and then coevaporated with toluene (2×5 mL) and diethyl ether (2×5 mL) to give 2-6 as a white foamy solid (0.062 g).

ESI-MS: Calcd. for $C_{37}H_{49}N_4O_3F$: 616.38; Found: 617 ($M^++1$).

EXAMPLES 16–28

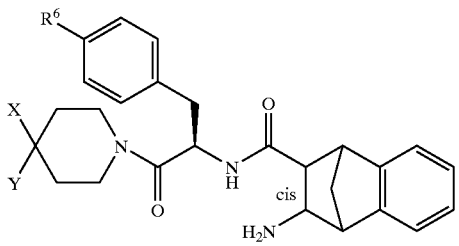

Examples 16–28 were prepared from the Boc-protected amino acid 2-4 and appropriate 4-substituted-piperidinyl-phenylalanine intermediate as depicted in Scheme 2 for Example 15. The Boc-protecting group was cleaved with trifluoroacetic acid in the usual fashion to afford the final product. The Examples are listed in the Table below along with their mass spectral characterization data.

| EX. | Y | X | R⁶ | | Exact Mass | Mass Spec. |
|---|---|---|---|---|---|---|
| 16 | cyclohexyl | —CH(—)C(O)NH-t-Bu | Cl | $d_1 + d_2$ | 632.25 | 633 (M⁺ + 1) |
| 17 | cyclohexyl | —CH(—)C(O)NH-t-Bu | F | $d_1 + d_2$ | 616.38 | 617 (M⁺ + 1) |
| 18 | cyclohexyl | —CH(—)CH₂-N(4,4-dimethyl-oxazolidin-2-one) | F | $d_1 + d_2$ | 644.37 | 645 (M⁺ + 1) |
| 19 | cyclohexyl | —CH(—)CH₂-S-iPr | Cl | $d_1 + d_2$ | 621.32 | 622 (M⁺ + 1) |
| 20 | cyclohexyl | —CH(—)CH₂-S(O)-iPr | Cl | $d_1 + d_2$ | 637.31 | 638 (M⁺ + 1) |
| 21 | cyclohexyl | —CH(—)CH₂-S(O)₂-iPr | Cl | $d_1 + d_2$ | 653.31 | 654 (M⁺ + 1) |
| 22 | phenyl | —CH(—)CH₂-S-iPr | Cl | $d_1 + d_2$ | 615.27 | 616 (M⁺ + 1) |
| 23 | phenyl | —CH(—)CH₂-S(O)-iPr | Cl | $d_1 + d_2$ | 631.26 | 632 (M⁺ + 1) |
| 24 | phenyl | —CH(—)CH₂-S(O)₂-iPr | Cl | $d_1 + d_2$ | 647.26 | 648 (M⁺ + 1) |
| 25 | phenyl | —CH(—)CH₂-S(O)₂-iPr | Cl | $d_1$ | 647.26 | 648 (M⁺ + 1) |

-continued

| EX. | Y | X | R⁶ | | Exact Mass | Mass Spec. |
|---|---|---|---|---|---|---|
| 26 | (isobutyl) | (CH₂-tetrazole) | Cl | $d_1 + d_2$ | 603.31 | 604 (M⁺ + 1) |
| 27 | (isobutyl) | (CH₂-tetrazole) | Cl | $d_1$ | 603.31 | 604 (M⁺ + 1) |
| 28 | (isobutyl) | (CH₂-tetrazole) | Cl | $d_2$ | 603.31 | 604 (M⁺ + 1) |

Biological Assays

A. Binding Assay

The membrane binding assay was used to identify competitive inhibitors of $^{125}$I-NDP-alpha-MSH binding to cloned human MCRs expressed in L- or CHO-cells.

Cell lines expressing melanocortin receptors were grown in T-180 flasks containing selective medium of the composition: 1 L Dulbecco's modified Eagles Medium (DMEM) with 4.5 g L-glucose, 25 mM Hepes, without sodium pyruvate, (Gibco/BRl); 100 ml 10% heat-inactivated fetal bovine serum (Sigma); 10 ml 10,000 unit/ml penicillin & 10,000 ug/ml streptomycin (Gibco/BRl); 10 ml 200 mM L-glutamine (Gibco/BRl); 1 mg/ml Geneticin (G418) (Gibco/BRl). The cells were grown at 37° C. with $CO_2$ and humidity control until the desired cell density and cell number was obtained.

The medium was poured off and 10 mls/monolayer of enzyme-free dissociation media (Specialty Media Inc.) was added. The cells were incubated at 37° C. for 10 minutes or until cells sloughed off when flask was banged against hand.

The cells were harvested into 200 ml centrifuge tubes and spun at 1000 rpm, 4° C., for 10 min. The supernatant was discarded and the cells were resuspended in 5 mls/monolayer membrane preparation buffer having the composition: 10 mM Tris pH 7.2–7.4; 4 ug/ml Leupeptin (Sigma); 10 uM Phosphoramidon (Boehringer Mannheim); 40 ug/ml Bacitracin (Sigma); 5 ug/ml Aprotinin (Sigma); 10 mM Pefabloc (Boehringer Mannheim). The cells were homogenized with motor-driven dounce (Talboy setting 40), using 10 strokes and the homogenate centrifuged at 6,000 rpm, 4° C., for 15 minutes.

The pellets were resuspended in 0.2 mls/monolayer membrane prep buffer and aliquots were placed in tubes (500–1000 ul/tube) and quick frozen in liquid nitrogen and then stored at −80° C.

Test compounds or unlabelled NDP-α-MSH was added to 100 μL of membrane binding buffer to a final concentration of 1 μM. The membrane binding buffer had the composition: 50 mM Tris pH 7.2; 2 mM CaCl2; 1 mM MgCl2; 5 mM KCl; 0.2% BSA; 4 ug/ml Leupeptin (SIGMA); 10 uM Phosphoramidon (Boehringer Mannheim); 40 ug/ml Bacitracin (SIGMA); 5 ug/ml Aprotinin (SIGMA); and 10 mM Pefabloc (Boehringer Mannheim). One hundred μl of membrane binding buffer containing 10–40 ug membrane protein was added, followed by 100 μM 125I-NDP-α-MSH to final concentration of 100 pM. The resulting mixture was vortexed briefly and incubated for 90–120 min at room temp while shaking.

The mixture was filtered with Packard Microplate 196 filter apparatus using Packard Unifilter 96-well GF/C filter with 0.1% polyethyleneimine (Sigma). The filter was washed (5 times with a total of 10 ml per well) with room temperature of filter wash having the composition: 50 mM Tris-HCl pH 7.2 and 20 mM NaCl. The filter was dried, and the bottom sealed and 50 ul of Packard Microscint-20 was added to each well. The top was sealed and the radioactivity quantitated in a Packard Topcount Microplate Scintillation counter.

B. Functional Assay

Functional cell based assays were developed to discriminate melanocortin receptor agonists from antagonists.

Cells (for example, CHO- or L-cells or other eukaryotic cells) expressing a human melanocortin receptor (see e.g. Yang-Y K; Ollmann-M M; Wilson-B D; Dickinson-C; Yamada-T; Barsh-G S; Gantz-I; Mol-Endocrinol. 1997 March; 11(3): 274–80) were dissociated from tissue culture flasks by rinsing with Ca and Mg free phosphate buffered saline (14190-136, Life Technologies, Gaithersburg, Md.) and detached following 5 minutes incubation at 37° C. with enzyme free dissociation buffer (S-014B, Specialty Media, Lavellette, N.J.). Cells were collected by centrifugation and resuspended in Earle's Balanced Salt Solution (14015-069, Life Technologies, Gaithersburg, Md.) with additions of 10 mM HEPES pH 7.5, 5 mM $MgCl_2$, 1 mM glutamine and 1 mg/ml bovine serum albumin. Cells were counted and diluted to 1 to 5×10⁶/ml. The phosphodiesterase inhibitor 3-isobutyl-1-methylxanthine was added to cells to 0.6 mM.

Test compounds were diluted in dimethylsulfoxide (DMSO) ($10^{-5}$ to $10^{-10}$ M) and 0.1 volume of compound solution was added to 0.9 volumes of cell suspension; the final DMSO concentration was 1%. After room temperature incubation for 45 min., cells were lysed by incubation at 100° C. for 5 min. to release accumulated cAMP.

cAMP was measured in an aliquot of the cell lysate with the Amersham (Arlington Heights, Ill.) cAMP detection assay (RPA556). The amount of cAMP production which resulted from an unknown compound was compared to that amount of cAMP produced in response to alpha-MSH which was defined as a 100% agonist. The $EC_{50}$ is defined as the compound concentration which results in half maximal stimulation, when compared to its own maximal level of stimulation.

Antagonist Assay

Antagonist activity was defined as the ability of a compound to block cAMP production in response to alpha-MSH. Solution of test compounds and suspension of receptor containing cells were prepared and mixed as described above; the mixture was incubated for 15 min., and an $EC_{50}$ dose (approximately 10 nM alpha-MSH) was added to the cells. The assay was terminated at 45 min. and cAMP quantitated as above. Percent inhibition was determined by comparing the amount of cAMP produced in the presence to that produced in the absence of test compound.

C. In vivo Food Intake Models

1) Overnight Food Intake

Sprague Dawley rats are injected intracerebroventricularly with a test compound in 400 nL of 50% propylene glycol/artificial cerebrospinal fluid one hour prior to onset of dark cycle (12 hours). Food intake is determined using a computerized system in which each rat's food is placed on a computer monitored balance. Cumulative food intake for 16 hours post compound administration is measured.

2) Food Intake in Diet Induced Obese Mice

Male C57/B16J mice maintained on a high fat diet (60% fat calories) for 6.5 months from 4 weeks of age are are dosed intraperitoneally with test compound. Food intake and body weight are measured over an eight day period. Biochemical parameters relating to obesity, including leptin, insulin, triglyceride, free fatty acid, cholesterol and serum glucose levels are determined.

D. Rat Ex Copula Assay

Sexually mature male Caesarian Derived Sprague Dawley (CD) rats (over 60 days old) are used with the suspensory ligament surgically removed to prevent retraction of the penis back into the penile sheath during the ex copula evaluations. Animals receive food and water ad lib and are kept on a normal light/dark cycle. Studies are conducted during the light cycle.

1) Conditioning to Supine Restraint for Ex Copula Reflex Tests

This conditioning takes ~4 days. Day 1, the animals are placed in a darkened restrainer and left for 15–30 minutes. Day 2, the animals are restrained in a supine position in the restrainer for 15–30 minutes. Day 3, the animals are restrained in the supine position with the penile sheath retracted for 15–30 minutes. Day 4, the animals are restrained in the supine position with the penile sheath retracted until penile responses are observed. Some animals require additional days of conditioning before they are completely acclimated to the procedures; non-responders are removed from further evaluation. After any handling or evaluation animals are given a treat to ensure positive reinforcement.

2) Ex Copula Reflex Tests

Rats are gently restrained in a supine position with their anterior torso placed inside a cylinder of adequate size to allow for normal head and paw grooming. For a 400–500 gram rat, the diameter of the cylinder is approximately 8 cm. The lower torso and hind limbs are restrained with a non-adhesive material (vetrap). An additional piece of vetrap with a hole in it, through which the glans penis will be passed, is fastened over the animal to maintain the preputial sheath in a retracted position. Penile responses will be observed, typically termed ex copula genital reflex tests. Typically, a series of penile erections will occur spontaneously within a few minutes after sheath retraction. The types of normal reflexogenic erectile responses include elongation, engorgement, cup and flip. An elongation is classified as an extension of the penile body. Engorgement is a dilation of the glans penis. A cup is defined as an intense erection where the distal margin of the glans penis momentarily flares open to form a cup. A flip is a dorsiflexion of the penile body.

Baseline and or vehicle evaluations are conducted to determine how and if an animal will respond. Some animals have a long duration until the first response while others are non-responders altogether. During this baseline evaluation latency to first response, number and type of responses are recorded. The testing time frame is 15 minutes after the first response.

After a minimum of 1 day between evaluations, these same animals are administered the test compound at 20 mg/kg and evaluated for penile reflexes. All evaluations are videotaped and scored later. Data are collected and analyzed using paired 2 tailed t-tests to compared baseline and/or vehicle evaluations to drug treated evaluations for individual animals. Groups of a minimum of 4 animals are utilized to reduce variability.

Positive reference controls are included in each study to assure the validity of the study. Animals can be dosed by a number of routes of administration depending on the nature of the study to be performed. The routes of administration includes intravenous (IV), intraperitoneal (IP), subcutaneous (SC) and intracerebral ventricular (ICV).

E. Models of Female Sexual Dysfunction

Rodent assays relevant to female sexual receptivity include the behavioral model of lordosis and direct observations of copulatory activity. There is also a urethrogenital reflex model in anesthetized spinally transected rats for measuring orgasm in both male and female rats. These and other established animal models of female sexual dysfunction are described in McKenna K E et al, *A Model For The Study of Sexual Function In Anesthetized Male And Female Rats,* Am. J. Physiol. (Regulatory Integrative Comp. Physiol 30): R1276–R1285, 1991; McKenna K E et al, *Modulation By Peripheral Serotonin of The Threshold For Sexual Reflexes In Female Rats,* Pharm. Bioch. Behav., 40:151–156, 1991; and Takahashi L K et al, *Dual Estradiol Action In The Diencephalon And The Regulation Of Sociosexual Behavior In Female Golden Hamsters,* Brain Res., 359:194–207, 1985.

Representative compounds of the present invention were tested and found to bind to the melanocortin-4 receptor. These compounds were generally found to have $IC_{50}$ values less than 2 µM. Representative compounds of the present invention were also tested in the functional assay and found generally to activate the melanocortin-4 receptor with $EC_{50}$ values less than 1 µM.

EXAMPLES OF A PHARMACEUTICAL COMPOSITION

As a specific embodiment of an oral composition of a composition of the present invention, 5 mg of Example 2 is formulated with sufficient finely divided lactose to provide a total amount of 580 to 590 mg to fill a size O hard gelatin capsule.

As another specific embodiment of an oral composition of a compound of the present invention, 2.5 mg of Example 2 is formulated with sufficient finely divided lactose to provide a total amount of 580 to 590 mg to fill a size O hard gelatin capsule.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of structural formula I:

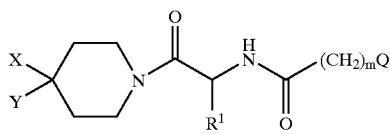

(I)

wherein

Q is

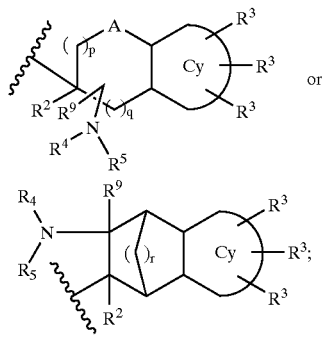

Cy is selected from the group consisting of
aryl,
5- or 6-membered heteroaryl,
5- or 6-membered heterocyclyl, and
5- to 7-membered carbocyclyl;
wherein Cy is substituted with one to three groups independently selected from $R^3$;
A is O, $S(O)_m$, $NR^7$, or $CH_2$;
m is 0, 1, or 2;
n is 0, 1, 2, or 3;
p is 0, 1 or 2;
q is 0, 1 or 2;
r is 1, 2, or 3;
$R^1$ is selected from the group consisting of
hydrogen,
$C_{1-8}$ alkyl,
$(CHR^7)_n$—$C_{3-7}$ cycloalkyl,
$(CHR^7)_n$aryl, and
$(CHR^7)_n$heteroaryl;
in which aryl and heteroaryl are unsubstituted or substituted with one to three groups independently selected from $R^6$; and alkyl and cycloalkyl are unsubstituted or substituted with one to three groups independently selected from $R^6$ and oxo;
$R^2$ is selected from the group consisting of
hydrogen,
$C_{1-8}$ alkyl,
$(CH_2)_nC_{3-7}$ cycloalkyl, and
$(CH_2)_n$-aryl;
each $R^3$ is independently selected from
hydrogen,
$C_{1-8}$ alkyl,
$(CH_2)_n$-aryl,
$(CH_2)_nC_{3-7}$ cycloalkyl,
$(CH_2)_n$-heteroaryl,
halo,
$OR^7$,
$NHSO_2R^7$,
$N(R^7)_2$,
$C\equiv N$,
$CO_2R^7$,
$C(R^7)(R^7)N(R^7)_2$,
$NO_2$,
$SO_2N(R^7)_2$,
$S(O)_mR^7$,
$CF_3$, and
$OCF_3$;
$R^4$ and $R^5$ are each independently selected from the group consisting of
hydrogen,
$C_{1-10}$ alkyl, and
$C_{3-8}$ cycloalkyl;
or $R^4$ and $R^5$ together with the nitrogen to which they are attached form a 5- to 8-membered ring optionally containing an additional heteroatom selected from O, S, and $NR^7$;
wherein alkyl and cycloalkyl are unsubstituted or substituted with one to three groups independently selected from $R^6$ and oxo;
$R^6$ is selected from the group consisting of
$C_{1-8}$ alkyl,
$(CH_2)_n$-aryl,
$(CH_2)_nC_{3-7}$ cycloalkyl,
$(CH_2)_n$-heteroaryl,
halo,
$OR^7$,
$NHSO_2R^7$,
$N(R^7)_2$,
$C\equiv N$,
$CO_2R^7$,
$C(R^7)(R^7)N(R^7)_2$,
$NO_2$,
$SO_2N(R^7)_2$,
$S(O)_mR^7$,
$CF_3$, and
$OCF_3$;
each $R^7$ is independently selected from the group consisting of
hydrogen,
$C_{1-8}$ alkyl,
$(CH_2)_n$-aryl, and
$(CH_2)_nC_{3-7}$ cycloalkyl;
each $R^8$ is independently selected from the group consisting of
hydrogen,
$C_{1-8}$ alkyl,
$(CH_2)_n$-aryl,
$(CH_2)_n$-heteroaryl, and
$(CH_2)_nC_{3-7}$ cycloalkyl;

wherein aryl and heteroaryl are unsubstituted or substituted with one to three groups independently selected from $R^6$; and alkyl, cycloalkyl, and $(CH_2)_n$ are unsubstituted or substituted with one to three groups independently selected from $R^6$ and oxo; or two $R^8$ groups together with the atoms to which they are attached form a 5- to 8-membered mono- or bi-cyclic ring system optionally containing an additional heteroatom selected from O, S, and $NR^7$;

$R^9$ is hydrogen or $C_{1-4}$ alkyl;

X is selected from the group consisting of
$C_{1-8}$ alkyl,
$(CH_2)_nC_{3-8}$ cycloalkyl,
$(CH_2)_n$aryl,
$(CH_2)_n$heteroaryl,
$(CH_2)_n$heterocyclyl,
$(CH_2)_nC\equiv N$,
$(CH_2)_nCON(R^8R^8)$,
$(CH_2)_nCO_2R^8$,
$(CH_2)_nCOR^8$
$(CH_2)_nNR^8C(O)R^8$,
$(CH_2)_nNR^8CO_2R^8$,
$(CH_2)_nNR^8C(O)N(R^8)_2$,
$(CH_2)_nNR^8SO_2R^8$,
$(CH_2)_nS(O)_mR^8$,
$(CH_2)_nSO_2N(R^8)(R^8)$,
$(CH_2)_nOR^8$,
$(CH_2)_nOC(O)R^8$,
$(CH_2)_nOC(O)OR^8$,
$(CH_2)_nOC(O)N(R^8)_2$,
$(CH_2)_nN(R^8)(R^8)$, and
$(CH_2)_nNR^8SO_2N(R^8)(R^8)$;
   wherein aryl and heteroaryl are unsubstituted or substituted with one to three groups selected from $R^6$, and alkyl, $(CH_2)_n$, cycloalkyl, and heterocyclyl are unsubstituted or substituted with one to four groups independently selected from $R^6$ and oxo;

Y is selected from the group consisting of
hydrogen,
$C_{1-8}$ alkyl,
$(CH_2)_nC_{3-8}$ cycloalkyl,
$(CH_2)_n$aryl,
$(CH_2)_n$heterocyclyl, and
$(CH_2)_n$heteroaryl;
   wherein aryl and heteroaryl are unsubstituted or substituted with one to three groups selected from $R^6$; and alkyl, $(CH_2)_n$, cycloalkyl, and heterocyclyl are optionally substituted with one to three groups selected from $R^6$ and oxo;

or a pharmaceutically acceptable salt thereof.

2. The compound of claim 1 wherein Cy is selected from the group consisting of benzene, pyridine, pyrazine, piperidine, and cyclohexane.

3. The compound of claim 2 wherein Cy is benzene or cyclohexane.

4. The compound of claim 1 wherein $R^1$ is $CH(R^7)$-aryl or $CH(R^7)$-heteroaryl wherein aryl and heteroaryl are optionally substituted with one or two $R^6$ groups.

5. The compound of claim 4 wherein $R^1$ is benzyl optionally substituted with one or two groups selected from halogen, $C_{1-4}$ alkyl, $C_{1-4}$ alkoxy, $CF_3$, and $OCF_3$.

6. The compound of claim 5 wherein $R^1$ is 4-chlorobenzyl, 4-fluorobenzyl, or 4-methoxybenzyl.

7. The compound of claim 1 wherein $R^2$ is H or $CH_3$.

8. The compound of claim 1 wherein X is $(CH_2)_n$-aryl, $(CH_2)_n$-heteroaryl, $(CH_2)_n$-heterocyclyl, $(CH_2)_nC(O)N$ $(R^8)$, $(CH_2)_nCO_2R^8$, $(CH_2)_nOR^8$, $(CH_2)_nNR^8C(O)R^8$, or $(CH_2)_nNR^8SO_2R^8$, wherein aryl and heteroaryl are optionally substituted with one to three groups selected from $R^6$; heterocyclyl is optionally substituted with one to three groups selected from $R^6$ and oxo; and the $(CH_2)_n$ group is optionally substituted with one to three groups selected from $R^7$, halo, $S(O)_mR^7$, $N(R^7)_2$, and $OR^7$.

9. The compound of claim 8 wherein X is $CH_2$-heteroaryl, $CH_2$-heterocyclyl, $NHC(O)R^8$, $CO_2R^8$, or $C(O)N(R^8)(R^8)$, wherein heteroaryl is optionally substituted with one to three groups selected from $R^6$; heterocyclyl is optionally substituted with one to three groups selected from $R^6$ and oxo; and wherein $R^8$ is each independently selected from H and $C_{1-6}$ alkyl optionally substituted with $OR^7$, $SR^7$, or $N(R^7)_2$, or 2 $R^7$ groups together with the nitrogen to which they are attached form a 5- or 6-membered ring optionally having an additional heteroatom selected from O, S and $NR^7$.

10. The compound of claim 9 wherein heteroaryl is selected from the group consisting of pyridyl, pyrazinyl, pyrimidinyl, triazolyl, tetrazolyl, thiadiazolyl, oxadiazolyl, pyrazolyl, and imidazolyl.

11. The compound of claim 1 wherein Y is $C_{1-8}$ alkyl, $(CH_2)_nC_{5-7}$ cycloalkyl, $(CH_2)_n$-aryl, $(CH_2)_n$-heterocyclyl or $(CH_2)_n$-heteroaryl, wherein aryl and heteroaryl are optionally substituted with one to three groups selected from $R^6$; and $(CH_2)_n$, alkyl, cycloalkyl, and heterocyclyl are optionally substituted with one to three groups selected from $R^6$ and oxo.

12. The compound of claim 11 wherein Y is cyclohexyl, cycloheptyl, cyclopentyl, phenyl, or $C_{1-6}$ alkyl, unsubstituted or substituted with one to three groups selected from $R^6$ and oxo.

13. The compound of claim 12 wherein Y is cyclohexyl or $C_{1-6}$ alkyl, wherein the cyclohexyl and alkyl groups are unsubstituted or substituted with one to three groups selected from $R^6$ and oxo.

14. The compound of claim 1 of formula Ia:

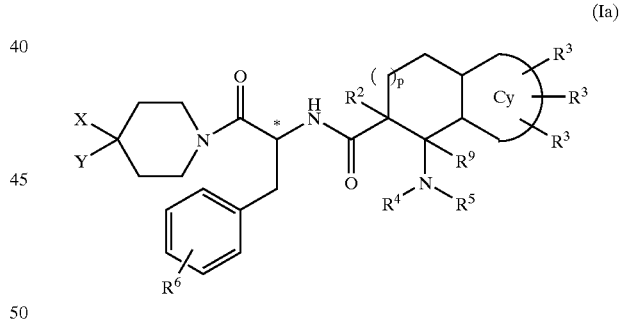

(Ia)

wherein
Cy is phenyl or cyclohexyl,
   wherein Cy is substituted with one to three groups independently selected from $R^3$;
n is 1 or 2;
p is 0, 1, or 2;
$R^2$ is selected from the group consisting of
   hydrogen,
   $C_{1-6}$ alkyl, and
   $C_{5-6}$ cycloalkyl;
each $R^3$ is independently selected from
   hydrogen,
   $C_{1-8}$ alkyl,
   $(CH_2)_n$-aryl,
   $(CH_2)_nC_{3-7}$ cycloalkyl,
   $(CH_2)_n$-heteroaryl, halo,
OR$^7$,
NHSO$_2$R$^7$,
N(R$^7$)$_2$,
N≡N
CO$_2$R$^7$,
C(R$^7$)(R$^7$)N(R$^7$)$_2$,
NO$_2$,
SO$_2$N(R$^7$)$_2$,
S(O)$_m$R$^7$,
CF$_3$, and
OCF$_3$;
R$^4$ and R$^5$ are each independently selected from the group consisting of
hydrogen,
C$_{1-6}$ alkyl, and
C$_{5-6}$ cycloalkyl;
or R$^4$ and R$^5$ together with the nitrogen to which they are attached form a 5- to 8-membered ring optionally containing an additional heteroatom selected from O, S, and NR$^7$;
wherein alkyl and cycloalkyl are unsubstituted or substituted with one to three groups independently selected from R$^6$ and oxo;
R$^6$ is selected from the group consisting of
C$_{1-8}$ alkyl,
(CH$_2$)$_n$-aryl,
(CH$_2$)$_n$C$_{3-7}$cycloalkyl,
(CH$_2$)$_n$-heteroaryl,
halo,
OR$^7$,
NHSO$_2$R$^7$,
N(R$^7$)$_2$,
C≡N,
CO$_2$R$^7$,
C(R$^7$)(R$^7$)N(R$^7$)$_2$,
NO$_2$,
SO$_2$N(R$^7$)$_2$,
S(O)$_m$R$^7$,
CF$_3$, and
OCF$_3$;
each R$^7$ is independently selected from the group consisting of
hydrogen,
C$_{1-8}$ alkyl, and
C$_{3-6}$ cycloalkyl;
each R$^8$ is independently selected from the group consisting of
hydrogen,
C$_{1-5}$ alkyl,
aryl,
heteroaryl, and
C$_{5-6}$ cycloalkyl;
wherein aryl and heteroaryl are unsubstituted or substituted with one to three groups independently selected from R$^6$; and alkyl and cycloalkyl are unsubstituted or substituted with one to three groups independently selected from R$^6$ and oxo; or two R$^8$ groups together with the atoms to which they are attached form a 5- to 8-membered mono- or bi-cyclic ring optionally containing an additional heteroatom selected from O, S, and NR$^7$;
R$^9$ is hydrogen or C$_{1-4}$ alkyl;
X is selected from the group consisting of
C$_{1-8}$ alkyl,
(CH$_2$)$_n$C$_{3-8}$cycloalkyl,
(CH$_2$)$_n$aryl,
(CH$_2$)$_n$heteroaryl,
(CH$_2$)$_n$heterocyclyl,
(CH$_2$)$_n$C≡N,
(CH$_2$)$_n$CON(R$^8$R$^8$),
(CH$_2$)$_n$CO$_2$R$^8$,
(CH$_2$)$_n$COR$^8$,
(CH$_2$)$_n$NR$^8$C(O)R$^8$,
(CH$_2$)$_n$NR$^8$CO$_2$R$^8$,
(CH$_2$)$_n$NR$^8$C(O)N(R$^8$)$_2$,
(CH$_2$)$_n$NR$^8$SO$_2$R$^8$,
(CH$_2$)$_n$S(O)mR$^8$,
(CH$_2$)$_n$SO$_2$N(R$^8$)(R$^8$),
(CH$_2$)$_n$OR$^8$,
(CH$_2$)$_n$OC(O)R$^8$,
(CH$_2$)$_n$OC(O)OR$^8$,
(CH$_2$)$_n$OC(O)N(R$^8$)$_2$,
(CH$_2$)$_n$N(R$^8$)(R$^8$), and
(CH$_2$)$_n$NR$^8$SO$_2$N(R$^8$)(R$^8$);
wherein aryl and heteroaryl are unsubstituted or substituted with one to three groups selected from R$^6$, and alkyl, (CH$_2$)$_n$, cycloalkyl, and heterocyclyl are unsubstituted or substituted with one to four groups independently selected from R$^6$ and oxo;
Y is selected from the group consisting of
hydrogen,
C$_{1-8}$ alkyl,
(CH$_2$)$_n$C$_{3-6}$ cycloalkyl,
(CH$_2$)$_n$aryl, and
(CH$_2$)$_n$heteroaryl;
wherein aryl and heteroaryl are unsubstituted or substituted with one to three groups selected from R$^6$; and alkyl, (CH$_2$)$_n$, and cycloalkyl are unsubstituted or substituted with one to three groups selected from R$^6$ and oxo;
or a pharmaceutically acceptable salt thereof.

15. The compound of claim 14 wherein the carbon atom marked with * has the R configuration.

16. The compound of claim 14 wherein X is selected from the group consisting of:

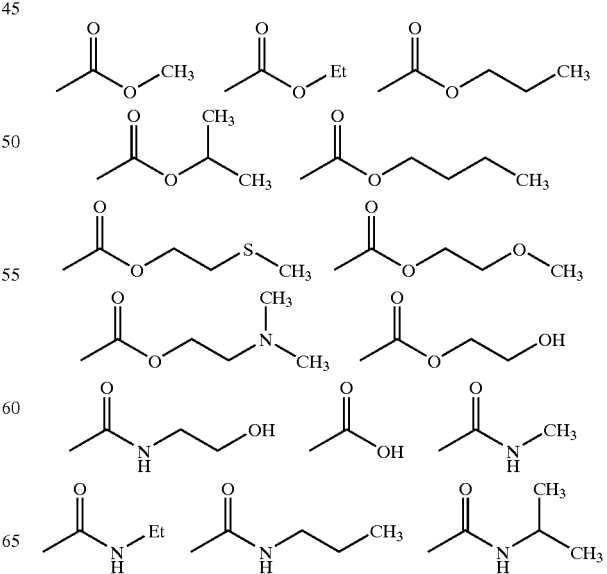

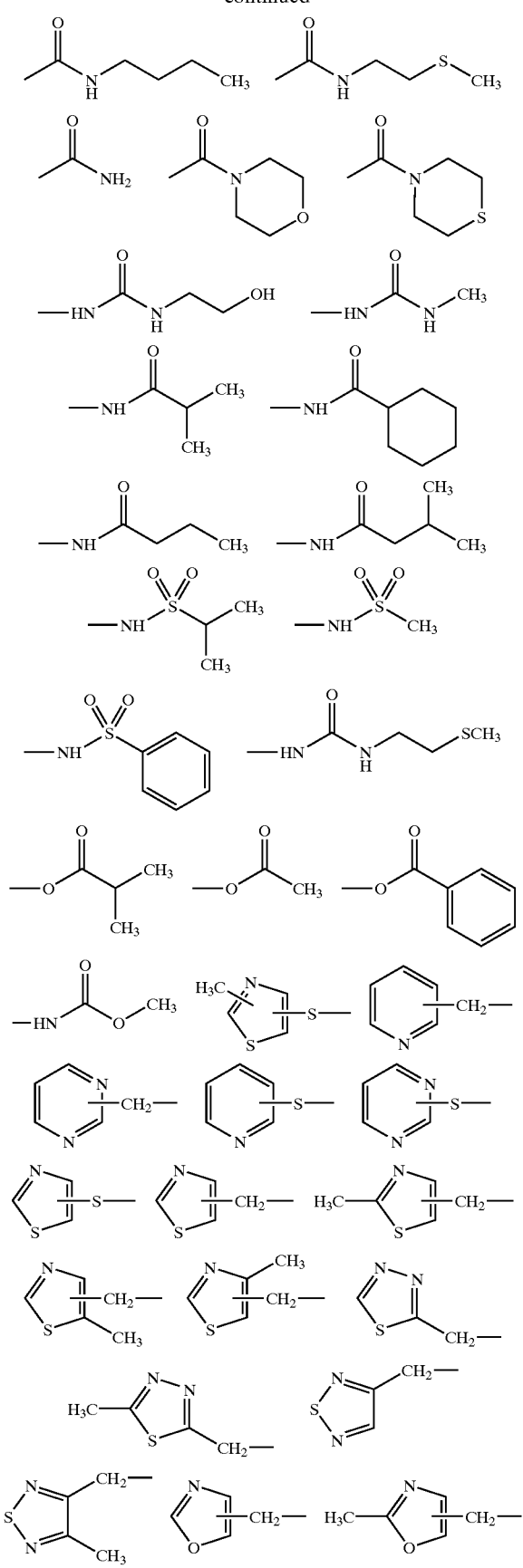
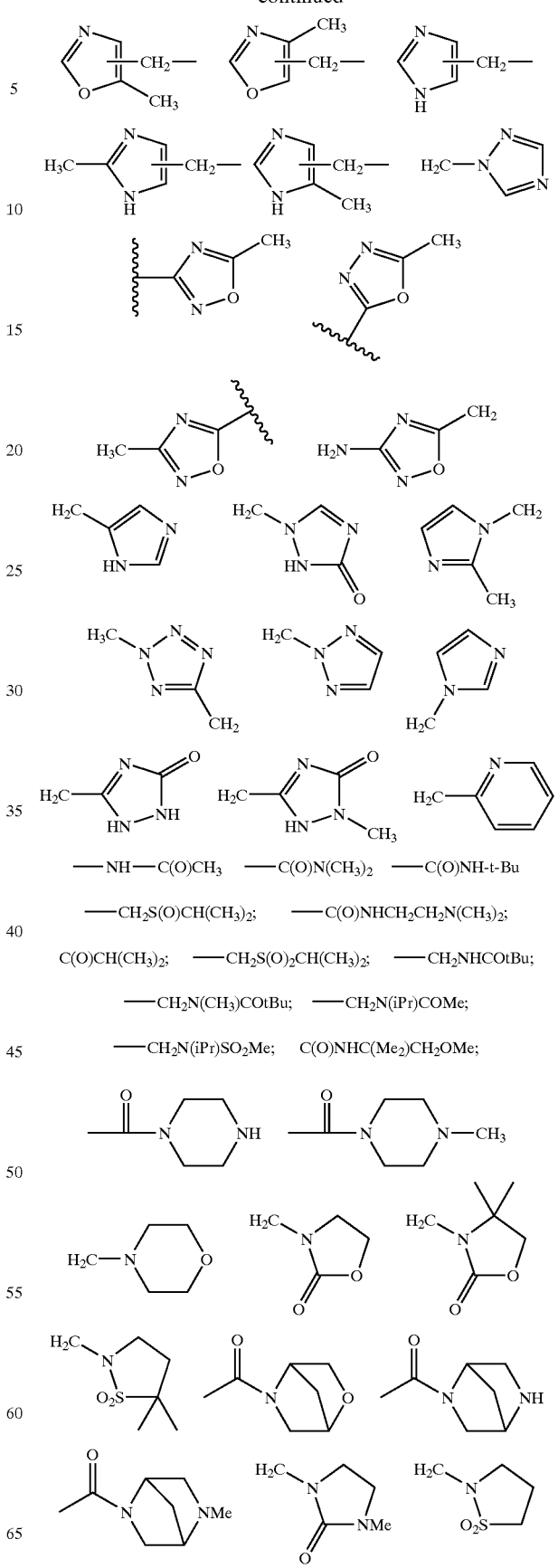

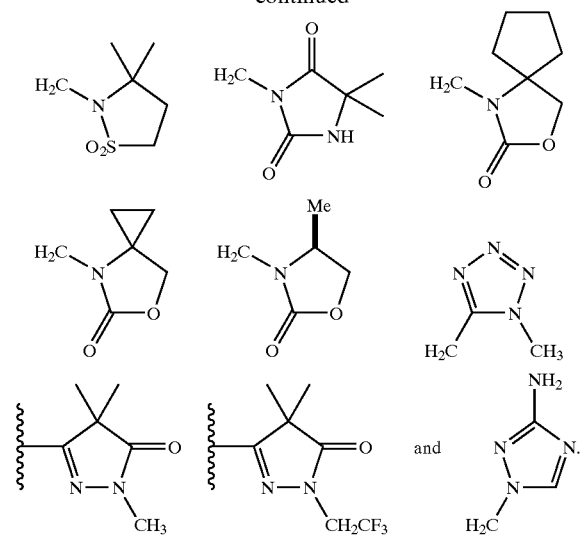
17. The compound of claim 16 selected from the group consisting of:
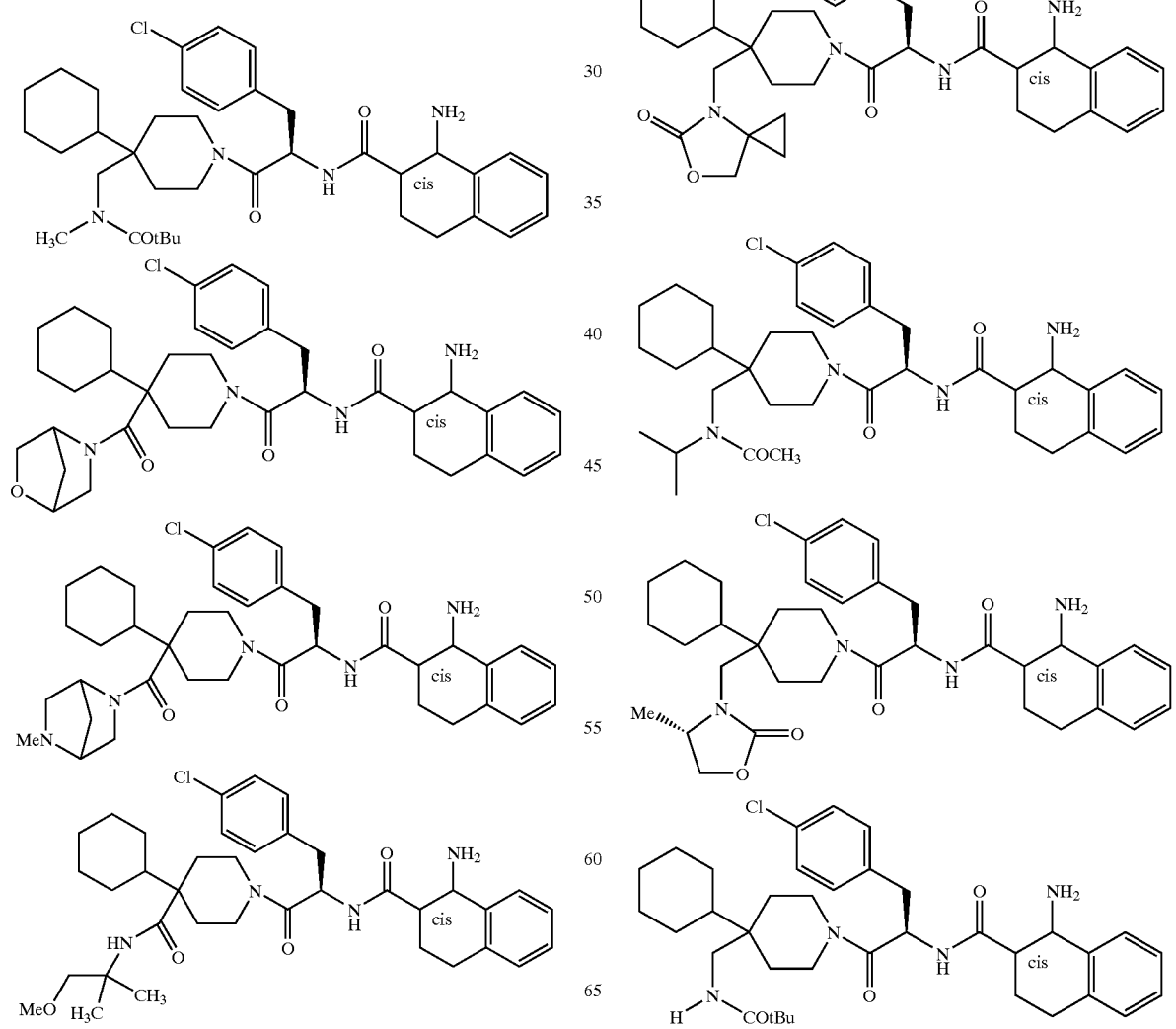

77
-continued
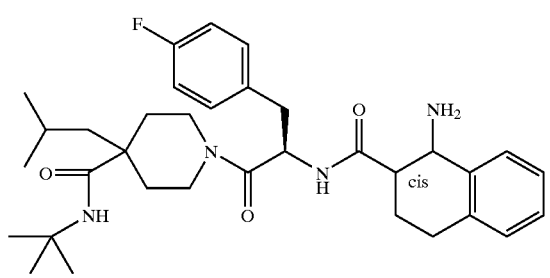
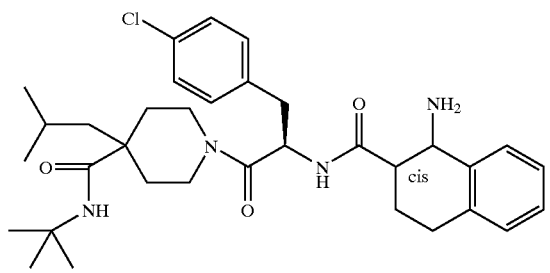
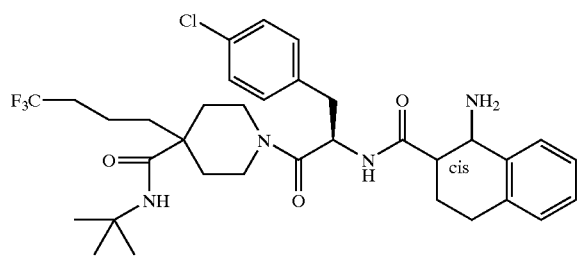
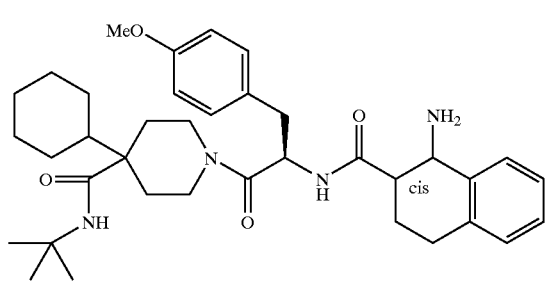
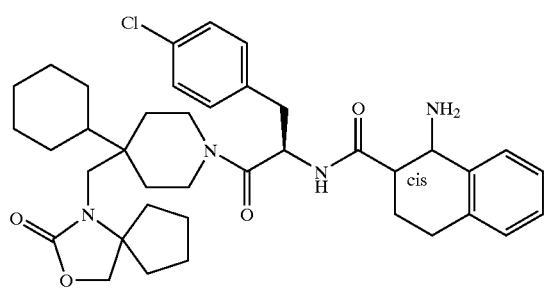
78
-continued
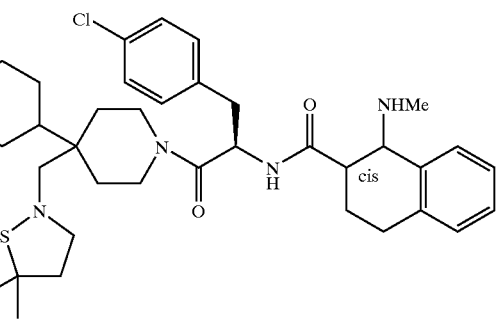
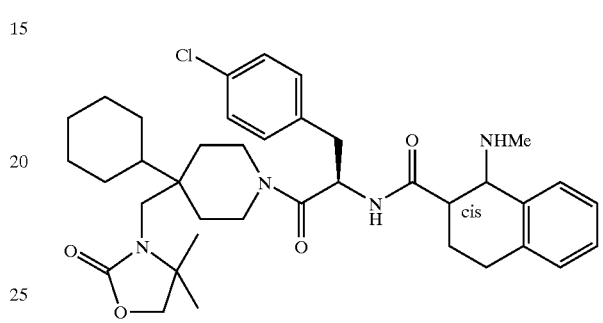
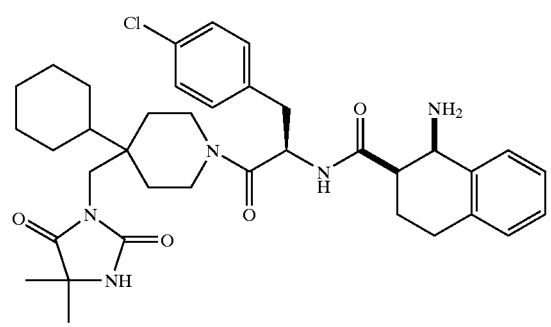
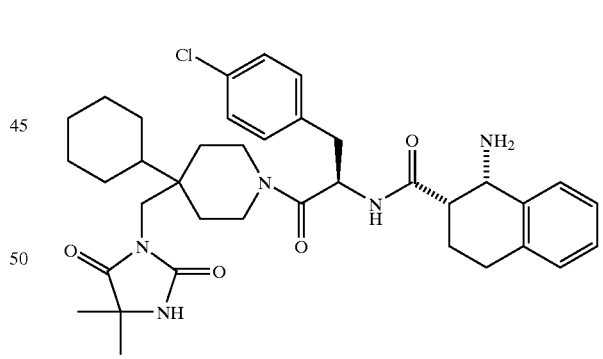
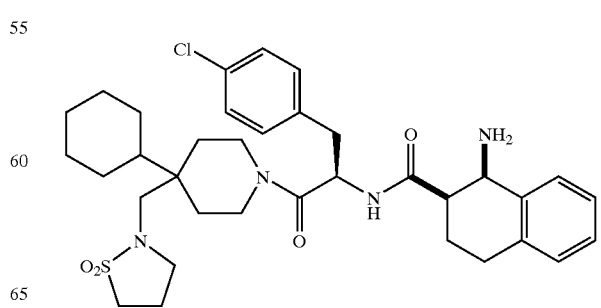

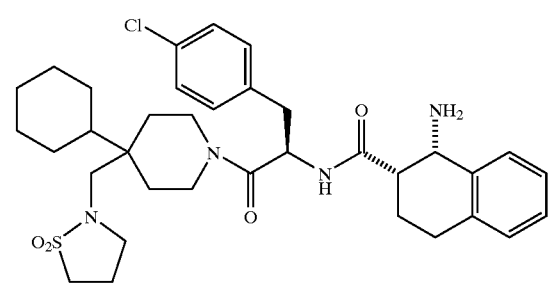
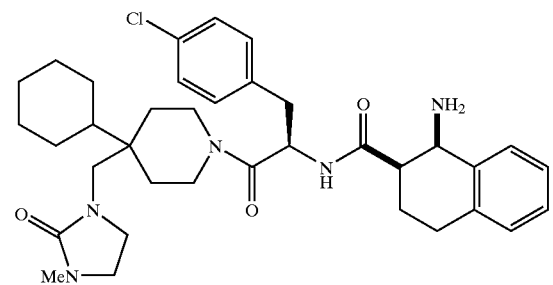
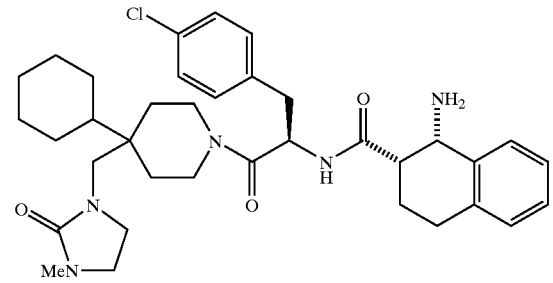
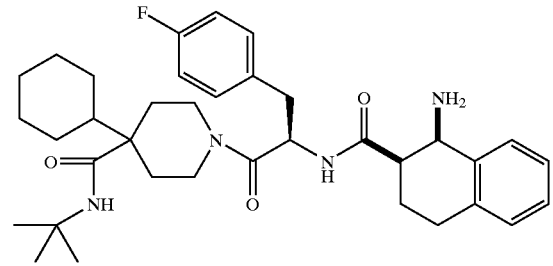
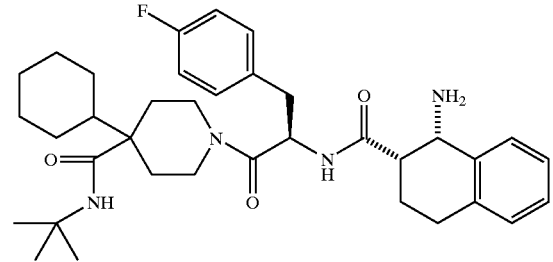
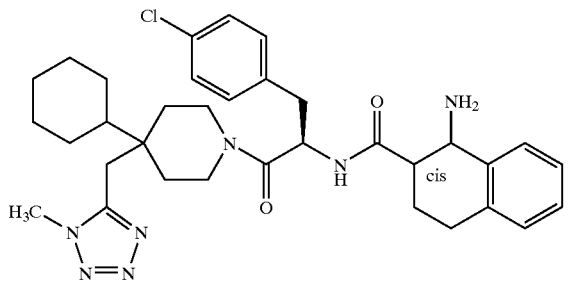
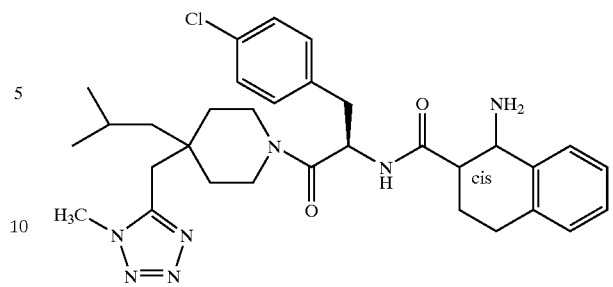
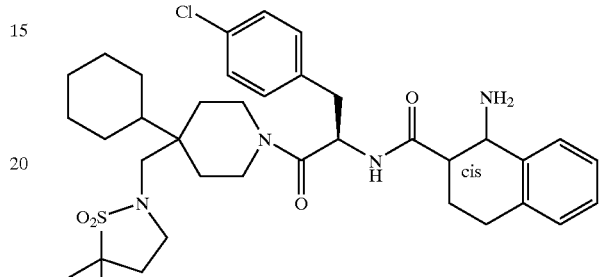
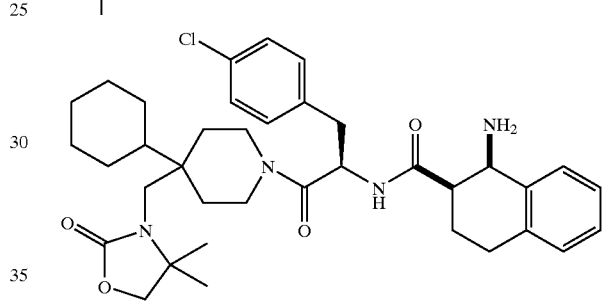
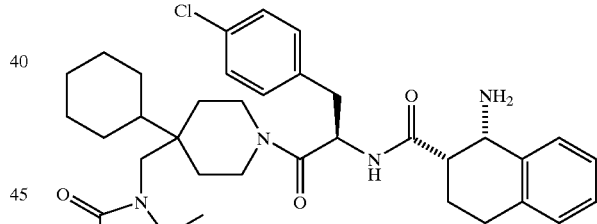
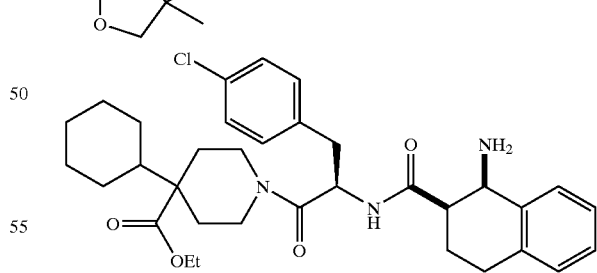
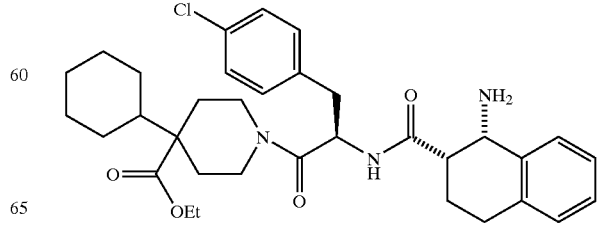

81
-continued
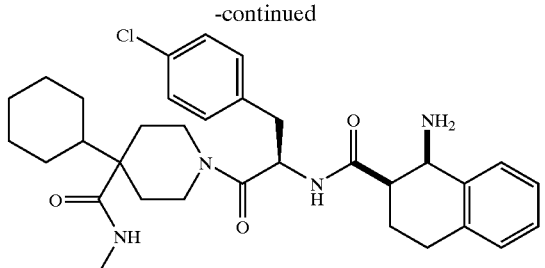
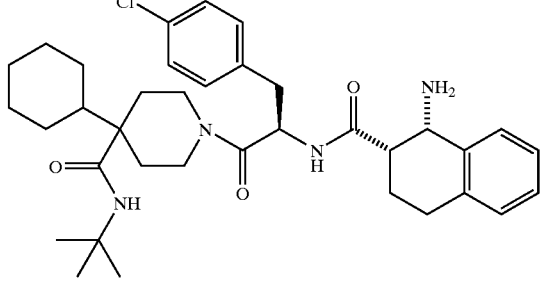
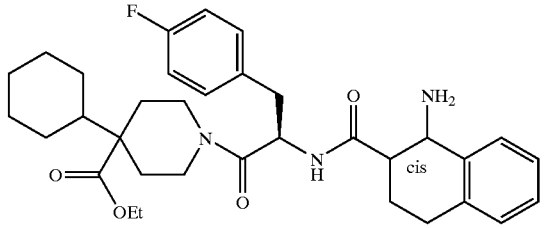
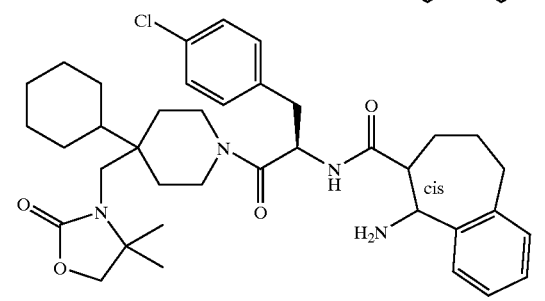
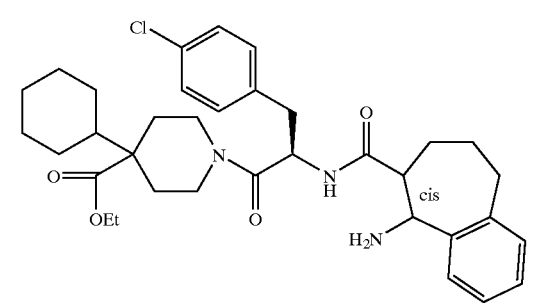
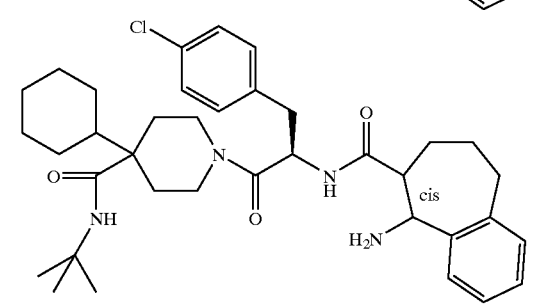
82
-continued
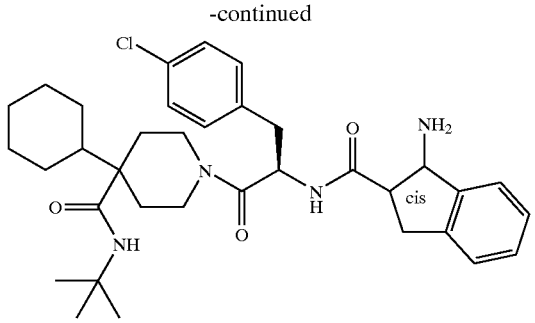
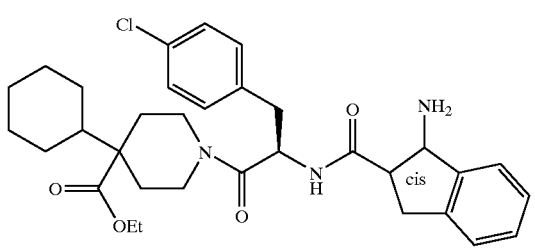
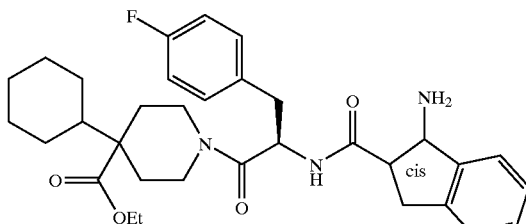
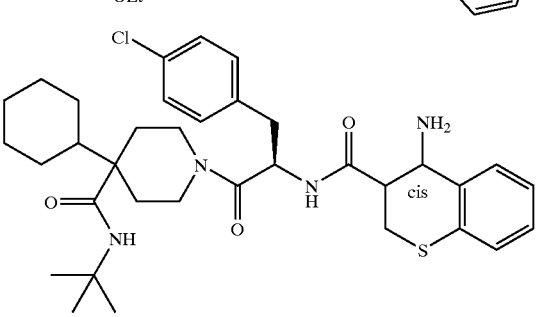
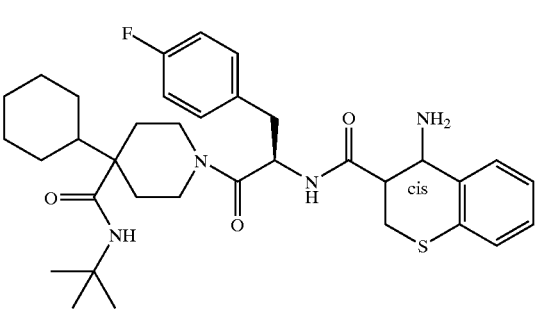
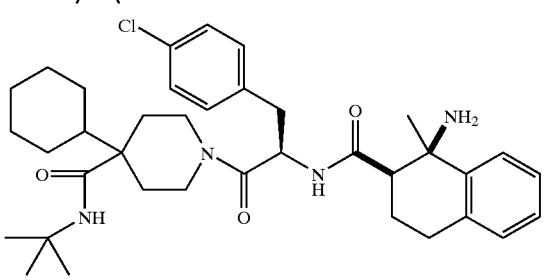

-continued

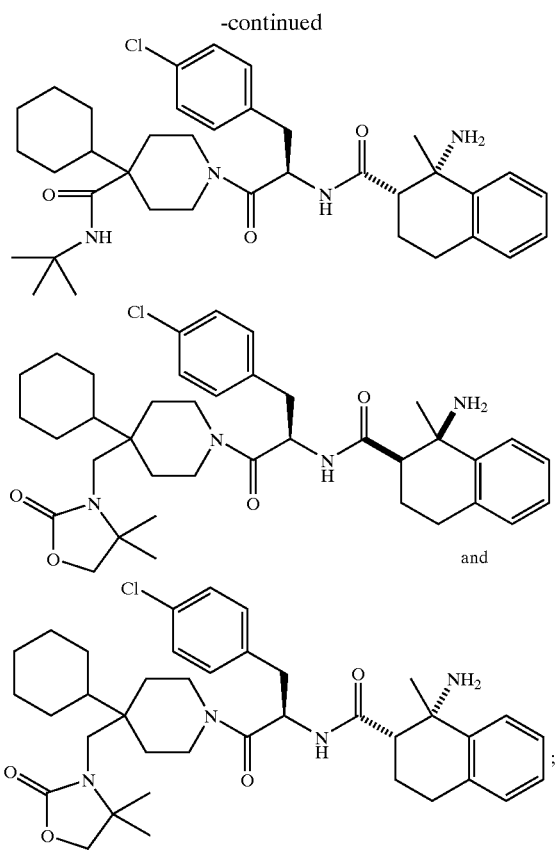

or a pharmaceutically acceptable salt thereof.

18. The compound of claim 1 of formula Ib:

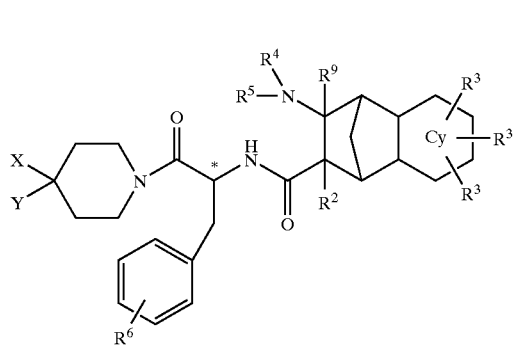

(Ib)

wherein
Cy is phenyl or cyclohexyl,
  wherein Cy is substituted with one to three groups independently selected from $R^3$;
n is 1 or 2;
$R^2$ is selected from the group consisting of
  hydrogen,
  $C_{1-6}$ alkyl, and
  $C_{5-6}$ cycloalkyl;
each $R^3$ is independently selected from
  hydrogen,
  $C_{1-8}$ alkyl,
  $(CH_2)_n$-aryl,
  $(CH_2)_nC_{3-7}$ cycloalkyl,
  $(CH_2)_n$-heteroaryl,
  halo,
  $OR^7$,
  $NHSO_2R^7$,
  $N(R^7)_2$,
  $C\equiv N$
  $CO_2R^7$,
  $C(R^7)(R^7)N(R^7)_2$,
  $NO_2$,
  $SO_2N(R^7)_2$,
  $S(O)_mR^7$,
  $CF_3$, and
  $OCF_3$;
$R^4$ and $R^5$ are each independently selected from the group consisting of
  hydrogen,
  $C_{1-6}$ alkyl, and
  $C_{5-6}$ cycloalkyl;
or $R^4$ and $R^5$ together with the nitrogen to which they are attached form a 5- to 8-membered ring optionally containing an additional heteroatom selected from O, S, and $NR^7$;
  wherein alkyl and cycloalkyl are unsubstituted or substituted with one to three groups independently selected from $R^6$ and oxo;
$R^6$ is selected from the group consisting of
  $C_{1-8}$ alkyl,
  $(CH_2)_n$-aryl,
  $(CH_2)_nC_{3-7}$ cycloalkyl,
  $(CH_2)_n$-heteroaryl,
  halo,
  $OR^7$,
  $NHSO_2R^7$,
  $N(R^7)_2$,
  $C\equiv N$,
  $CO_2R^7$,
  $C(R^7)(R^7)N(R^7)_2$,
  $NO_2$,
  $SO_2N(R^7)_2$,
  $S(O)_mR^7$,
  $CF_3$ and
  $OCF_3$;
    each $R^7$ is independently selected from the group consisting of
      hydrogen,
      $C_{1-8}$ alkyl, and
      $C_{3-6}$ cycloalkyl;
    each $R^8$ is independently selected from the group consisting of
      hydrogen,
      $C_{1-5}$ alkyl,
      aryl,
      heteroaryl, and
      $C_{5-6}$ cycloalkyl;
      wherein aryl and heteroaryl are unsubstituted or substituted with one to three groups independently selected from $R^6$; and alkyl and cycloallkyl are unsubstituted or substituted with one to three groups independently selected from $R^6$ and oxo;
      or two $R^8$ groups together with the atoms to which they are attached form a 5- to 8-membered mono- or bi-cyclic ring optionally containing an additional heteroatom selected from O, S, and $NR^7$;
$R^9$ is hydrogen or $C_{1-4}$ alkyl;
X is selected from the group consisting of
  $C_{1-8}$ alkyl,
  $(CH_2)_nC_{3-8}$ cycloalkyl,
  $(CH_2)_n$aryl, (CH$_2$)$_n$heteroaryl,
(CH$_2$)$_n$heterocyclyl,
(CH$_2$)$_n$C≡N,
(CH$_2$)$_n$CON(R$^8$R$^8$),
(CH$_2$)$_n$CO$_2$R$^8$,
(CH$_2$)$_n$COR$^8$
(CH$_2$)$_n$NR$^8$C(O)R$^8$,
(CH$_2$)$_n$NR$^8$CO$_2$R$^8$,
(CH$_2$)$_n$NR$^8$C(O)N(R$^8$)$_2$,
(CH$_2$)$_n$NR$^8$SO$_2$R$^8$,
(CH$_2$)$_n$S(O)mR$^8$,
(CH$_2$)$_n$SO$_2$N(R$^8$)(R$^8$),
(CH$_2$)$_n$OR$^8$,
(CH$_2$)$_n$OC(O)R$^8$,
(CH$_2$)$_n$OC(O)OR$^8$,
(CH$_2$)$_n$OC(O)N(R$^8$)$_2$,
(CH$_2$)$_n$N(R$^8$)(R$^8$), and
(CH$_2$)$_n$NR$^8$SO$_2$N(R$^8$)(R$^8$);

wherein aryl and heteroaryl are unsubstituted or substituted with one to three groups selected from R$^6$; and alkyl, (CH$_2$)$_n$, cycloalkyl, and heterocyclyl are unsubstituted or substituted with one to four groups independently selected from R$^6$ and oxo;

Y is selected from the group consisting of
hydrogen,
C$_{1-8}$ alkyl,
(CH$_2$)$_n$C$_{3-6}$ cycloalkyl,
(CH$_2$)$_n$aryl, and
(CH$_2$)$_n$heteroaryl;

wherein aryl and heteroaryl are unsubstituted or substituted with one to three groups selected from R$^6$; and alkyl, (CH$_2$)$_n$, and cycloalkyl are unsubstituted or substituted with one to three groups selected from R$^6$ and oxo;

or a pharmaceutically acceptable salt thereof.

19. The compound of claim 18 wherein the carbon atom marked with * has the R configuration.

20. The compound of claim 18 wherein X is selected from the group consisting of:

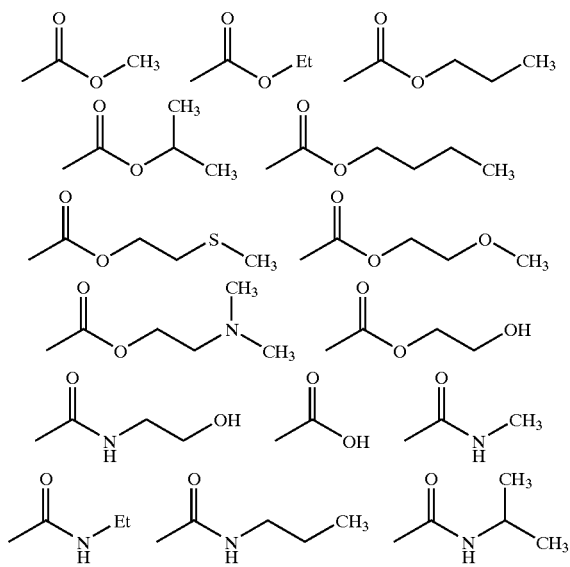
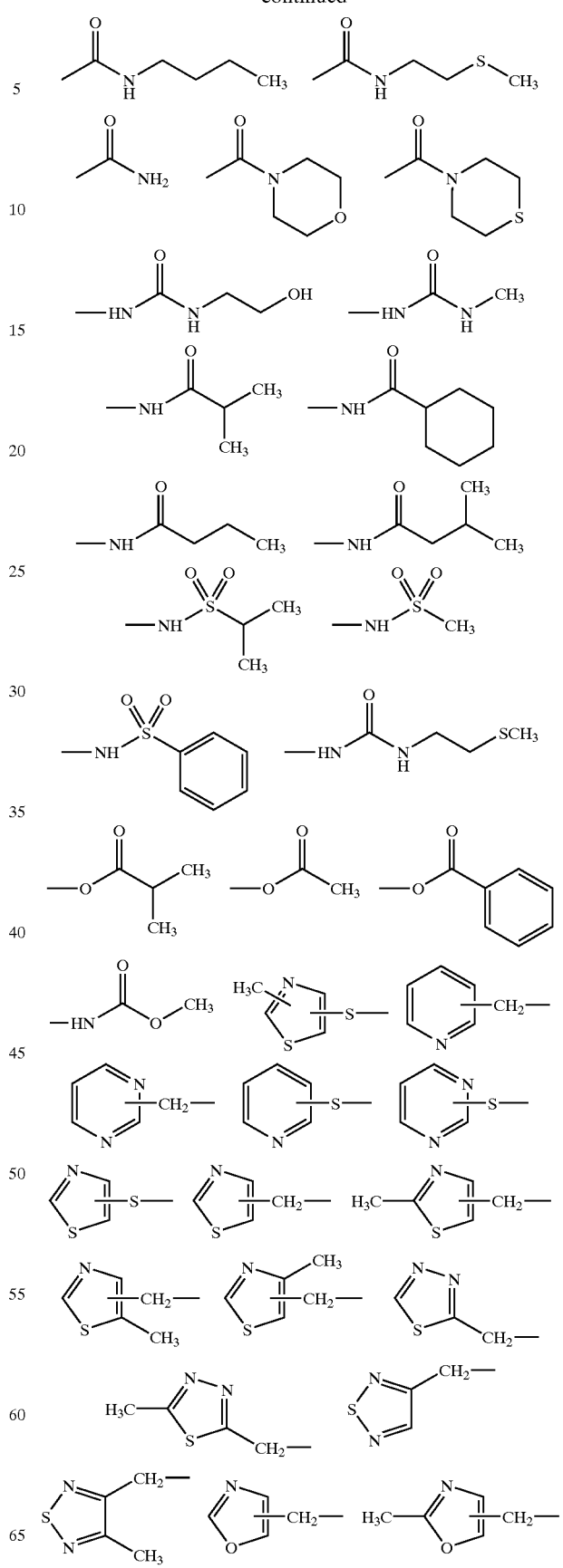

-continued
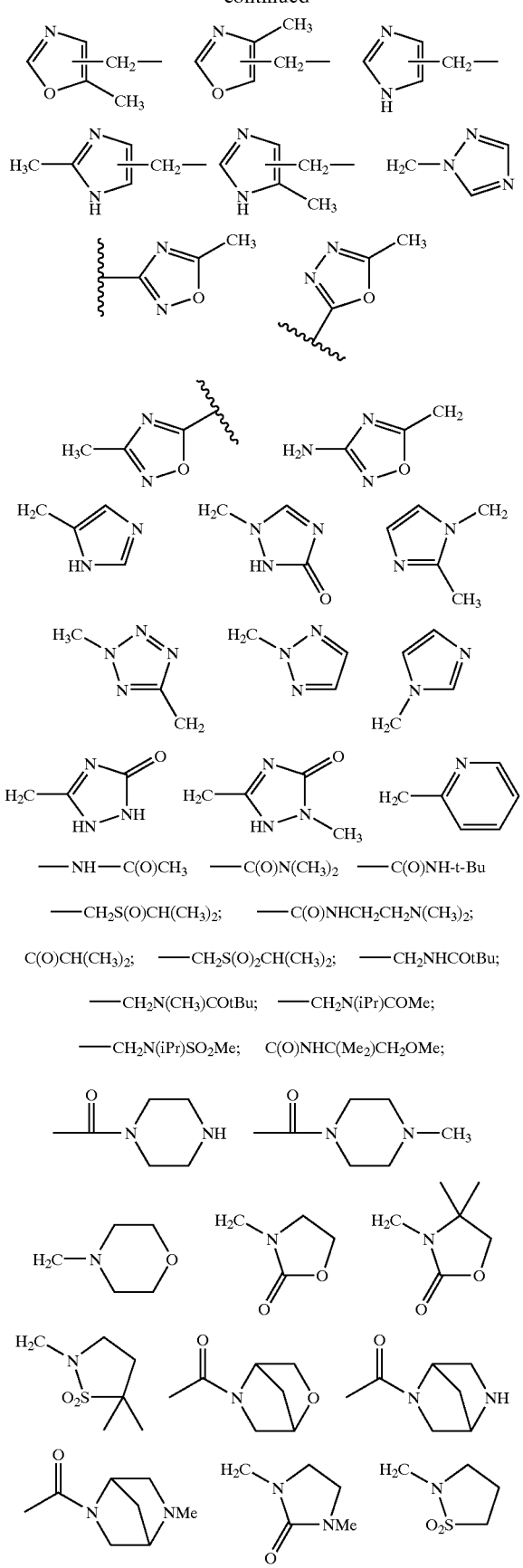
-continued
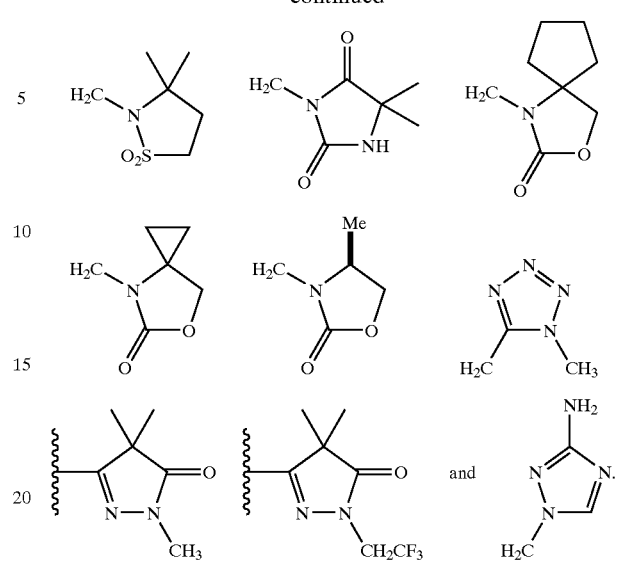
21. The compound of claim 20 selected from the group consisting of:
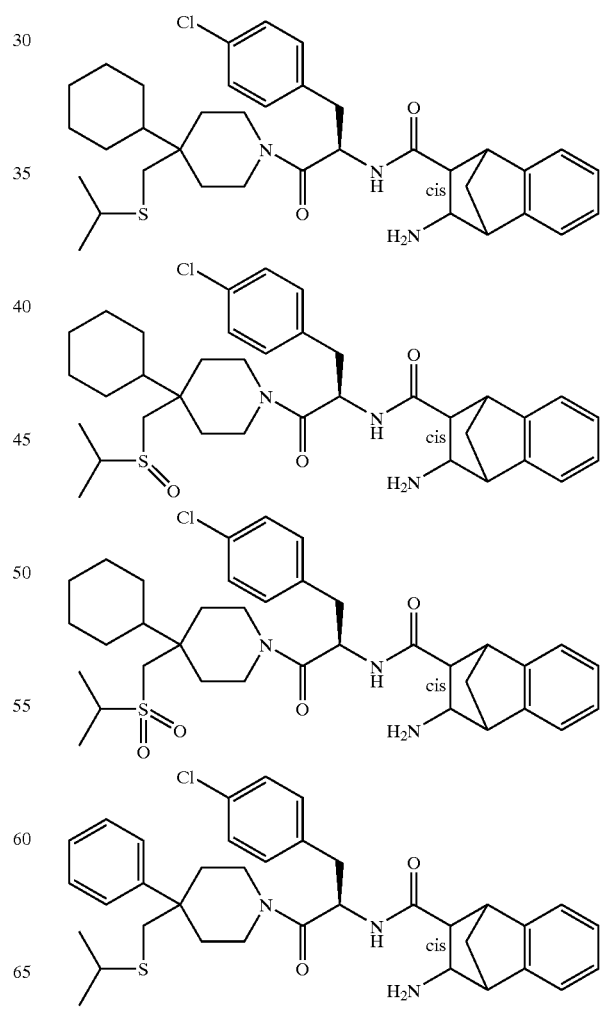

89
-continued

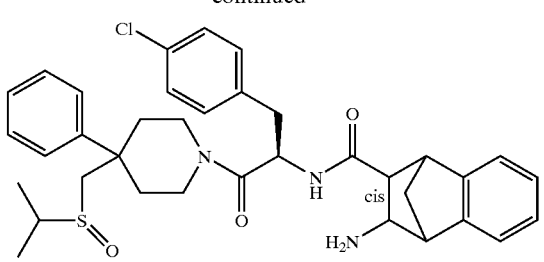
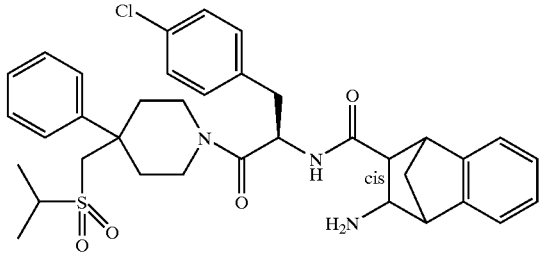
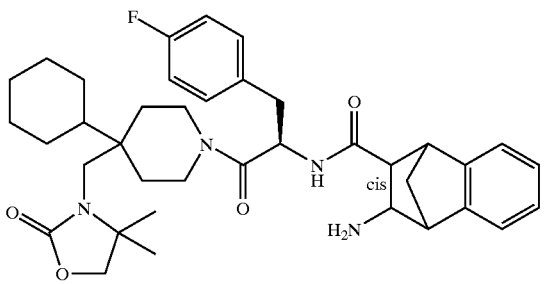
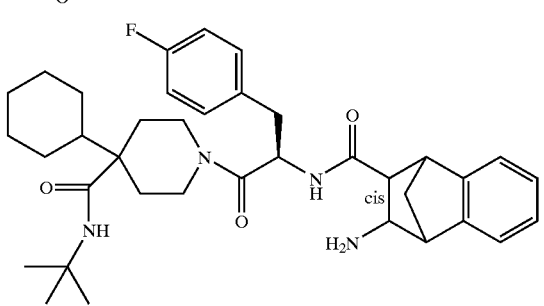
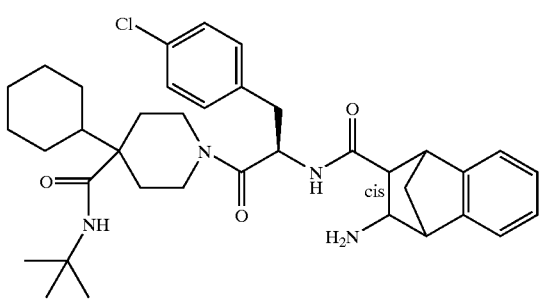
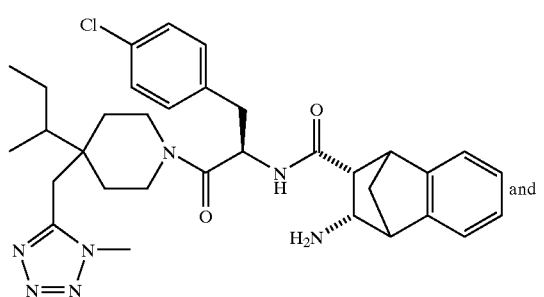

90
-continued

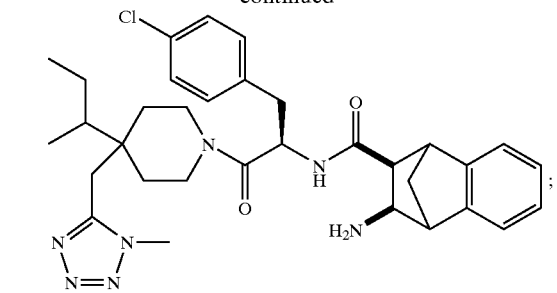

or a pharmaceutically acceptable salt thereof.

22. A method for the treatment or prevention of disorders, diseases or conditions responsive to the activation of the melanocortin-4 receptor in a subject in need thereof which comprises administering to the subject a therapeutically or prophylactically effective amount of a compound according to claim 1.

23. A method for the treatment of obesity in a subject in need thereof which comprises administering to the subject a therapeutically effective amount of a compound according to claim 1.

24. A method for the treatment of diabetes mellitus in a subject in need thereof comprising administering to the subject a therapeutically effective amount of a compound according to claim 1.

25. A method for the treatment of male or female sexual dysfunction in a subject in need thereof comprising administering to the subject a therapeutically effective amount of a compound according to claim 1.

26. A method for the treatment of erectile dysfunction in a subject in need thereof comprising administering to the subject a therapeutically or prophylactically effective amount of a compound according to claim 1.

27. A pharmaceutical composition which comprises a compound of claim 1 and a pharmaceutically acceptable carrier.

28. A pharmaceutical composition of claim 27 further comprising a second active ingredient selected from the group consisting of an insulin sensitizer, an insulin mimetic, a sulfonylurea, an α-glucosidase inhibitor, an HMG-CoA reductase inhibitor, a sequestrant cholesterol lowering agent, a β3 adrenergic receptor agonist, a neuropeptide Y antagonist, a type V cyclic-GMP-selective phosphodiesterase inhibitor, an $α_2$-adrenergic receptor antagonist, and a dopaminergic agent.

29. A method of treating erectile dysfunction in a subject in need thereof, comprising administering to the subject a therapeutically effective amount of the composition of claim 28.

* * * * *